US005614365A

United States Patent [19]
Tabor et al.

[11] Patent Number: 5,614,365
[45] Date of Patent: Mar. 25, 1997

[54] DNA POLYMERASE HAVING MODIFIED NUCLEOTIDE BINDING SITE FOR DNA SEQUENCING

[75] Inventors: Stanley Tabor, Cambridge; Charles Richardson, Chestnut Hill, both of Mass.

[73] Assignee: President & Fellow of Harvard College, Cambridge, Mass.

[21] Appl. No.: 337,615

[22] Filed: Nov. 10, 1994

Related U.S. Application Data

[63] Continuation-in-part of Ser. No. 324,437, Oct. 17, 1994, abandoned.

[51] Int. Cl.[6] .............................. C12Q 1/68; C12P 19/34; C12N 9/00; C07H 21/02
[52] U.S. Cl. ...................... 435/6; 435/91.2; 435/91.1; 435/172.3; 435/69.1; 536/23.1; 530/350
[58] Field of Search ........................ 435/6, 5, 91.2, 435/91.1, 172.3, 69.1; 204/182.8; 536/23.1; 530/350

[56] References Cited

U.S. PATENT DOCUMENTS

| | | |
|---|---|---|
| 4,707,235 | 11/1987 | Englert et al. . |
| 4,795,699 | 1/1989 | Tabor et al. . |
| 4,921,794 | 5/1990 | Tabor et al. . |
| 4,942,130 | 7/1990 | Tabor et al. . |
| 4,946,786 | 8/1990 | Tabor et al. . |
| 4,952,496 | 8/1990 | Studier et al. . |
| 4,962,020 | 10/1990 | Tabor et al. . |
| 4,994,372 | 2/1991 | Tabor et al. . |
| 4,997,818 | 5/1991 | McCaffrey et al. . |
| 5,001,050 | 3/1991 | Blanco et al. . |
| 5,079,352 | 1/1992 | Gelfand et al. . |
| 5,108,892 | 4/1992 | Burke et al. . |
| 5,122,345 | 6/1992 | Tabor et al. ............................ 422/116 |
| 5,145,776 | 8/1992 | Tabor et al. . |
| 5,173,411 | 12/1992 | Tabor et al. . |
| 5,198,543 | 3/1993 | Blanco et al. . |
| 5,210,036 | 5/1993 | Comb et al. . |
| 5,266,466 | 11/1993 | Tabor et al. . |
| 5,270,179 | 12/1993 | Chatterjee . |
| 5,322,785 | 6/1994 | Comb et al. . |
| 5,352,600 | 10/1994 | Gelfand et al. . |
| 5,352,778 | 10/1994 | Comb et al. . |

FOREIGN PATENT DOCUMENTS

| | | |
|---|---|---|
| 0258017 | 3/1988 | European Pat. Off. . |
| 0351138 | 1/1990 | European Pat. Off. . |
| 0386859 | 9/1990 | European Pat. Off. . |
| 0516245 | 12/1992 | European Pat. Off. . |
| 9008839 | 8/1990 | WIPO . |
| 9102090 | 2/1991 | WIPO . |
| 9302212 | 7/1991 | WIPO . |
| 9116446 | 10/1991 | WIPO . |
| 9504162 | 2/1995 | WIPO . |

OTHER PUBLICATIONS

Reha Krantz et al. J. of Virology, 67:60–66, 1993.
Donlin and Johnson, Biochemistry 33: 14908–14917 1994.
Gibbs et al. PNAS 85: 6672–6676 1988.
Larder et al. EMBO 6: 169–175 1987.
Derse et al. JBC 257: 10251–10260 1982.
Prasad et al. PNAS 88: 11363–11367 1991.
Astatke et al., "Deoxynucleoside Triphosphate and Pyrophosphate Binding Sites in the Catalytically Competent Ternary Complex for the Polymerase Reaction Catalyzed by DNA Polymerase I (Klenow Fragment)," *J. Biol. Chem.* 270:1945–1954 (1995).
Polesky et al., "Identification of Residues Critical for the Polymerase Activity of the Klenow Fragment of DNA Polymerase I from *Escherichia coli*", *J. Biol. Chem.* 265(24);14579–14591 (1990).

(List continued on next page.)

*Primary Examiner*—W. Gary Jones
*Assistant Examiner*—Dianne Rees
*Attorney, Agent, or Firm*—Lyon & Lyon

[57] ABSTRACT

Modified gene encoding a modified DNA polymerase wherein the modified polymerase incorporates dideoxynucleotides at least 20-fold better compared to the corresponding deoxynucleotides as compared with the corresponding naturally-occurring DNA polymerase.

108 Claims, 6 Drawing Sheets

OTHER PUBLICATIONS

Prasad et al., "Isolation and Characterization of a dideoxyguanosine triphosphate-resistant mutant of human immunodeficiency virus reverse transcriptase," *Proc. Natl. Acad. Sci. USA* 88:11363–11367 (1991).

Prober et al., "A System for Rapid DNA Sequencing with Fluorescent Chain-Terminating Dideoxynucleotides," *Science* 238:336–341 (1987).

Reha-Krantz et al., "Mutational Analysis of Bacteriophage T4 DNA Polymerase," from Abstracts for Poster Presentations, presented at a meeting entitled The Fidelity of DNA Synthesis: Structural and Mechanistic Perspectives, Beaufort, North Carolina, Sep. 24–29, 1989.

Reha-Krantz et al., "Bacteriophage T4 DNA Polymerase Mutations that Confer Sensitivity to the PP Analog Phosphonoacetic Acid," *J. Virology* 67(1):60–66 (1993).

Reha-Krantz et al., "Motif A of Bacteriophage T4 DNA Polymerase: Role in Primer Extension and DNA Replication Fidelity," *J. Biol. Chem.* 269(8):5635–5643 (1994).

Sanger et al., "DNA sequencing with chain-terminating inhibitors," *Proc. Natl. Acad. Sci. USA* 74(12):5463–5467 (1977).

Sawaya et al., "Crystal Structure of Rat DAN Polymerase β: Evidence for a Common Polymerase Mechanism," *Science* 264:1930–1935 (1994).

Smith et al., "The synthesis of oligonucleotides containing an aliphatic amino group at the 5' terminus: synthesis of fluorescent DNA primers for use in DNA sequence analysis," *Nucleic Acids Research* 13(7):2399–2413 (1985).

Smith et al., "Fluorescence detection in automated DNA sequence analysis," *Nature* 321:674–679 (1986).

Song et al., "Mutagenesis of the Glu-89 Residue in Human Immunodeficiency Virus Type 1 (HIV-1) and HIV-2 Reverse Transcriptase: Effects on Nucleoside Analog Resistance," *J. Virology* 66(12):7568–7571 (1992).

Sousa et al., "Crystal struture of bacteriophge T7 RNA polymerase at 3.3 Å resolution," *Nature* 364:593–599 (1993).

St. Clair et al., "Resistance to ddI and Sensitivity to AZT Indusced by a Mutation in HIV-1 Reverse Transcriptase," *Science* 253:1557–1559 (1991).

Tabor and Richardson, "Effect of manganese ions on the incorporation of dideoxynucleotides by bacteriophage T7 DNA polymerase and *Escherichia coli* DNA polymerase I," *Proc. Natl. Acad. Sci. USA* 86:4076–4080 (1989).

Tabor et al., "DNA Sequence Analysis with a Modified Bacteriophage T7 DA Polymerase," 'Effect of Pyrophosphorolysis and Metal Ions' *J. Biol. Chem.* 265(14):8322–8328 (1990).

Tisdale et al., "Rapid in vitro selection of human immunodeficiency virus type 1 resistant to 3'-thiacytidine inhibitors due to a mutation in the YMDD region of reverse transcriptase," *Proc. Natl. Acad. Sci. USA* 90:5653–5656 (1993).

Toneguzzo et al., "Use of a Chemically Modified T7 DNA Polymerase for Manual and Automated Sequencing of Supercoiled DNA," *BioTechniques* 6(5):460–469 (1988).

Basu et al., "Identification and Amino Acid Sequence of the Deoxynucleoside Triphosphate Binding Site in *Escherichia coli* DNA Polymerase," *Biochemistry* 26:1704–1709 (1987).

Beese et al., "Crystal Structures of the Klenow Fragment of DNA Polymerase I Complexed with Deoxynucleoside Triphosphate and Pyrophosphate," *Biochemistry* 32:14094–14101 (1993).

Boucher et al., "Ordered Appearance of Zidovudine Resistance Mutations during Treatment of 18 Human Immunodeficiency Virus–Positive Subject," *J. Infect. Dis.* 165:105–110 (1992).

Carroll et al., "A Mutant of DNA Polymerase I (Klenow Fragment) with Reduced Fidelity," *Biochemistry* 30:804–813 (1991).

Derse et al., "Characterization of the DNA Polymerases Induced by a Group of Herpes Simplex Virus Type I Variants Selected for Growth in the Presence of Phosphonoformic Acid," *J. Biol. Chem.* 257(17):10251–10260 (1982).

Donlin and Johnson, "Mutants Affecting Nucleotide Recognition by T7 DNA Polymerase," *Biochemistry* 33(499:14908–14917 (1994).

Gibbs et al., "Identification of amino acids in herpes simplex virus DNA polymerase involved in substrate and drug recognition," *Proc. Natl. Acad. Sci. USA* 85:6672–6676 (1988).

Joyce and Seitz, "Function and Structure Relationships in DNA Polymerases," *Annu. Rev. Biochem.* 63:777–822 (1994).

Kambara et al., "Optimization of Parameters in a DNA Sequenator Using Fluorescence Detection," *BioTechnology* 6:816–821 (1988).

Kellam et al., "Fifth mutation in human immunodeficiency virus tupe 1 reverse transcriptase contributes to the development of high level resistance to zidovudine," *Proc. Natl. Acad. Sci. USA* 89:1934–1938 (1992).

Lacey et al., "Biochemical Studies on the Reverse Transcriptase and RNase H Activities from Human Immunodeficiency Virus Strains Resistant to 3'-Azido-3'-deoxythymidine," *J. Biol. Chem.* 267(22):15789–15794 (1992).

Lacey and Larder, "Mutagenic Study of Codons 74 and 215 of the Human Immunodeficiency Virus Type 1 Reverse Transcriptase, Which are Significant in Nucleoside Analog Resistance," *Antimicrobial Agents and Chemotheraphy* 68:3421–3424 (1994).

Lacey and Larder, "Novel Mutation (V75T) in Human Immunodeficiency Virus Type 1 Reverse Transcriptase Confers Resistance to 2',3'-Didehydro-2',3'-Dideoxythymidine in Cell Culture," *Antimicrobial Agents and Chemotheraphy* 38:1428–1432 (1994).

Larder et al., "Related functional domains in virus DNA polymerases," *EMBO J.* 6(1):169–175 (1987).

Larder, "3'-Azido-3'-Deoxythymidine Resistance Suppressed by a Mutation Conferring Human Immunodeficiency Virus Type 1 Resistance to Nonnucleoside Reverse Transcriptase Inhibitors," *Antimicrobial Agents and Chemotheraphy* 36:2664–2669 (1992).

Larder et al., "Multiple Mutations in HIV-1 Reverse Transcriptase Confer High-Level Resistance to Zidovudine (AZT)", *Science* 246:1155–1158 (1989).

Pandey et al., "Role of Lysine 758 of *Escherichia coli* DNA Polymerase I as Assessed by Site-directed Mutagenesis," *J. Biol. Chem.* 269(18):13259–13265 (1994).

Pelletier et al., "Structures of Ternary Complexes of Rat DNA Polymerase β, a DNA Template–Primer, and ddCTP," *Science* 254:1891–1903 (1994).

Polesky et al., "Side Chains Involved in Catalysis of the Polymerase Reaction of DNA Polymerase I from *Escherichia coli*," *J. Biol. Chem.* 267(12):8417–8428 (1992).

Ito and Braithwaite, "Compilation and Alignment of DNA Polymerase Sequences," *Nucleic Acids Research* 19:4045–4057 (1991).

Foury and Vanderstraeten, "Yeast mitochondrial DNA mutators with deficient proofreading exonucleolytic activity," *EMBO J.* 11(7):2717–2726 (1992).

DNA POLYMERASE HAVING MODIFIED NUCLEOTIDE BINDING SITE FOR DNA SEQUENCING

This invention was made with government support including a grant from the U.S. Dept of Energy, contract number DE-FG02-88ER60688. The U.S. government may have certain rights in the invention.

This application is a continuation-in-part of the application of Tabor and Richardson, entitled "DNA POLYMERASES HAVING MODIFIED NUCLEOTIDE BINDING SITE FOR DNA SEQUENCING," Ser. No. 08/324,437 filed Oct. 17, 1994, now abandoned the whole of which (including drawings) is hereby incorporated by reference herein.

BACKGROUND OF THE INVENTION

This invention relates to DNA polymerases suitable for DNA sequencing and to automated and manual methods for DNA sequencing.

The following is a brief description of art relevant to DNA sequencing techniques. This is provided only to give general guidance to those reading the application, and is not an admission that any art cited herein or referred to explicitly or implicitly is prior art to the appended claims.

DNA sequencing generally involves the generation of four populations of single-stranded DNA fragments having one defined terminus and one variable terminus. The variable terminus generally terminates at specific nucleotide bases (either guanine (G), adenine (A), thymine (T), or cytosine (C)). The four different sets of fragments are each separated on the basis of their length, one procedure being on a high resolution polyacrylamide gel; each band on the gel corresponds colinearly to a specific nucleotide in the DNA sequence, thus identifying the positions in the sequence of the given nucleotide base. See Tabor and Richardson, U.S. Pat. Nos. 4,942,130 and 4,962,020.

There are two general methods of DNA sequencing. One method (Maxam and Gilbert sequencing) involves the chemical degradation of isolated DNA fragments, each labeled with a single radiolabel at its defined terminus, each reaction yielding a limited cleavage specifically at one or more of the four bases (G, A, T or C). The other method (dideoxy or chain-termination sequencing) involves the enzymatic synthesis of a DNA strand. Sanger et al. (*Proc. Nat. Acad. Sci.* USA 74:5463, 1977). Four separate syntheses are generally run, each reaction being caused to terminate at a specific base (G, A, T or C) via incorporation of an appropriate chain terminating nucleotide, such as a dideoxynucleotide. The latter method is preferred since the DNA fragments can be uniformly labelled (instead of end labelled) by the inclusion of a radioactively labeled nucleoside triphosphate and thus the larger DNA fragments contain increasingly more radioactivity. Further, $^{35}$S-labelled nucleotides can be used in place of $^{32}$P-labelled nucleotides, resulting in sharper definition; the reaction products are easier to interpret since each lane corresponds only to either G, A, T or C. The enzymes used for most dideoxy sequencing include T7 DNA polymerase and DNA polymerases isolated from thermophilic organisms such as Taq, Vent, Tth, and others. Other polymerases used to a lesser extent include AMV reverse transcriptase and Klenow fragment of *E. coli* DNA polymerase I.

In the dideoxy chain terminating method a short single-stranded primer is annealed to a single-stranded template. The primer is elongated at its 3'-end by the incorporation of deoxynucleotides (dNMPs) until a dideoxynucleotide (ddNMP) is incorporated. When a ddNMP is incorporated elongation ceases at that base. Other chain terminating agents can be used in place of a ddNTP and the ddNTP can be labelled as discussed below.

Using the above methodology, automated systems for DNA sequence analysis have been developed. One instrument, which was manufactured by EG&G, makes use of conventional dideoxy chain terminating reactions with a radioactively labeled nucleotide. The resulting DNA products are separated by gel electrophoresis. Toneguzzo et al, 6 *Biotechniques* 460, 1988. A detector scans for radioactivity as it passes through the bottom of the gel. Four synthesis reactions are required for each template to be sequenced, as well as four lanes on each gel, a separate lane being used for products terminated by each specific chain terminating agent.

Kambara et al, 6 *Biotechnology* 816, 1988, have used a fluorescent-labelled primer. The resulting fluorescently labelled products are excited with a laser at the bottom of the gel and the fluorescence detected with a CRT monitor. This procedure also requires four synthesis reactions and four lanes on the gel for each template to be sequenced.

Applied Biosystems manufactures an instrument in which four different primers are used, each labelled with a different fluorescent marker. Smith et al., 13 *Nuc. Acid. Res.* 2399, 1985; and 321 *Nature* 674, 1986. Each primer is used in a separate reaction containing one of four dideoxynucleotides. After the four reactions have been carried out the mixtures are combined and the DNA fragments are fractionated in a single lane on a gel. A laser at the bottom of the gel is used to detect fluorescent products after they have been electrophoresed through the gel. This system requires four separate annealing reactions and four separate synthesis reactions for each template, but only a single lane on the gel. Computer analysis of the sequence is made easier by having all four bands in a single lane.

DuPont used to provide an instrument in which a different fluorescent marker was attached to each of four dideoxynucleoside triphosphates. Prober et al., 238 *Science* 336, 1987. A single annealing step, a single polymerase reaction (containing each of the four labelled dideoxynucleoside triphosphates) and a single lane in the sequencing gel are required. The four different fluorescent markers in the DNA products are detected separately as they are electrophoresed through the gel.

Englert et al., U.S. Pat. No. 4,707,235 (1987), describes a multichannel electrophoresis apparatus having a detection means, disposed substantially across the whole width of the gel, that can detect labelled DNA products as they migrate past the detector means in four separate lanes, and identifies the channel or lane in which the sample is located. Preferably, radioisotopic labels are used.

Inherent to procedures currently used for DNA sequence analysis is the necessity to separate either radioactively or fluorescently-labelled DNA products by a gel permeation procedure such as polyacrylamide gel electrophoresis, and then detect their locations relative to one another along the axis of movement through the gel. The accuracy of this procedure is determined in part by the uniformity of the signal in bands which have permeated approximately the same distance through the gel. Differences or variations in signal intensities between nearby bands create several problems. First, they decrease the sensitivity of the method, which is limited by the ability to detect the bands containing the weakest signals. Second, they create difficulties in determining whether a band with a weak signal is a true signal due to the incorporation of a chain terminating agent, or an artifact due to a pause site in the DNA where the polymerase has dissociated. Third, they decrease the accuracy in determining the DNA sequence between closely spaced bands since the strong signal of one band may mask the weak signal of its neighbor. See Tabor and Richardson, supra.

Variation in band intensity can arise from an inherent property of most DNA polymerases. Most DNA polymerases discriminate against the chain terminating dideoynucleotides used in DNA sequence analysis. T4 DNA polymerase discriminates against ddNTPs to such an extent that it cannot be used for DNA sequencing. E. coli DNA polymerase I, Taq, and Vent DNA polymerase also discriminate strongly against ddNTPs, each incorporating a ddNMP a thousand times slower than the corresponding dNTP. Tabor and Richardson supra, (both hereby incorporated by reference herein) have shown that T7 DNA polymerase lies at the other end of the spectrum, discriminating against ddNTPs only several fold. If a DNA polymerase discriminated against a ddNTP to the same extent at all sequences, this problem could be overcome by simply altering the ratio of ddNTPs to dNTPs. Such an approach has been used with E. coli DNA polymerase I and Taq DNA polymerase. However, the extent of discrimination varies with the adjacent DNA sequences, which leads to wide variation in the intensity of adjacent radioactive fragments. The intensity of specific fragments can vary by 50-fold for E. coli DNA polymerase I but only several fold for T7 DNA polymerase. Consequently, the intensity of bands on a DNA sequencing gel produced by T7 DNA polymerase are of similar intensity thus facilitating their detection and analysis by automated procedures. In addition, procedures that even further reduce the discrimination against dideoxynucleotides by T7 DNA polymerase are described such that it incorporates dideoxynucleotides equally as well as deoxynucleotides. These procedures and conditions also reduce but do not eliminate discrimination by other DNA polymerases such as Klenow and Taq DNA polymerases. For example, the use of manganese in place of, or in addition to, magnesium in the reaction mixture may reduce or eliminate discrimination against dideoxynucleotides. Under such conditions, T7 DNA polymerase does not differentiate between the two molecules whereas other DNA polymerases such as Klenow fragment, Taq and Vent still discriminate to some degree. For example, Klenow still discriminates against ddNTPs by as much as four-fold in the presence of manganese. More important, even though the overall degree of discrimination by such enzymes as Klenow and Taq DNA polymerases is reduced, the intensity of specific fragments can vary by much more than four fold due to high discrimination at certain sequences in DNA. These polymerases and procedures are now almost universally used in manual DNA sequencing (i.e., without aid of sequencing machines such as described above) and are extensively used in automated methods. The use of manganese and the lack of discrimination against ddNTPs at all sites results in bands of uniform intensities, thus facilitating the reading of sequencing gels, either by manual or automated procedures. Moreover, the lack of discrimination enables the use of novel procedures for sequence analysis (Tabor and Richardson, supra). A method based on this finding is provided to determine a DNA sequence in a single reaction that contains all four ddNTPs at different ratios, by measuring the relative intensity of each peak after gel electrophoresis. The authors indicate:

> The DNA polymerases of this invention do not discriminate significantly between dideoxy-nucleotide analogs and normal nucleotides. That is, the chance of incorporation of an analog is approximately the same as that of a normal nucleotide or at least incorporates the analog with at least $\frac{1}{10}$ the efficiency that of a normal analog. The polymerases of this invention also do not discriminate significantly against some other analogs. This is important since, in addition to the four normal deoxynucleoside triphosphates (dGTP, dATP, dTTP and dCTP), sequencing reactions require the incorporation of other types of nucleotide derivatives such as: radioactively- or fluorescently-labelled nucleoside triphosphates, usually for labeling the synthesized strands with $^{35}S$, $^{32}P$, or other chemical agents. When a DNA polymerase does not discriminate against analogs the same probability will exist for the incorporation of an analog as for a normal nucleotide. For labelled nucleoside triphosphates this is important in order to efficiently label the synthesized DNA strands using a minimum of radioactivity.

They also state:

> The ability to produce nearby bands of approximately the same intensity is useful since it permits the results of any sequencing reaction to be read more easily and with greater certainty. Further, since the DNA products from a sequencing reaction with a specific chain terminating agent form bands which are of approximately the same intensity as that of nearby bands, band intensity itself provides a specific label for the series of bands so formed. The number of DNA products of approximately the same molecular weight produced by a given chain terminating agent varies depending upon the concentration of the chain terminating agent. Thus, by using a different concentration of each of the four chain terminating agents for the synthesis the DNA products incorporating one chain terminating agent are distinguished from DNA products of approximately the same molecular weight incorporating other chain terminating agents in that they differ in number or amount; consequently, the bands of DNA products can be identified as to chain terminating agent simply by their intensity as compared to the intensities of nearby bands. As a result, two or more series of DNA products, each series having a different chain terminating agent, can be subjected to gel permeation in a single lane and identified, i.e., distinguished from each other, by the intensity of each band as compared to the intensity of nearby bands. Moreover, the syntheses of DNA products incorporating different chain terminating agents need not be carried out separately, in separate containers, but may all be carried out simultaneously in a single reaction vessel, and the same label, e.g., radioisotopic, fluorescent, etc. can, if desired, be used for all chain terminating agents instead of a different label for each, thus simplifying the procedure.

See also Tabor and Richardson Proc. Natl. Acad. Sci. USA 86, 4076–4080 (1989) which indicates that substitution of manganese ions for magnesium ions for catalysis by T7 DNA polymerase or E. coli DNA polymerase reduces the discrimination of these polymerases for ddNTPs by 4–100 fold, and Tabor and Richardson J. Biol. Chem. 265, 8322–8328 (1990) which describes the use of pyrophosphatase and manganese ions to generate dideoxy-terminated fragments of uniform intensity using T7 DNA polymerase.

SUMMARY OF THE INVENTION

Applicant believes that the lesser utility of some DNA polymerases for dideoxy DNA sequencing is due in part to the reduced ability of those polymerases to incorporate a ddNMP (or other nucleotide analog) in place of a dNMP. As noted above, the ability not to discriminate allows use of lower concentrations of ddNTPs than with enzymes that do discriminate, and most important it provides banding patterns in sequencing gels that are of more uniform intensity along their length. Both these results make automated sequencing with the enzyme easier and more profitable in that longer DNA sequences can be determined with greater confidence.

The present invention provides a method by which an otherwise discriminatory DNA polymerase can be altered to discriminate less against ddNTPs than the corresponding naturally occurring enzyme. This method involves the modification of the polymerase genetically to provide amino acid residues at key locations that enhance the ability of the polymerase to incorporate analogs of dNMPs. Applicant has determined that amino acid changes in a specific region of DNA polymerases have a dramatic effect on the ability of those DNA polymerases to incorporate dideoxynucleotides; the specific amino acid residue inserted determines whether the polymerase is more or less discriminatory towards ddNTPs. Applicant has determined that modifying DNA polymerases so that they incorporate dideoxynucleotides more efficiently has a tremendous effect on their utility in DNA sequencing. It is possible that such modified DNA polymerases will also prove useful for other common molecular biology procedures such as the amplification of DNA (for example by the polymerase chain reaction), in vitro mutagenesis and filling in the ends of DNA fragments. The combination of this technology with existing knowledge for alteration of 3'-5' exonuclease activity of a DNA polymerase (such as T7 DNA polymerase as described by Tabor and Richardson, supra), and the use of manganese and pyrophosphatase in sequencing reactions will allow the production of significantly superior enzymes to those presently known.

In one particular aspect, namely, DNA sequencing, thermophilic enzymes having an ability to catalyze the polymerization of nucleotides at temperatures above 50° C. and, in particular, above 60° C., 70° C., or even 80° C., under conditions used for DNA sequencing, are well known in the art. Such enzymes are generally present in organisms that grow at these temperatures. However, applicant believes that many of these enzymes suffer from limitations, including the limited ability to incorporate dideoxynucleotides. By modification of these enzymes using methods shown below, those in the art can now modify any desired thermophilic DNA polymerase to make it incorporate dideoxynucleotides more efficiently. Such enzymes will be superior to those existing in the present day for DNA sequencing both in automated machines and in manual sequencing, especially in procedures known as cycle sequencing. In cycle sequencing, multiple rounds of DNA synthesis are carried out from the same template, with the synthesized strand removed after each cycle by heat denaturation; this allows much smaller amounts of DNA template to be used in a sequencing reaction Applicant has determined experimentally that amino acid residue 526 in the relatively non-discriminating enzyme T7 DNA polymerase provides it with this property. Applicant has determined that by modification of residue 526 it is possible to increase the ability of T7 DNA polymerase to discriminate many fold. Based on the amino acid homologies between T7 DNA polymerase and other DNA polymerases, applicant has determined that altering the residue at the homologous site in other DNA polymerases likewise affects their ability to discriminate against dideoxnucleotides. Examples of such homologous sites are residue 762 of *E. coli* DNA polymerase I and residue 667 of Taq DNA polymerase. In all three of these examples, applicant has shown that it is important that the residue at this site is different from phenylalanine (F), e.g., it may be tyrosine (Y) as in T7 DNA polymerase. Surprisingly, modification of this single amino acid residue, even by the addition of a single hydroxyl group, provides a very large alteration (250–8,000 fold) in discrimination levels. Those in the art will recognize that changes at this one site are not limiting in this invention, and changes at other sites that decrease the ability of a polymerase to discriminate can now be readily found by routine experimentation. For example, applicant has found that modification of T7 DNA polymerase at 13 other sites also results in an increased ability of the enzyme to discriminate against ddNTPs, however the effect of alterations at these sites is much less, only 5–20 fold. By use of analogous procedures, other sites that effect discrimination against ddNTPs can be readily identified in other DNA polymerase to make them more useful for DNA sequencing. Such other sites include amino acid residues in regions highly homologous between *E. coli* DNA polymerase I and T7 DNA polymerase, since these regions are likely to make up in part the binding domain for ddNTPs; in *E. coli* DNA polymerase I, these regions include amino acids in regions analogous to those in T7 DNA polymerase from conserved or non-conserved amino acids in regions 665–681 and 754–783, and possibly in regions 709–734, 797–866, and 913–927. The amino acid change to provide the desired function can be chosen to be identical to corresponding amino acids of a non-discriminatory enzyme like T7 DNA polymerase, or other functionally equivalent amino acids which can be chosen by routine experimentation. By changing non-conserved amino acids more profound alteration of the ability to discrimination is obtained. Non-conserved amino acids are those which vary from one species of polymerase to another (i.e., are found in less than 50% of polymerases). The term "analogous" is used in its commonly recognized manner. Thus, an analogue of a Pol I polymerase is one having an amino acid sequence as described by Braithwaite and Ito, infra, which is preferably as related to the other members of the Pol I family of polymerases described therein as is Spo2 DNA polymerase. Such analyses can be performed using Felsenstein's PHYLIP program. Id.

Thus, in a first aspect the invention features a modified gene encoding a modified DNA polymerase. The gene is modified to produce a modified DNA polymerase that, compared to the corresponding naturally-occurring or unmodified DNA polymerase, has an increased ability to incorporate a dideoxynucleotide compared to a deoxynucleotide.

By "increased ability" is meant that the DNA polymerase is able to better incorporate a dideoxynucleotide. That is, it discriminates to a lesser extent than a corresponding naturally-occurring DNA polymerase against a dideoxynucleotide compared to a deoxynucleotide. Specific methods for measuring such discrimination are provided below. The term "increased" means to provide a measurable difference in ability to incorporate such dideoxynucleotides. In preferred embodiments, this is a increase of at least 10% compared to the naturally-occurring enzyme, although it is preferred that the level of discrimination against a dideoxynucleotide is reduced by at least 10 to 100 fold and preferably by 100–500 fold. One example of such an enzyme is *E. coli* DNA polymerase I which (as noted herein) discriminates approximately 140–1,100 fold against incorporation of dideoxynucleotides compared to deoxynucleotides. By the method of this invention an enzyme can be derived (by alteration of only one or two amino acids) that actually prefers ddNTPs over dNTPS—that is, the ability of the polymerase to incorporate dideoxynucleotides has been increased by an average of 1,000 fold.

The phrase "corresponding naturally-occurring DNA polymerase" is one well known in the art and refers to the polymerase found in nature, and which preferably is not altered either by in vitro or in vivo manipulations in the laboratory. Similarly the corresponding nucleic acid is that nucleic acid encoding a DNA polymerase found in nature. This is simply used as a base line to compare modified nucleic acids encoding such polymerases. Thus, a base line for the DNA polymerase of *Thermus aquaticus* (also termed "Taq") is the nucleic acid which naturally encodes Taq DNA polymerase present in the bacterium *Thermus aquaticus*. Applicant provides at least one site which can be changed in such polymerases to alter the ability of the polymerase to incorporate a dideoxynucleotide. These sites are merely examples and are not limiting in this invention since those in the art armed with the knowledge that the ability of a DNA polymerase can be usefully altered in this property are now provided with the methodology by which to alter such enzymes either at these specific sites or at other equivalent sites.

DNA polymerases of this invention may also be modified to remove or alter an exonuclease domain, such as the 3'–5' exonuclease activity described by Tabor and Richardson, supra, or the 5'–3' exonuclease activity in Taq described by Barnes (WO 92/06188). The mutations that alter the ability of DNA polymerases of this invention to discriminate against ddNTPs preferably do not affect the exonuclease activity substantially; by this it is meant that the mutations are in the polymerase domain of the enzyme, near the active site for polymerization, and are not decreasing discrimination merely by reducing the ability of the polymerase to remove incorporated analogs via its exonuclease activity. Particularly suitable DNA polymerases of this invention are Pol I-type polymerases as described by Braithwaite and Ito, 21 *Nuc. Acid. Res.* 787, 1993, hereby incorporated by reference herein, and referred to as Family A, and polymerase alpha or polymerase II-type DNA polymerases described by Braithwaite and Ito, and referred to as family B. The other polymerase families described by Braithwaite and Ito may also be used in this invention. In particular, applicant has found that the presence of a polar, hydroxyl containing amino acid residue at a position near the binding site for the dNTP substrate is important for the polymerase being able to efficiently incorporate a dideoxynucleotide. Without being bound by any theory, Applicant believes that this finding is contrary to the expected result that high discrimination against a nucleotide without a hydroxyl group at the 3' position of the ribose moiety (i.e. a ddNTP) requires the simultaneous absence of a hydroxyl group on the amino acid residue at this critical site. In other words, the presence of the gap, or hole created by the absence of both hydroxyl groups leads to discrimination against the analog. Knowledge of this result provides an approach to finding the critical residue in even distantly related DNA polymerases; the addition of a residue with a polar group for a non polar one in the region where the dNTP binds is a useful candidate amino acid change for decreasing the ability of the polymerase to discriminate against ddNTPs. For example, the phenylalanine at position 272 of rat DNA polymerase β, a DNA polymerase with little if any homology to polymerases of Family A or B, has been shown by X-ray diffraction studies to be in contact with the 3' position of the ddCTP residue in a ternary complex with a primer-template (Pelletier et al., 264 *Science* 189, 1994). Knowledge of the results described in this invention make the modification of this residue to tyrosine a logical choice in a screen of mutants of rat DNA polymerase β that incorporate dideoxynucleotides more efficiently. Those in the art will thus be likely to be able to alter the discriminatory phenotype of any DNA polymerase using the information provided herein.

The ability of some polymerases of this invention to incorporate dideoxynucleotides more efficiently can be specific (i.e., the effect on dideoxynucleotide analogs is much greater than on other analogs). However, some of the polymerases are also useful to aid in incorporation of other base modified analogs (e.g., deoxyinosine triphosphate (dITP) and 2'-deoxy-7-deazaguanosine 5'-triphosphate ($dc^7GTP$) to remove compression of bands during electrophoresis, and fluorescently labeled deoxynucleotides or dideoxynucleotides for use in automated procedures). In addition, such polymerases may be able to incorporate ribonucleotides more efficiently thus allowing synthesis of RNA without need for a promoter. Specifically, the conserved motifs between single-subunit DNA-dependent RNA polymerases such as T7 RNA polymerase and DNA polymerases of Family A (Pol I-type DNA polymerase) suggest that mutations in this region (residues 758 to 767 of *E. coli* DNA polymerase I) are likely to change the specificity towards rNTPs. This permits the engineering of RNA polymerases that efficiently initiated synthesis from a primer, eliminating the requirement for a promoter for the synthesis of RNA. Analogously, the data provided herein suggest that modifying residues 631 to 640 of T7 RNA polymerase will alter its specificity towards dNTPs. This permits the engineering of a new DNA polymerase that initiates DNA synthesis de novo from a promoter sequence, and cannot use a primer.

In preferred embodiments, the modified DNA polymerase has sufficient DNA polymerase activity (e.g., at least that used in a standard sequencing reaction, and preferably at least 100 units/mg of enzyme as defined in the art; preferably the mutation in the polymerase does not alter the prior level by more than 5–10 fold) for use in DNA sequencing (when combined with any host factor necessary for that DNA polymerase activity); and has sufficiently low exonuclease activity (e.g., less than 500 units/mg, see Tabor and Richardson, supra) to allow the polymerase to be used in DNA sequencing; the DNA polymerase has one or more of the amino acids at the dideoxynucleotide binding site of a T7-type DNA polymerase (e.g., one selected from the group consisting of T7, T3, ØI, ØII H, W31, gh-1, Y, A1122, and SP6). Preferably the modified DNA polymerase is modified from a thermostable enzyme, such as the DNA polymerase encoded by *Thermus aquaticus, Thermus thermophilus, Thermus flavus, Bacillus sterothermophilus*, and Vent bacteria; and the ability of the polymerase to incorporate a dideoxynucleotide is increased at least 10-fold, 50-fold or most preferably at least 100-fold compared to the corresponding naturally-occurring DNA polymerase, e.g., by a change at just one amino acid.

In a second aspect, the invention features a method for production of a modified DNA polymerase having an increased ability to incorporate a dideoxynucleotide compared to the ability of a corresponding naturally-occurring DNA polymerase. The method includes providing a nucleic acid molecule encoding a DNA polymerase and mutagenizing or otherwise altering the nucleotide base sequence of the nucleic acid molecule to incorporate one or more base changes in the nucleotide base sequence at one or more sites which significantly (i.e., at least 10, 50 or most preferably 100–500 fold) alter the ability of the polymerase encoded by the nucleic acid to incorporate a dideoxynucleotide.

In a third aspect, the invention features a method for determining the nucleotide base sequence of a DNA molecule. The method includes providing a DNA molecule annealed with a primer molecule able to hybridize to the DNA molecule; and incubating the annealed molecules in a vessel containing at least one deoxynucleotide triphosphate, a DNA polymerase modified from a naturally-occurring DNA polymerase to have an increased ability to incorporate a dideoxynucleotide compared to the naturally-occurring polymerase. (The polymerase has sufficient DNA polymerase activity and sufficiently low exonuclease activity to be useful for DNA sequencing.) Also provided is at least one DNA synthesis terminating agent which terminates DNA synthesis at a specific nucleotide base. The method further includes separating the DNA products of the incubating reaction according to size, whereby at least a part of the nucleotide base sequence of the DNA molecule can be determined.

In preferred embodiments, the DNA polymerase is a thermostable DNA polymerase and the sequencing is performed at a temperature above 50° C., 60° C., or 70° C., and the DNA polymerase is derived (i.e., has at least 50% identity in amino acid residues) from one encoded by *Thermus aquaticus*, *Thermus thermophilus*, *Thermus flavus*, *Bacillus sterothermophilus*, *Thermococcus litoralis* (Vent), *Pyrococcus furiosus* (Pfu) or *Sulfolobus solfataricus*.

In other preferred embodiments, the DNA polymerase has less than 1000, 250, 100, 50, 10 or even 2 units of exonuclease activity per mg of polymerase and is able to utilize primers having only 4, 6 or 10 bases; and the concentration of all four deoxynucleoside triphosphates at the start of the incubating step is sufficient to allow DNA synthesis to continue until terminated by the agent, e.g., a ddNTP.

For cycle sequencing, the polymerases of the present invention now make it possible to use significantly lower amounts of dideoxynucleotides compared to other enzymes. That is, the method involves providing an excess amount of deoxynucleotides to all four dideoxynucleotides in a cycle sequencing reaction, and performing the cycle sequencing reaction. For other enzymes, it was necassary to add an excess of at least one of the ddNTPs to such reactions. For example, Sears et al., 13 *BioTechniques* 626, 1992 describe use of about a 10 fold excess of ddNTPs to dNTPs with Vent polymerase, and Carothers et al., 7 *BioTechniques* 494, 1989 describe use of at least 2 fold excess of ddNTPs to dNTPs for Taq polymerase. In the present invention, such excess is not needed. Preferably, more than 2, 5, or even 10 fold excess of a dNTP is provided to the corresponding ddNTP. In a specific example, less than 10 μM ddNTP is used with a modified Taq of this invention.

In a related aspect, the invention features a kit or solution for DNA sequencing including a modified DNA polymerase as described above and a reagent necessary for the sequencing selected from the group consisting of dITP, deaza GTP, a chain terminating agent such as a ddNTP, and a manganese-containing solution or powder.

In another aspect, the invention features a method for providing a modified DNA polymerase having an increased ability compared to the corresponding naturally-occurring DNA polymerase to incorporate a dideoxynucleotide by providing a nucleic acid sequence encoding the modified DNA polymerase, expressing the nucleic acid within a host cell, and purifying the DNA polymerase from the host cell.

In another related aspect, the invention features a method for sequencing a strand of DNA essentially as described above with one or more (preferably 2, 3 or 4) deoxyribonucleoside triphosphates, a DNA polymerase as described above, and a first chain terminating agent. The DNA polymerase causes the primer to be elongated to form a first series of first DNA products differing in the length of the elongated primer, each first DNA product having a chain terminating agent at its elongated end, and the number of molecules of each first DNA products being approximately the same for substantially all DNA products differing in length by no more than 20 bases. The method also features providing a second chain terminating agent in the hybridized mixture at a concentration different from the first chain terminating agent, wherein the DNA polymerase causes production of a second series of second DNA products differing in the length of the elongated primer, with each second DNA product having the second chain terminating agent at its elongated end. The number of molecules of each second DNA product is approximately the same for substantially all second DNA products differing in length from each other by from 1 to 20 bases, and is distinctly different from the number of molecules of all the first DNA products having a length differing by no more than 20 bases from that of said second DNA products.

In preferred embodiments, three or four such chain terminating agents can be used to make different products as described in Tabor and Richardson, supra; and the sequencing reaction is provided with a magnesium ion, or even a manganese or iron ion (e.g., at a concentration between 0.05 and 100 mM, preferably between 1 and 10 mM); and the DNA products are separated according to molecular weight in less than four lanes of a gel.

In another related aspect, the invention features a method for sequencing a nucleic acid by combining an oligonucleotide primer, a nucleic acid to be sequenced, between one and four deoxyribonucleoside triphosphates, a polymerase as described above, and at least two chain terminating agents in different amounts, under conditions favoring extension of the oligonucleotide primer to form nucleic acid fragments complementary to the nucleic acid to be sequenced. The method further includes separating the nucleic acid fragments by size and determining the nucleic acid sequence. The agents are differentiated from each other by intensity of a label in the primer extension products.

While it is common to use gel electrophoresis to separate DNA products of a DNA sequencing reaction, those in the art will recognize that other methods may also be used. Thus, it is possible to detect each of the different fragments using procedures such as time of flight mass spectrometry, electron microscopy, and single molecule detection methods.

The invention also features an automated DNA sequencing apparatus having a reactor including reagents which provide at least two series of DNA products formed from a single primer and a DNA strand. Each DNA product of a series differs in molecular weight and has a chain terminating agent at one end. The reagents include a DNA polymerase as described above. The apparatus includes a separating means for separating the DNA product along one axis of the separator to form a series of bands. It also includes a band reading means for determining the position and intensity of each band after separation along the axis, and a computing means that determines the DNA sequence of the DNA strand solely from the position and intensity of the bands along the axis and not from the wavelength of emission of light from any label that may be present in the separating means.

In other aspects, the invention features: (a) a method for in vitro mutagenesis of a cloned DNA fragment by providing the cloned fragment and a DNA polymerase described above, contacting the cloned fragment with the polymerase under conditions for synthesizing a DNA strand from the fragment. The conditions cause formation of the DNA strand by incorporation of a plurality of individual contiguous bases able to base-pair with the fragment and incorporation of a nucleotide base unable to base pair with the fragment; (b) a method for in vitro mutagenesis of a template DNA fragment by providing a primer and template, the primer having contiguous bases able to base-pair with contiguous bases of the template, except at least one base which is unable to base-pair with the template. The method involves extending the primer with a DNA polymerase as described above; (c) a method for producing blunt-ended double-stranded DNA from a linear DNA molecule having a 5' end having a single-stranded region. The 3' end of the molecule is double-stranded and has no 3' protruding termini. The method includes incubating the DNA molecule with a DNA polymerase as described above which acts on the single-stranded region to produce a blunt-ended double-stranded DNA molecule; (d) a method for labeling the 3' end of a DNA fragment by incubating the DNA fragment with a DNA polymerase as described above, and a labelled deoxynucleotide species under conditions in which the 3' end of the DNA fragment is extended by the polymerase and thereby labelled by addition of the labelled deoxynucleotide to the DNA fragment; (e) a method of amplification of a DNA sequence by annealing a first and second primer to opposite strands of a double-stranded DNA sequence and incubating the annealed mixture with a DNA polymerase as described above. The first and second primers anneal to opposite strands of the DNA sequence with their 3' ends directed towards each other after annealing, and with the DNA sequence to be amplified located between the two annealed primers.

In yet other aspects, the invention features specific DNA polymerases, such as *Thermus aquaticus* DNA polymerase having a tyrosine at residue 667, *E. coli* DNA polymerase I having a tyrosine at residue 762, and any Pol I type DNA polymerases having a tyrosine residue at the analogous location to *E. coli* DNA polymerase residue 762, e.g., at the $N_4$ position of the amino acid sequence K $N_1$ $N_2$ $N_3$ $N_4$ $N_5$ $N_6$ $N_7$ Y G, wherein each N is independently any amino acid. Furthermore, this invention features specific polymerases of the DNA polymerase alpha family having the sequence K $N_1$ $N_2$ $N_3$ $N_4$ $N_5$ $N_6$ Y G/Q, wherein each N is independently any amino acid, and where one of the residues $N_1$ to $N_7$ has been mutated to produce a polymerase that has reduced discrimination against ddNTPs (preferably reduced by at least 20-fold compared to the non-mutated sequence). The invention also features nucleic acid encoding any of these DNA polymerases.

In related aspects, the invention features DNA polymerases except reverse transcriptase which in the presence of magnesium as the only added divalent cation have an average processivity of less than 100 and discriminate less than 100 times against incorporation of a ddNMP compared to a dNMP, or which in the presence of magnesium as the only added divalent cation have an average processivity of less than 50 and discriminate less than 50 or 5 times against incorporation of a ddNMP compared to a dNMP. Those in the art will recognize that processivity can be measured by any standard procedure that will indicate that the average processivity of T7 DNA polymerase is at least 500, that of Klenow fragment is about 4–40, and for reverse transcriptase it is about 150–200. Such measurements can be performed as described by Tabor et al., *J. Biol. Chem.* 262: 16212, 1987, hereby incorporated by reference herein. The average processivity of Taq DNA polymerase under these conditions is expected to be less than 100.

In particularly preferred aspects, the invention features thermophilic DNA polymerases that discriminate, e.g., in the presence of magnesium, against a ddNMP compared to a dNMP by less than a factor of 100, and which preferably have an average processivity less than 100, and cycle from one primer-template to another more than once per one or even ten seconds. Such cycling can be measured by standard procedures.

The invention also features a method for cycle sequencing using a DNA polymerase as described above, and also features cellular (as opposed to viral or mitochondrial) DNA polymerases having a tyrosine in place of the naturally occurring amino acid at a location which causes the polymerase not to discriminate against a ddNMP compared to a dNMP by more than 50 fold.

In other aspects, substitution of the amino acid at the noted sites will result in alteration of other properties of the corresponding natural polymerase. In addition, polymerases of this invention may be combined with other polymerases in the methods described herein to take advantage of the superior properties of each polymerase in the mixture.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a diagrammatic representation of the amino acid sequence of the DNA polymerase encoded by gene 5 of bacteriophage T7 indicating the palm and finger domains, and the location of various dideoxy resistant (DR) mutants, the location of regions labelled A–E, and the location of one site involved in ddNTP discrimination;

Figure 4:
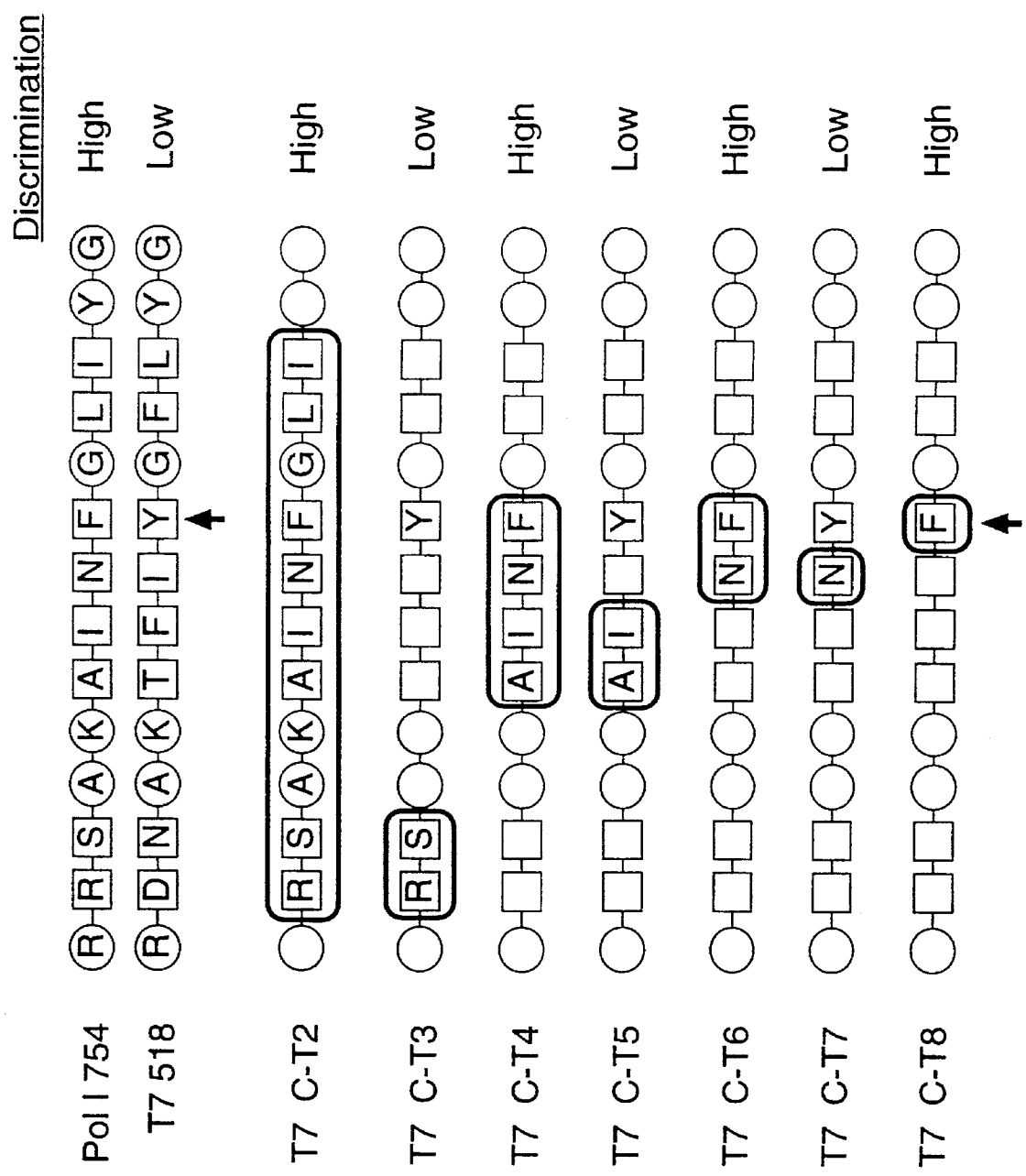
Figure 5:
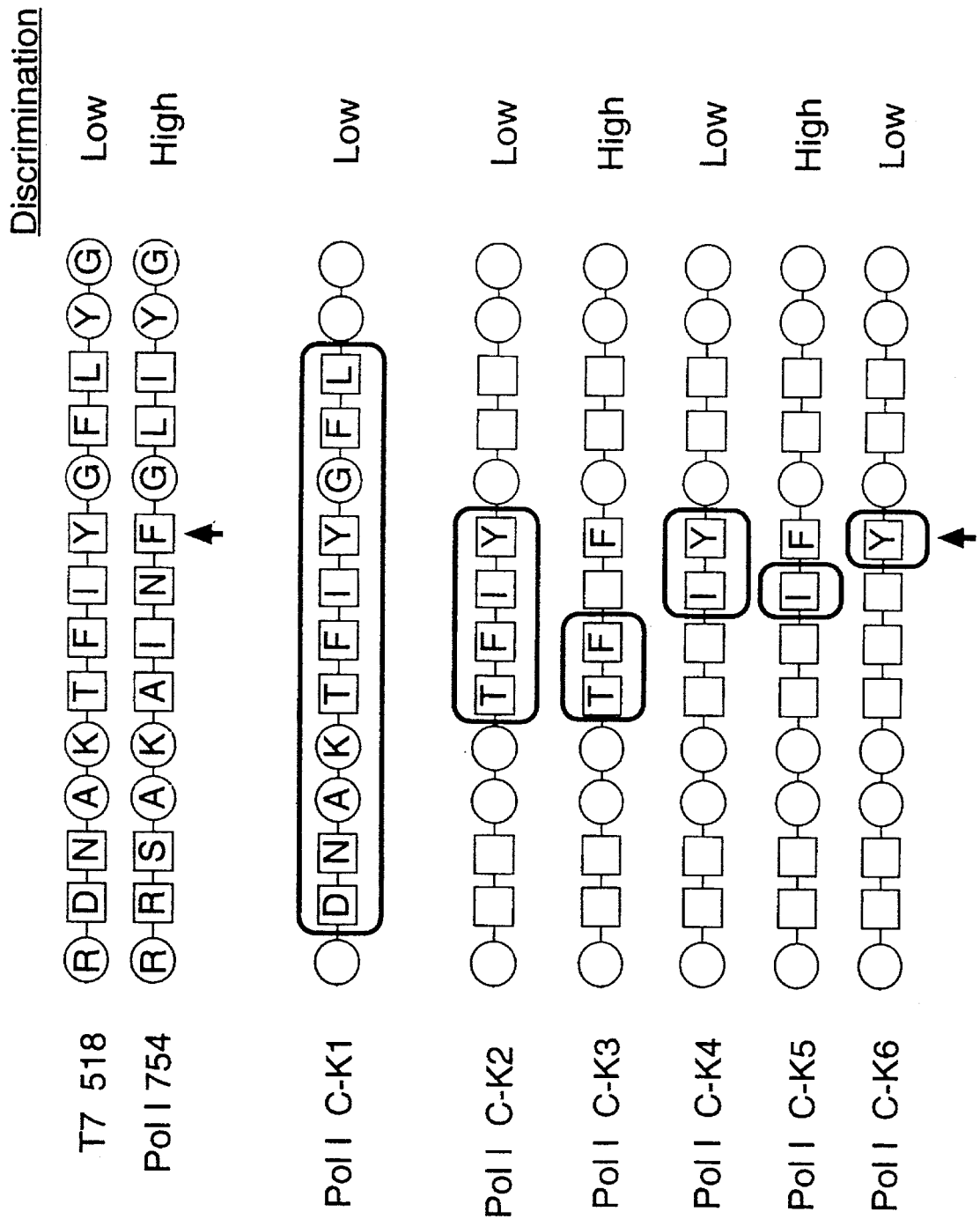
Figure 6:
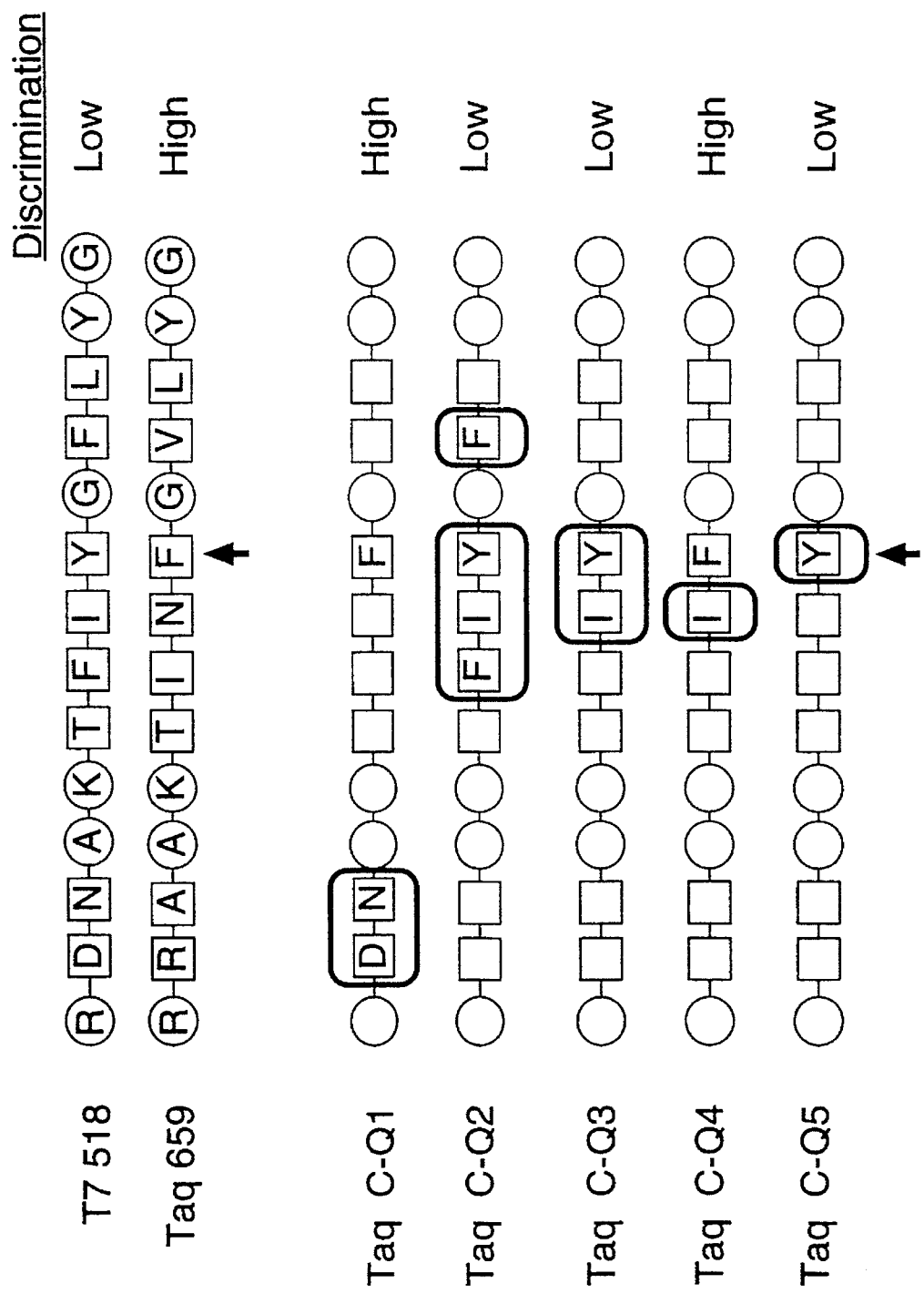

FIGS. 4, 5, and 6 are diagrammatic representations showing modifications of the riboselectivity region of *E. coli* DNA polymerase I, T7 DNA polymerase, and Taq DNA polymerase, respectively.

Dideoxy Resistant Mutants

The following is a brief discussion of publications of some relevance. None are admitted to be prior art to the pending claims but are provided to aid in understanding the present invention.

Reha-Krantz et al., Mutational Analysis of Bacteriophage T4 DNA Polymerase, from Abstracts for Poster Presentations, presented at a meeting entitled "The Fidelity of DNA Synthesis: Structural and Mechanistic Perspectives, Beaufort, N.C., Sep. 24–29, 1989 describe C-terminal mutants with increased utilization of ddNTPs. However, Reha-Krantz et al., *J. Virology* 67, 60–66 (1993), indicate that while the Ki for ddGTP was 50 times lower with the mutant L412M compared to wild-type T4 DNA polymerase, no difference in efficiency of incorporation of ddGTP was found between the mutant and wild-type T4 DNA polymerase. On page 63, it states that "Despite the sensitivity of the L412M DNA polymerase to ddGTP, there was no difference found in the incorporation of ddNTPs by wild-type and L412M DNA polymerases". It also states "it does not appear that any single region is the sole binding site for either PPi or nucleotides". In addition, Reha-Krantz and Nonay, *J. Biol. Chem.* 269, 5635–5643 (1994), provide a study of the mutant L412M and other mutant T4 DNA polymerases.

Gibbs et al., *Proc. Natl. Acad. Sci. USA* 85, 6672–6676 (1988) and Larder et al., the *EMBO Journal* 6, 169–175 (1987) describe the spectrum of mutations obtained in Herpes DNA polymerase when selected for resistance to a number of nucleotide analogs: pyrophosphate, phosphonoacetic acid, and phosphonoformic acid, acyclovir, vidarabine, ganciclovir and bromovinyldeoxyuridine. It indicates that many of the mutants resistant to one drug are also resistant to other drugs, even when they are analogs to different regions of the substrate.

Derse et al., *J. Biol. Chem.* 257, 10251–10260 (1982), describe five classes of mutants in Herpes Simplex DNA polymerase isolated by selection for growth in the presence of phosphonoformic acid, a pyrophosphate inhibitor. For mutants in each class, they compare resistance to ddGTP (page 10256, Table III). All increase the Ki for ddGTP by 20 to 100 fold.

Prasad et al., *Proc. Natl. Acad. Sci. USA* 88, 11363–11367 (1991) use a direct screening strategy and show that a single mutation in HIV reverse transcriptase (a change of Glu 89 to Glycine) renders the polymerase more resistant to ddGTP (requires about 10 times more ddGTP to obtain same extent of inhibition). This mutation confers a broad resistance to a number of analogs, including phosphonoformic acid, a pyrophosphate analog. While the mutant was equally resistant to ddTTP, ddCTP and ddGTP, it was much less resistant to ddATP.

Song et al., *J. Virol.* 66, 7568–7571 (1992) mutate glu-89 of human immunodeficiency virus type 1 reverse transcriptase to 9 different amino acid residues, and measure the resistance of each mutant enzyme to ddGTP and phosphonoformic acid, a pyrophosphate analog. The mutations fell into two classes; replacement of Glu-89 with alanine, glycine, valine or threonine resulted in enzymes highly resistant to both ddGTP and phosphonoformic acid compared to the wild-type enzyme, while mutation to serine, glutamine, asparagine, aspartic acid, and lysine resulted in enzymes with only moderate or no resistance to ddGTP. None of the routants made the enzyme less resistant to ddGTP than the wild-type enzyme (Table I, page 7569). The authors speculate that the 89th and 90th residues of reverse transcriptase form a portion of the dNTP-binding pocket based on their results and the crystal structure of reverse transcriptase.

Papers concerned with the properties of *E. coli* DNA polymerase I mutant proteins with mutations in the vicinity of the mutation that result in ddNTP selectivity including the following:

Carroll et al., *Biochemistry* 30, 804–813 (1991) study two mutants: Tyr766Ser and Tyr766Phe for misincorporation of normal deoxynucleotides. Polesky et al., *J. Biol.Chem.* 265, 14579–14591 (1990), characterizes mutations that have two different properties: (1) Tyrosine 766, arginine 841, and asparagine 845; which the authors suggest that these residues contact the incoming dNTP. (2) Glutamine 849, arginine 668, and aspartic acid 882, which the authors suggest are involved in catalysis. Polesky et al., *J. Biol. Chem.* 267:8417 (1992), further characterizes mutations in arginine 668, glutamine 849, and aspartic acid 882, and also mutations at aspartic acid 705 and glutamic acid 710. In this study the authors look at the incorporation of alpha-thio-substituted dNTPs, i.e. analogs in the phosphate moiety. Pandey et al., *J. Biol.Chem.* 269, 13259–13265 (1994) look at two mutants in *E. coli* DNA polymerase I that change lysine 758 to alanine and arginine. The authors indicate that Basu et al., Biochemistry 26, 1704–1709 (1987) implicate the same lysine 758 in dNTP binding. This was shown chemically; DNA polymerase I was covalently modified using pyridoxal 5'-phosphate, a nucleotide analog, and lysine 758 was said to be the residue modified.

Beese et al., *Biochemistry* 321: 14095–14101 (1993) describe the structure of a cocrystal of Klenow fragment of DNA polymerase I complexed with a dNTP or with pyrophosphate. The authors state that the dNTP binds adjacent to helix O. The authors make the following statements: (a) "in the Mg-dCTP complex, cytosine interacts with His 881, while the sugar interacts with Phe 764 [sic., 762] (FIGS. 3 and 5)." (b) "However, we conclude that the position of at least the dNMP moiety of dNTP in the binary complex is not likely to be the same as in its catalytically relevant complex with primer-template DNA." (c) "Since the entire binding site for the base of dNTP is formed by its Watson-Crick hydrogen bonding to the template strand and its stacking on the 3' base of the primer strand, it is not unlikely that the binding site for the base in the binary complex is completely adventitious, consistent with our observation that it can bind in several locations dependent on conditions." (d) "The binding site for dNTP observed in crystals of the binary complex is the same as observed in solution studies. However, extrapolating from this binary complex to a model for the complex with dNTP in the presence of primer and template DNA requires considerable caution. We presume that the sugar and base moiety of the dNTP require primer-template DNA to bind in correct conformation."

Joyce and Steitz, 63 *Ann. Rev. Bioc.* 777, 1994 (not admitted to be prior art to the present invention) discuss the relationship of various DNA and RNA polymerases. It indicates three functions for the "palm" (rather than the "finger") subdomain of DNA polymerase I—namely, the catalytic center, the binding site for the 3' terminus of the primer, and the dNTP binding site. In HIV-1 reverse transcriptase it indicates that mutations that influence binding of DNA polymerase inhibitors are around residues 67–70. It also states that "[a]lthough no useful conclusions could be drawn from the positions of the nucleotide base of sugar, it is possible that the crystalline binary complex may be informative in identifying contacts between Klenow fragment and the dNTP phosphate groups." In the preceding paragraph, it states "although a polymerase-dNTP binary complex can be formed, such a complex is not catalytically competent." It further indicates that data "would place the deoxyribose close to Phe 762" and that "Mutation of Tyr 766 [in Klenow fragment helix O], which is located in the fingers domain in the vicinity of the model-built template strand, affects the discrimination between deoxy and dideoxy nucleotide substrates . . . ." However, it also states "In Klenow fragment, mutations that have been found to affect the binding of dNTP in the ternary complex (as reflected in $K_{m(dNTP)}$) are located on one side of the polymerase cleft within or close to the fingers subdomain. Positions identified thus far encompass the N terminus of helix Q (Arg 841 and Asn 845), the exposed face of helix O (Tyr 766, Phe 762, and Arg 754), and neighboring residues closer to the catalytic center (Asp 705 and Glu 710) . . . . An advantage of the kinetic approach is that it probes the ternary complex; however, as discussed above, it is impossible, in the absence of other structural evidence, to distinguish direct effects from those mediated via template interactions. Moreover, the side chains listed above encompass an area much larger than the dNTP molecule and therefore cannot all be in direct contact with it. Since the region of Klenow fragment implicated by these studies is thought to make extensive contact with the template strand, a reasonable interpretation is that a subset of the residues mentioned above are in direct contact with the dNTP, while the remainder bind the template DNA."

Pelletier et al., 264 *Science* 1891, and Sawaya et al., 264 *Science* 1930, 1994 (not admitted to be prior art to the pending claims) in contrast, indicate that residues 271–274 in helices M–N of Polβ (which are analogous to helices J–K of Klenow) "perform a common function, nucleotide discrimination."

Sousa et al. 364 *Nature* 593, 1993 (not admitted to be prior art to the pending claims) describe the three dimensional structure of T7 RNA polymerase and its homology to *E. coli* DNA polymerase I. They state that their observations suggest the "C-terminal elements of KF [Klenow fragment] (β-strand 14 [residues 916 to 928] and the C terminal) contact the deoxyribose moiety of the dNTP during polymerization to discriminate between rNTP and dNTP substrates."

Figure 1:
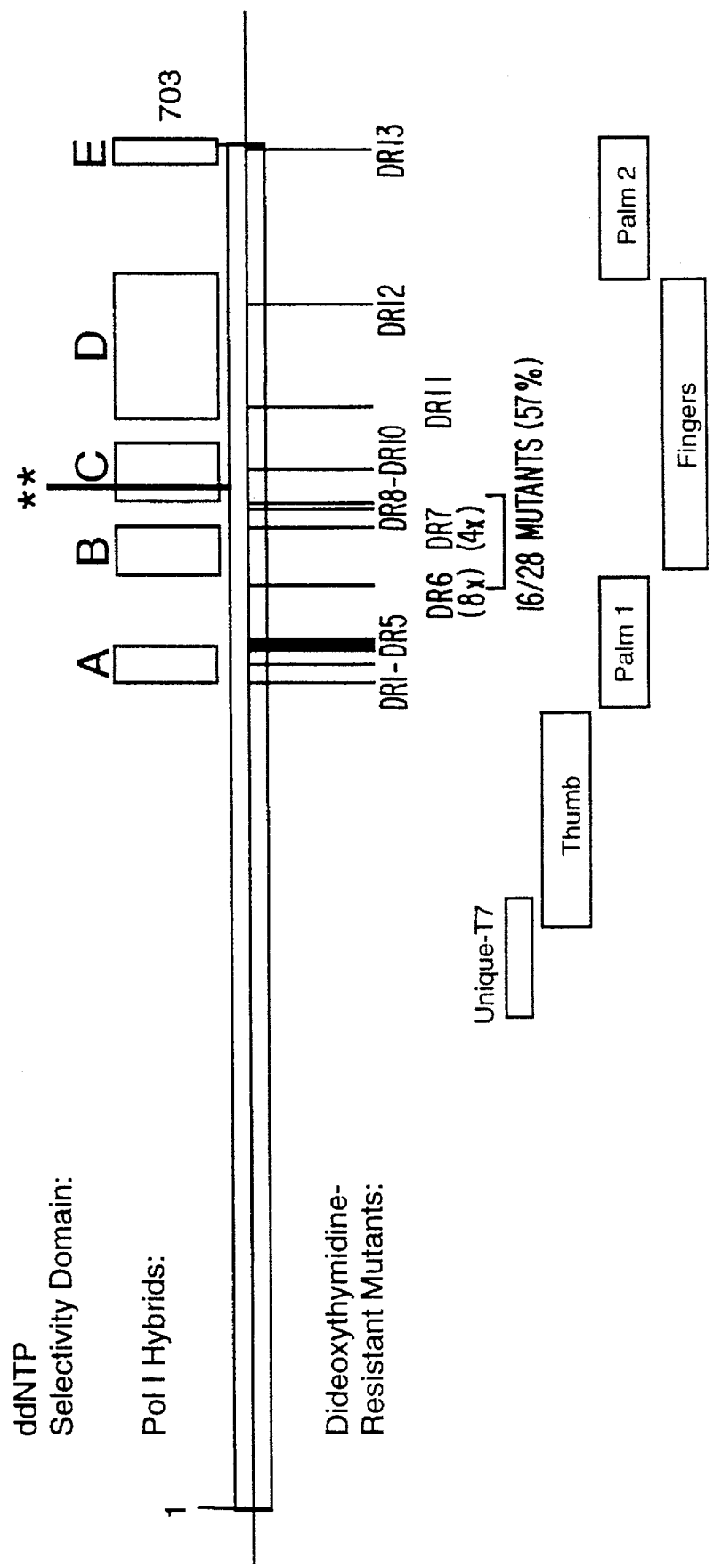

Dideoxynucleosides, such as dideoxythymidine, are potent inhibitors of T7 phage growth. Experiments indicate that the inhibition of DNA synthesis is a consequence of the incorporation of the dideoxynucleotide into T7 DNA. Dideoxynucleosides are not inhibitory to uninfected *E. coli*. We do not know the explanation for the lack of inhibition of *E. coli* DNA synthesis but it could be explained by cellular uptake, a high level of discrimination against their incorporation by *E. coli* DNA polymerase III, inefficient phosphorylation to a triphosphate, or efficient removal. In any case we find that T7 mutant phage arise that can yield normal plaques on agar plates containing dideoxynucleosides with a frequency of approximately $10^{-3}$. The location of many of these mutations are shown in FIG. 1. They reside within the gene 5 protein. The mutant gene 5 proteins are more discriminatory (by a few fold) against ddNTPs than the native gene 5 protein. Some members of this class of mutants may delineate the region of the polymerase that is important in recognition of the ribose moiety of the dNTP.

It is important to note that the mutations obtained by this selection using dideoxynucleosides are based on an alteration of the region of the gene 5 protein that recognizes the ribose moiety. However, it is possible that such mutations will also have dramatic effects on other nucleotide analogs. In addition, it is possible to use the same procedure to select for other T7 mutants that discriminate strongly against other nucleotide analogs on the basis of the growth of phage in the presence of the other analogs.

Referring to Table I, various DR mutants are indicated with the amino acid substitution noted in the table. The amino acid substitution is further characterized on the right hand side of the table. The location of these mutants is shown in FIG. 1 throughout the palm and finger regions of T7 DNA polymerase. These mutants are highly scattered throughout the polymerase and all have a relatively minor effect on incorporation of dideoxynucleotides, decreasing the ability to incorporate a dideoxynucleotide by only 5–20 fold. In addition, some of these mutants are located in regions of comparative non-homology to DNA polymerase I. Thus, they do not provide an indication of the location of sites in other Pol I enzymes involved in ddNTP discrimination.

In vitro Mutagenesis

Figure 2:
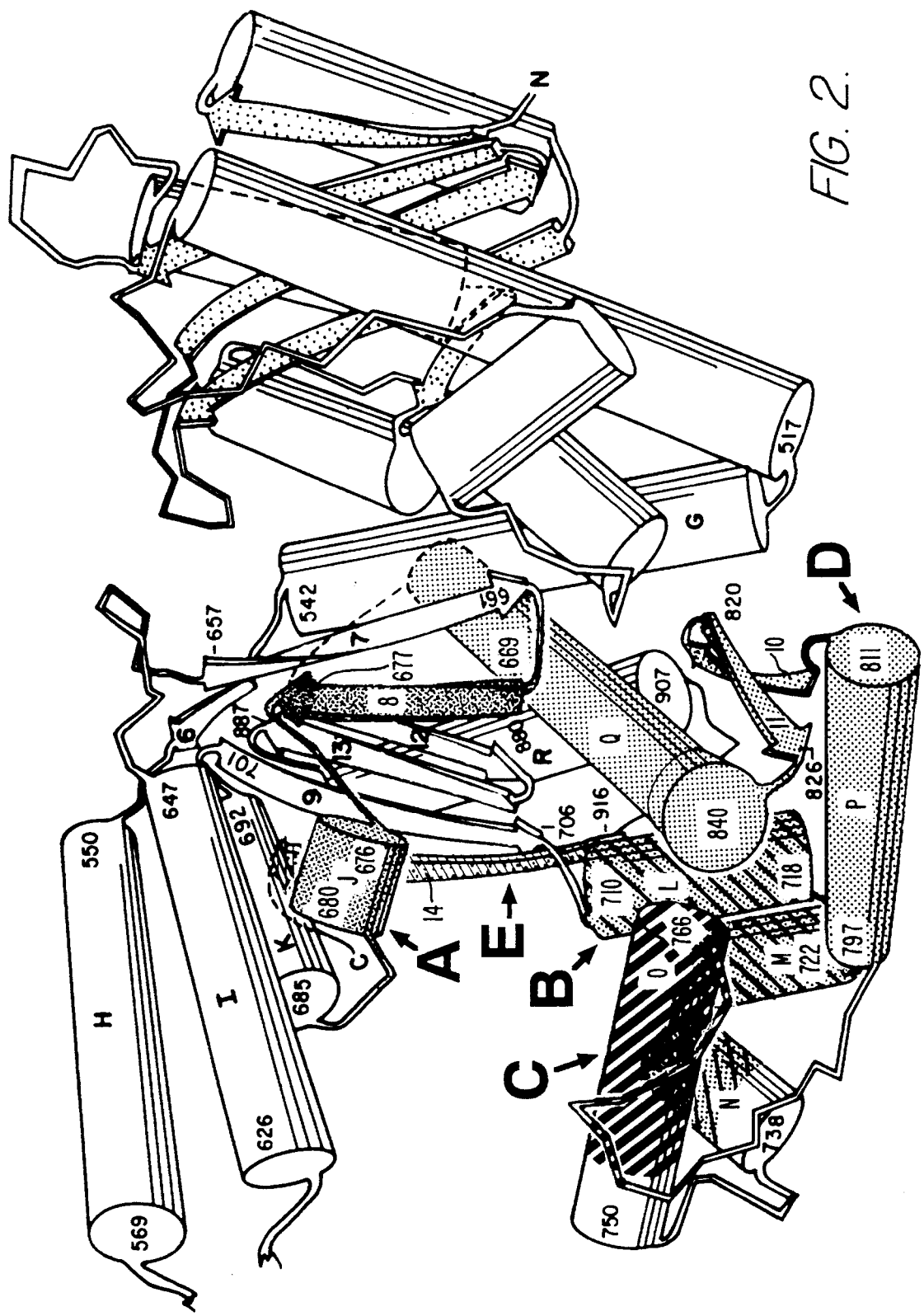
FIG. 2 is a three dimensional representation of the structure of DNA polymerase I showing the locations of regions A–E; numbers within the figure correspond to amino acid positions.

In vitro mutagenesis of the cloned gene 5 of T7 was used to construct gene 5 proteins in which different regions of *E. coli* DNA polymerase I were substituted for the analogous or homologous regions in T7 gene 5 protein. As discussed, we were particularly interested in determining the ability of these enzymes to incorporate nucleotide analogs and the extent to which they discriminate against these analogs. Referring to FIG. 2, the regions within which hybrids between T7 DNA polymerase and *E. coli* DNA polymerase I were made are shown as marked as regions A–E.

Figure 3:
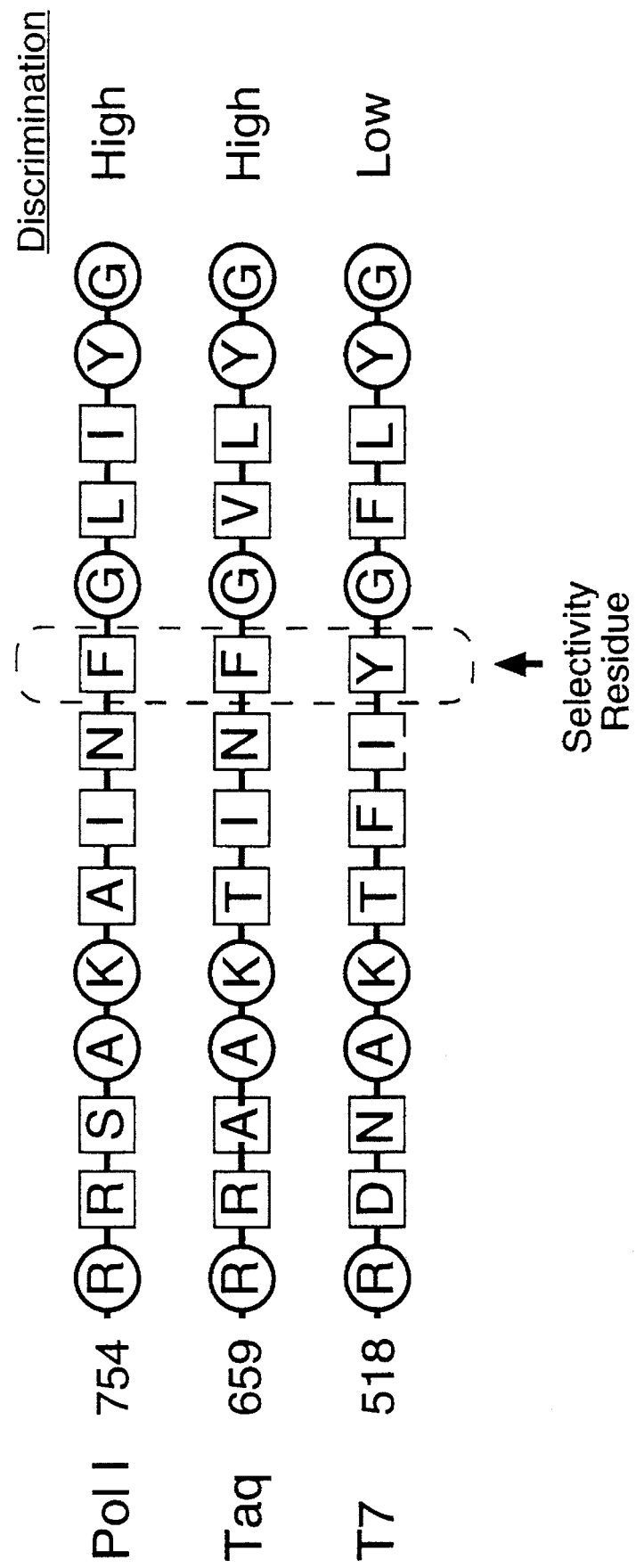
FIG. 3 is a diagrammatic representation of a riboselectivity region of pol I-type DNA polymerases with amino acids indicated by the universal single letter code. The initial amino acid number is indicated on the left of the figure and the amount of discrimination against dideoxynucleotides compared to deoxynucleotides is indicated on the right.

Referring to FIG. 3, Applicant has determined that region C provides a riboselectivity region having a significantly greater effect than other regions in the polymerase. Some of these other regions are specifically indicated in FIG. 3.

Referring to FIGS. 4–6 (and Table 2), it was determined that substitution of amino acids in this region allowed conversion of the riboselectivity of a polymerase from a *E. coli* DNA pol I-type to a T7 DNA polymerase type and vice versa. Thus, by targeted mutagenesis of this region of polI-type polymerases the riboselectivity of a polymerase can be significantly altered. The level of effect is at least 50–100 fold, and generally more than 500-fold.

DNA Polymerases

DNA polymerases useful in this invention include those belonging to the class of homologous polymerases termed "Pol I-type DNA polymerases" including T7-type DNA polymerases, the large fragment of *E. coli* DNA polymerase I, and Taq polymerase.

DNA polymerase useful in this invention include those belonging to a class of homologous polymerases including T7 type DNA polymerases (such as T7, T3, ØI, ØII, H W31, gh-1, Y, A1122, or SP6). By homologous polymerases is meant an enzyme such as those described by Delarue et al., *Protein Engineering* 3, 461–467 (1990), that presents an alignment of the Pol I family of DNA polymerases. It also presents the alignment of conserved sequence motifs from six families of polymerases: DNA polymerases from Pol I, Pol alpha, and Pol beta families, DNA-dependent RNA polymerases, reverse transcriptases, and RNA-dependent RNA polymerases; their results suggest a few residues are conserved between all polymerases. According to their alignment (FIG. 3, page 463), the selectivity residue identified herein (phenylalanine 762 in *E. coli* DNA polymerase I) is in "Motif B". In addition to the pol I family of DNA polymerases, Motif B is found in the pol alpha family of DNA polymerases and the T7 family of DNA-dependent RNA polymerases; thus this alignment strongly suggests the residues one should mutate in these other families of polymerases, that include T4 DNA polymerase, Herpes DNA polymerase, Ø29 DNA polymerase, Vent DNA polymerase and Pfu DNA polymerase.

In addition, Joyce, *Current Opinion in Structural Biology* 1, 123–129 (1991) compares the DNA sequences from many polymerases, and suggests that a small number of important active-site residues are conserved. In particular, there is a discussion of the similarities between polymerases of the pol I family (T7, pol I, Taq) and of the pol alpha family (T4, Ø29, Herpes). In FIG. 1 (page 124) Joyce indicates the positions of 5 invariant residues found in these two families; they include lysine 758, tyrosine 766, and glycine 767; these are all very close to the selectivity residue identified herein, phenylalanine 762.

These polymerases are used in a DNA sequencing reaction under conditions in which they preferably produce nearby bands of approximately uniform intensity (with about a 1.5- to 2.0-fold variation in intensity) when the DNA products of the sequencing reaction are run in a gel. By nearby is meant to include bands representing DNA products of molecular weight differing by as much as 6000, i.e., 20 bases. The actual value of this intensity will decrease along the length of the gel, as described in Tabor and Richardson, supra. Band intensity reflects the number of DNA products within a certain band. Labels such as fluorophores or radio-isotopes, are used to produce a readily detectable band of intensity reflective of the number of such DNA products. Thus, in this invention, nearby bands derived from one sequencing reaction with one chain terminating agent have approximately the same number of DNA products and thus a uniform band intensity. The sequencing conditions include incubation of the polymerase in the presence of specific divalent or trivalent cations such as manganese (II and III), ferrous and ferric ions; monovalent and divalent cations which have no detectable effect, or are detrimental to DNA synthesis, include: K, Na, Ba, Be, Ca, Cc, Cr, Co, Cu, Ni, Si and Zn. The anion is unimportant, for example, chloride, acetate, and sulfate are suitable. Under these conditions the requirement for chain terminating agents, such as dideoxynucleosides, may be lessened by several-fold for enzymes for this invention. A chelator may also be provided in this solution in order to help regulate the concentration of available divalent metal ions. For example, citrate or isocitrate may be provided. These chelates are thought to maintain the level of, for example, free manganese ions at a concentration of between 10 and 100 uM over a wide range of manganese concentrations. That is, the chelator acts as a buffer.

The DNA polymerases of this invention do not discriminate significantly between dideoxynucleotide analogs and deoxynucleotides along the length of the DNA template. That is, these polymerases are unable to discriminate significantly between a nucleotide that has a 3' hydroxyl group versus one that does not (i.e., has two hydrogens at the 3' position of the ribose). However, these polymerases may discriminate against modifications at other positions on the nucleosides, even in the presence of manganese or iron. For example, the polymerases may discriminate against some dideoxynucleotide analogs which have fluorescent groups attached compared to deoxynucleotides. However, the polymerases do not discriminate to a different extent at neighboring, or nearby nucleotides, on the basis of the presence or absence of the modification to the dideoxynucleotide. Thus, while they discriminate strongly against these analogs, requiring higher concentrations for a DNA sequencing reaction compared to unmodified dideoxynucleosides, the intensity of nearby bands will still be uniform.

Thus, the polymerases of this invention provide a uniform efficiency of incorporation of chain terminating agents, even if they discriminate against overall incorporation. In addition, other polymerases of this invention will give more uniform bands with fluorescent ddNTPs than the corresponding naturally occuring enzyme, although not as uniform as with unlabelled or radioactively labelled ddNTPs.

Chain terminating agents useful in this invention include dideoxynucleosides having a 2', 3'dideoxy structure. Other agents useful in the invention are those able to specifically terminate a DNA sequencing reaction at a specific base, and are not discriminated against by the polymerase under the above conditions.

In order to determine whether any particular DNA polymerase, in combination with any particular chain terminating agent, or other component of a sequencing reaction mixture, is useful in this invention, a standard sequencing reaction is performed, as described in Tabor and Richardson, supra, and the extent of band formation, and the uniformity of nearby bands in a sequencing gel, reviewed. If the polymerase reaction does not extend the primer by at least 20 bases, it is not suitable under the conditions used. Adjacent band uniformity within a two-fold or less range is useful in this invention, preferably the uniformity is within a 1.0–1.5 fold range. Similarly, determination of optimum cation concentration, or of other potential cations useful in the invention, is determined by use of this sequencing reaction under various conditions. For example, cations are tested in ranges from 0.005–100 mM. An example of such an experiment follows:

The ability to incorporate a given ddNMP compared to the corresponding dNMP for any one enzyme is measured as the ratio of ddNTP to dNTP necessary to allow DNA synthesis that terminates in a fixed range, detected as producing bands of no greater than a fixed molecular weight. That is, the bands produced in the reaction end within a specified range in the sequencing gel. Thus, if one enzyme discriminates 1000-fold greater against a given ddNTP compared to another enzyme, a 1000-fold higher ratio of ddNTP to dNTP will be necessary to obtain bands terminating at the corresponding sites in the same range of the gel.

Exonuclease Activity

The DNA polymerases of the invention preferably have less than 50%, preferably less than 1%, and most preferably less than 0.1%, of the normal or naturally associated level of exonuclease activity (amount of activity per polymerase molecule). By normal or naturally associated level is meant the exonuclease activity of e.g., an unmodified T7-type polymerase. Normally the associated activity is about 5,000 units of exonuclease activity per mg of polymerase, measured as described below by a modification of the procedure of Chase et al. (249 *J. Biol. Chem.* 4545, 1974). Exonucleases increase the fidelity of DNA synthesis by excising any newly synthesized bases which are incorrectly base-paired to the template. Such associated exonuclease activities can be detrimental to the quality of DNA sequencing reactions. They raise the minimal required concentration of nucleotide precursors which must be added to the reaction since, when the nucleotide concentration falls, the polymerase activity slows to a rate comparable with the exonuclease activity, resulting in no net DNA synthesis, or even degradation of the synthesized DNA.

More importantly, associated exonuclease activity may cause a DNA polymerase to idle at regions in the template with secondary structure impediments. When a polymerase approaches such a structure its rate of synthesis decreases as it attempts to pass. An associated exonuclease will excise the newly synthesized DNA when the polymerase stalls. As a consequence numerous cycles of synthesis and excision will occur. This may result in the polymerase eventually synthesizing past the hairpin (with no detriment to the quality of the sequencing reaction); or the polymerase may dissociate from the synthesized strand (resulting in an artifactual band at the same position in all four sequencing reactions); or, a chain terminating agent may be incorporated at a high frequency and produce a wide variability in the intensity of different fragments in a sequencing gel. This happens because the frequency of incorporation of a chain terminating agent at any given site increases with the number of opportunities the polymerase has to incorporate the chain terminating nucleotide.

An ideal sequencing reaction will produce fragments that give bands of uniform intensity throughout the gel. This is essential for obtaining the optimal exposure of the X-ray film for every radioactive fragment. If there is variable intensity of radioactive bands, then fainter bands may go undetected. To obtain uniform radioactive intensity of all fragments, the DNA polymerase should spend the same interval of time at each position on the DNA, showing no preference for either the addition or removal of nucleotides at any given site. This occurs if the DNA polymerase lacks any associated exonuclease, so that it will have only one opportunity to incorporate a chain terminating nucleotide at each position along the template.

Short Primers

The DNA polymerase of the invention is preferably able to utilize primers of 10 bases or less, as well as longer ones, most preferably of 4–20 bases e.g., 6 bases (which can be used in groups of three to form an equivalent of an 18-mer). The ability to utilize short primers offers a number of important advantages to DNA sequencing. The shorter primers are less expensive and easier to synthesize than the usual 17-mer primers. They also anneal faster to complementary sites on a DNA template, thus making the sequencing reaction faster. Further, the ability to utilize small (e.g., six or seven base) oligonucleotide primers for DNA sequencing permits strategies not otherwise possible for sequencing long DNA fragments. For example, a kit containing 80–4000 random hexamers could be generated, none of which are complementary to any sites in the cloning vector. Statistically, one of the 80 hexamer sequences will occur an average of every 50 bases along the DNA fragment to be sequenced. The determination of a sequence of 3000 bases would require only five sequencing cycles. First, a "universal" primer (e.g., New England Biolabs #1211, sequence 5' GTAAAACGAACGGCCAGT 3') (SEQ ID. NO:25) would be used to sequence about 600 bases at one end of the insert. Using the results from this sequencing reaction, a new primer would be picked from the kit homologous to a region near the end of the determined sequence. In the second cycle, the sequence of the next 600 bases would be determined using this primer. Repetition of this process five times would determine the complete sequence of the 3000 bases, without necessitating any subcloning, and without the chemical synthesis of any new oligonucleotide primers. The use of such short primers may be enhanced by including gene 2.5 and gene 4 protein of T7 in the sequencing reaction.

In vitro Mutagenesis

Mutagenesis of the polymerase genes was carried out using standard PCR techniques (see below).

Discrimination against ddNTPs

In the presence of magnesium as the only divalent cation, T7 DNA polymerase discriminates about 3–4 fold against ddNTPs, less than any other known polymerase. The next closest is reverse transcriptase, that discriminates about 10–50-fold against ddNTPs (3–10 times more than T7 DNA polymerase). After these two, all other known DNA polymerases characterized in the literature discriminate at least 100-fold against ddNTPs, and often 10,000 fold or more.

In the presence of manganese discrimination by T7 DNA polymerase and *E. coli* DNA polymerase I are reduced; with T7 DNA polymerase, it is reduced from 3.7 to 1, and with *E. coli* DNA polymerase I it is reduced from 550 to 3.9 (for ddATP). Applicant is the first to provide a DNA polymerase that in the presence of magnesium ions as the only divalent cations has a processivity of less than 100 (defined as the average length of extension from a given primer before dissociating from the primer-template; Reverse transcriptase has a processivity by this definition of about 150–200, and T7 DNA polymerase has a processivity greater than this) and that discriminates less than 100 fold against incorporation of a ddNMP. In contrast, most of the known DNA polymerases, such a Taq that have a processivity less than 100 discriminate more than 100 fold against incorporation of a ddNMP.

Previously it was believed that whereas polymerases with high processivity such as T7 DNA polymerase remain bound to a primer-template for up to several minutes, polymerases with low processivity such as *E. coli* DNA polymerase I cycle from one primer template to another every few seconds (or over one hundred times more frequently). See for example Tabor, et al. *J. Biol. Chem.* 262, 16212–16223 (1987)). While processivity is advantageous for DNA sequencing, as in reducing the background due to terminations not from dideoxy incorporation, the slow cycling time is a disadvantage. For example, if the polymerase does dissociate at specific sequences, it will result in strong artifactual bands on a sequencing gel unless there is a large excess of polymerase present. On the other hand, with a polymerase that cycles rapidly, one can use much less polymerase since a single enzyme molecule will extend many different primers during the course of a sequencing reaction, and any given primer end will have the opportunity to be extended by many different polymerase molecules, decreasing the chance of strong specific stops from occurring.

However, it is better that a polymerase that cycles rapidly also incorporates ddNMPs efficiently, in order to give bands of uniform intensity and allow one to use less ddNTPs. It is also preferred that such a polymerase have low or no exonuclease activity, and that one add pyrophosphatase to prevent degradation of bands by pyrophosphorolysis.

It is also preferred that one be able to carry out DNA sequencing reactions with magnesium as the only divalent cation (i.e., the absence of manganese). First, polymerases tend to be less active with manganese compared with magnesium (see for example Tabor and Richardson. *Proc. Natl. Acad. Sci.* USA 86, 4076–4080 (1989)). Second, while polymerases tend to be active over wide ranges of magnesium concentrations, there is a very sharp, low optimum manganese concentration required in most cases for optimum activity (id.). And at the optimum manganese concentrations there is much less effect on reduction of discrimination against ddNTPs as at much higher concentrations, where the polymerase is much less active. Third, manganese is not as convenient a metal ion to have in a kit; it readily forms precipitates, particularly at higher pH's. Fourth, it is not clear whether manganese will be effective as a metal ion for reducing discrimination against ddNTPs with any thermophilic polymerase (i.e., at higher temperatures).

Prior to the present invention, we stated (Tabor and Richardson *Proc. Natl. Acad. Sci.* USA 86, 4076–4080 (1989)) that there was a correlation between discrimination and processivity:

"DNA polymerase I has a low processivity, dissociating after the incorporation of less than 10 nucleotides. There is a strong correlation between the frequency at which the enzyme dissociates from a site during DNA synthesis in the absence of ddNTPs, and the extent of discrimination against the incorporation of a ddNMP at that site (unpublished results). This suggests that DNA polymerase I incorporates dNMPs and ddNMPs at similar rates during processive synthesis; however, when synthesis is non-processive, dNMPs are incorporated preferentially over ddNMPs. This model could account for the greater variabiliy in ddNMP incoparation by DNA polymerase I compared to T7 DNA polymerase, since the latter has a processivity two orders of magnitude greater than the former." [Citations omitted.]

Thus the results of this invention with *E. coli* DNA polymerase I and Taq DNA polymerase are surprising, since we find no evidence that the mutants described herein do increase the processivity of the mutant enzymes.

Thermophilic Polymerases

Thermophilic polymerases that discriminate against a ddNTP by less than a factor of 100 are particularly useful in this invention. In, addition, those that discriminate against a ddNTP by less than a factor of 100 in the presence of magnesium as the only divalent cation and preferably cycle from one primer-template to another more than once per second are useful. Thermophilic polymerases are defined as polymerases that have optimum DNA polymerase activity in a 15 min. reaction at a temperature above 60 degrees Celcius.

Uniform Band Intensities

Even though manganese reduces the discrimination of Klenow fragment against ddATP from 550 to 3.9 fold Tabor and Richardson (*Proc. Natl. Acad. Sci.* USA 86, 4076–4080 (1989)) show that there is still wide variability in the intensity of individual bands (see FIG. 2 id.). Thus, apart from T7 DNA polymerase, this invention is the first to provide polymerases that cycle rapidly such as Klenow fragment and those that are derived from thermophilic organisms to produce bands that have uniform intensities, even in the presence of magnesium as the only divalent cation, conditions that are preferable for the activity of most polymerases (see above). Enzymes which cycle rapidly can be determined by methods known in the art as described below.

Specific Polymerases

From the above information it is possible to readily make the following polymerases which will have the desired properties discussed above. Each of these polymerases can be used for sequencing procedures if the level of exonuclease is low enough and the activity of the polymerase is sufficient (both of which are well known in the art). See Braithwaite and Ito, supra for reference to each amino acid site.

1. Pol I Family

*E. coli* DNA polymerase I with altered Phe762 (altered means replaced with e.g., Tyr, or an equivalent amino acid to give the non-discriminatory property).

*Streptococcus pneumoniae* DNA polymerase I with altered Phe711.

*Thermus aquaticus* DNA polymerase I with altered Phe667.

*Thermus flavus* DNA polymerase I with altered Phe666.

Bacteriophage T5 DNA polymerase with altered Phe570.

Bacteriophage Spo 1 DNA polymerase with altered Leu526.

Bacteriophage Spo 2 DNA polymerase with altered Phe690.

Mitochondrial DNA polymerase with natural Tyr753 or altered at this site without reducing the non-discriminatory activity. Such a polymerase has not previously been used for DNA sequencing. Applicant believes that it will be useful in such a procedure because of its expected low level of ddNTP discrimination. If needed, it can be modified to reduce exonuclease activity associated with the polymerase activity.

2. Polymerase Alpha Family (Also Called Polymerase II Family)

Delarue et al., *Protein Engineering* 3, 461–467 (1990) show that the two families of polymerases (polymerase I family and polymerase alpha family) share three common motifs. The region they call "Motif B" contains the residue we have identified as responsible for specificity for the dideoxyribose moiety. This region is characterized by the sequence K $N_1$ $N_2$ $N_3$ $N_4$ $N_5$ $N_6$ $N_7$ Y G in the polymerase I family, where $N_4$ is the specificity residue: if $N_4$ is a phenylalanine there is high discrimination, if $N_4$ is tyrosine there is low discrimination. In the polymerase alpha family, the sequence is K $N_1$ $N_2$ $N_3$ $N_4$ $N_5$ $N_6$ Y G (there is one less base between the conserved residues). We predict therefore that just as with polymerase I type enzymes, changes to the residue(s) in this motif (betwen the lysine (K) and the tyrosine (Y)) will reduce the discrimination of these polymerases to ddNTPs. These residues are as follows:

| | |
|---|---|
| *Escherichia coli* DNA polymerase II | Ile494—Phe499 |
| PRD1 DNA polymerase | Leu341—Ser346 |
| Ø 29 DNA polymerase | Leu384—Leu389 |
| M2 DNA polymerase | Leu381—Leu386 |
| T4 DNA polymerase | Ile558—Leu563 |
| *Thermuococcus litoralis* DNA polymerase (Vent) | Leu492—Tyr497 |
| *Pyrococcus furiosus* DNA polymerase | Leu489—Phe494 |
| *Sulfolobus solfataricus* DNA polymerase | Val604—Thr609 |
| Human DNA polymerase alpha | Leu951—His956 |
| *S. cerevisiae* DNA polymerase I (alpha) | Leu945—His950 |
| *S. pombe* DNA polymerase I (alpha) | Leu931—His936 |
| *Drosophila melanogaster* DNA polymerase alpha | Leu960—His965 |
| *Trypanosoma brucei* DNA polymerase alpha | Leu845—His850 |
| Human DNA polymerase delta | Val695—Val700 |
| Bovine DNA polymerase delta | Val694—Val699 |
| *S. cerevisiae* DNA polymerase III (delta) | Ile702—Val707 |
| *S. pombe* DNA polymerase III (delta) | Val681—Val686 |
| *Plasmodium falciparum* DNA polymerase delta | Ile692—Val697 |
| *S. cerevisiae* DNA polymerase II (epsilon) | Val825—Phe830 |
| *S. cerevisiae* DNA polymerase Rev3 | Leu1087—Thr1092 |

| | |
|---|---|
| Herpes Simplex virus type 1 DNA polymerase | Val812—Val817 |
| Equine herpes virus type 1 DNA polymerase | Val813—Val818 |
| Varicella-Zoster virus DNA polymerase | Val776—Val781 |
| Epstein-Barr virus DNa polymerase | Cys682—Val687 |
| Herpesvirus saimiri DNA polymerase | Val671—Val676 |
| Human cytomegalovirus DNA polymerase | Val811—Phe816 |
| Murine cytomegalovirus DNa polymerase | Val717—Phe722 |
| Human herpes virus type 6 DNA polymerase | Ile667—Val672 |
| Channel Catfish virus DNA polymerase | Ile750—His755 |
| Chlorella virus DNA polymerase | Ile586—Val591 |
| Fowlpox virus DNA polymerase | Ile648—Val653 |
| Vaccinia virus DNA polymerase | Ile637—Val642 |
| *Choristoneura biennis* DNA polymerase | Ile669—Leu674 |
| *Autographa californica* nuclear polyhedrosis virus (AcMNPV) DNA polymerase | Arg606—Ile611 |
| *Lymantria dispar* nuclear polyhedrosis virus DNA polymerase | Arg624—Ile629 |
| Adenovirus-2 DNA polymerase | Leu696—Leu701 |
| Adenovirus-7 DNA polymerase | Leu762—Leu767 |
| Adenovirus-12 DNA polymerase | Leu694—Leu699 |
| S-1 maize DNA polymerase | Leu618—Leu623 |
| kalilo *neurospora intermedia* DNA polymerase | Leu776—Leu777 |
| pAI2 *Ascobolus immersus* DNA polymerase | Leu951—Leu956 |
| pCLK1 *Claviceps purpurea* DNA polymerase | Leu831—Leu836 |
| Maranhar *neurospora crassa* DNA polymerase | Leu752—Leu757 |
| pEM *Agaricus bitorquis* DNA polymerase | Leu573—Leu578 |
| pGKL1 *Kluyveromyces lactis* DNA polymerase | Ile785—Leu790 |
| pGKL2 *Kluyveromyces lactis* DNA polymerase | Ile770—Gly776 |
| pSKL *Saccaromyces kluyveri* DNA polymerase | Ile775—Gly781 |

EXAMPLES

The following are examples of methods for determining the processivity and cycle times for various polymerases. Also provided are examples for determining the level of discrimination by a polymerase, and other methods useful in this invention.

Example 1

Mutagenesis of DNA Polymerase Genes and Overproduction of Mutant DNA Polymerases Standard techniques are used for the cloning and expression of mutant DNA polymerase genes. The genes for the large fragment of *E. coli* DNA polymerase I (Klenow fragment) and the large fragment of Taq DNA polymerase (KlenTaq or ΔTaq DNA polymerase, see Barnes 112 Gene 29, 1992 or Stoffel fragment, see Lawyer et al. 2 PCR Methods Appl 275, 1993), the starting materials for the generation of mutants in *E. coli* DNA polymerase I and Taq DNA polymerase, are expressed under the control of the T7 RNA polymerase promoter. The gene for the Δ28 amino acid deletion of T7 DNA polymerase (see Tabor and Richardson 264, *J. Biol. Chem.* 6447, 1989), the starting material for the generation of mutants in T7 DNA polymerase, is expressed under the control of the lac promoter in a strain that produces *E. coli* thioredoxin, a necessary factor for processive DNA synthesis by T7 DNA polymerase (Tabor and Richardson, supra). The gene for Taq DNA polymerase mutant F667Y is transferred from the gene that produces ΔTaq DNA polymerase to the gene that produces the full length Taq DNA polymerase by standard techniques using PCR and restriction digestion followed by ligation.

Mutagenesis to construct the mutant DNA polymerases is carried out using standard mutagenesis techniques by PCR similar to the method described by Sarkar and Sommer 8 *BioTechniques* 404, 1990. To construct hybrids in which more than four amino acid residues are being exchanged, two hybrid primers are constructed whereby PCR is first carried out on the donor DNA, and then that product is used for PCR on the recipient DNA, generating the hybrid molecule. For the construction of hybrids in which the exchange of domains is four amino acid residues or less, single PCR primers are synthesized that contain the entire region to be transferred as well as the proper flanking sequences of the recipient, and that primer is used to construct the hybrid molecule directly.

Overproduction of the mutant DNA polymerases is carried out using standard techniques (see for example Current Protocols in Molecular Biology, Ausubel et al, eds., Chapter 16, 1994). Mutant proteins are purified by standard procedures including ion exchange chromatography. For the purification of *E. coli* DNA polymerase I mutants, see for example Joyce and Grindley 80 *Proc. Natl. Acad. Sci.* 1830, 1983. For the purification of Taq DNA polymerase mutants, see for example Engelke et al. 191 *Analytical Biochemistry* 396, 1990. For the purification of T7 DNA polymerase mutants, see for example Tabor and Richardson 264, *J. Biol. Chem.* 6447, 1989. Polymerase specific activities of each of the purified mutant proteins are determined by standard procedures described in these references.

Example 2

Rapid Screen of DNA Polymerases for Mutants That are Improved in Their Efficiency of Incorporating a Dideoxynucleotide Relative to a Deoxynucleotide Mutant DNA polymerases are screened for their ability to incorporate dideoxynucleotides by SDS activity gel analysis. The procedure is a modification of that described by Spanos and Hübscher 91 *Methods in Enzymology* 263, 1983 and Karawya et al. 135 *Analytical Biochemistry* 318, 1983. Briefly, 10 ml of cells are induced for 4 to 6 hours and then pelleted. The cell pellet is resuspended in 0.3 ml 25 mM Tris.HCl, pH 7.0, 5 mM EDTA. 20 μl of the resuspended cells are mixed with 40 μl of a solution of 1% SDS (sodium dodecyl sulfate), 2% mercaptoethanol, 30% glycerol, 0.04% bromphenol blue, and 100 mM Tris.HCl, pH 6.8. The mixtures are incubated at 37° C. for 5 min, and then 20 μl aliquots are loaded in duplicate onto two SDS polyacrylamide gels. The SDS polyacrylamide gels consist of a resolving gel that contains 8% polyacrylamide, 0.27% bisacrylamide, 190 mM Tris.HCl, pH 8.8, 0.05% SDS, and 25 μg/ml denatured salmon sperm DNA, and a stacking gel that consists of 5% polyacrylamide, 0.17% bisacrylamide, 150 mM Tris.HCl, pH 6.8, and 0.1% SDS. The two gels are electrophoresed at 100 V for 13 hr at a constant temperature of 13° C. in an electrophoresis buffer consisting of 190 mM Tris.HCl and pH 8.8, 0.05% SDS.

After electrophoresis, the gels are washed over 8 hr in 4 changes of 500 ml each of Renaturation Buffer (50 mM Tris.HCl, pH 7.5, 5 mM magnesium acetate, 1 mM dithiothreitol, 40 mM KCl, 400 μg/ml bovine serum albumin, 16% glycerol and 0.95 mM EDTA) at 4° C.

The renatured proteins are assayed for DNA polymerase activity by incubating each of the two gels in 6 ml of Renaturation Buffer, 1.5 μM 4 dNTPs, 4 μl of [α-$^{32}$P]dATP (800 Ci/mmol, 10 mCi/ml), and 80 µg of purified thioredoxin. One of the mixtures also contains 30 µM ddTTP (a 20-fold molar excess over dTTP). The mixtures are incubated for 4 hr at 37° C. (70° C. for 2 hr for thermophilic DNA polymerases).

After incubation the gels are washed for 8 hr against four changes of 5% trichloracetic acid and 1% sodium pyrophosphate. The gels are then dried and autoradiographed.

To determine whether a mutant DNA polymerase is discriminating more or less against ddTTP, the intensities of the radioactive bands are compared on the two gels that were incubated in the presence and absence of ddTTP, and the ratio of the signal in the two bands for the unmodified DNA polymerase is compared with the ratio of the signal in the two bands for each of the mutants. If a mutation results in a DNA polymerase being less discriminatory towards ddTTP, then there will be a greater percentage decrease in radioactivity in the band in which ddTTP was present for the mutant DNA polymerase compared with the unmodified DNA polymerase. For example, under these conditions the radioactive bands observed for cells containing induced *E. coli* DNA polymerase I or T7 DNA polymerase mutant Y526F are approximately the same intensity (within a factor of two) in reactions carried out in the presence versus the absence of ddTTP. In contrast, for cells containing induced *E. coli* DNA polymerase I mutant F762Y or T7 DNA polymerase, the bands on the gel in which the reactions are carried out in the presence of ddTTP are less that 5% the intensity of the bands corresponding to the reactions carried out in the absence of ddTTP.

This assay represents a rapid method of screening a large number of DNA polymerase mutants for their ability to discriminate against dideoxynucleotides. It can detect changes of at least 5-fold in the relative rate of discrimination. However, this assay should be followed up with purification of potentially interesting mutant DNA polymerases and more rigorous assays of the purified proteins similar to those described below in order to determine precisely the effect of each mutation on discrimination against dideoxynucleotides.

The following examples are methods for determining the processivity and cycle times for various polymerases, determining the level of discrimination against ddNTPs by a polymerase, determining the uniformity of bands generated by dideoxy-terminated fragments on a DNA sequencing gel, and using the DNA polymerases of this invention for DNA sequence analysis.

Example 3

Preparation and Purification of a Single-Stranded M13 DNA - 5' $^{32}$P-labeled 40-mer Primer Complex The template is M13 mGP1-2 single-stranded DNA, 9950 nucleotides in length, as described in U.S. Pat. No. 4,795,699 (FIG. 9). The phage M13 mGP1-2 is deposited in ATCC as number 40303. M13 mGP1-2 single-stranded DNA is purified as described in Tabor et al., 262 *J. Biol. Chem.* 16212, 1987. Briefly, the phage is purified through two CsCl gradient centrifugations, the CsCl is removed by dialysis, the DNA is removed from the phage by extraction with phenol and chloroform in the presence of 0.1% sodium dodecyl sulfate, and the extracted DNA is dialyzed extensively against 20 mM Tris.HCl, pH 7.5, 2 mM EDTA and stored at 4° C. The concentration of M13 mGP1-2 single-stranded DNA is determined spectrophotometrically using an extinction coefficient of 8.1 $A_{260}$ units=1 mg/ml, or 0.3 pmoles of M13 mGP1-2 template molecules per microliter.

The primer is a synthetic 40-mer having the sequence 5' d(TTTTCCCAGTCACGACGTTGTAAAAC-GACGGCCAGTGCCA)3' (SEQ ID. NO:26) synthesized by standard procedures. It is complementary to M13 mGP1-2 DNA at nucleotides 9031 to 8992 (see '699 patent supra for sequence). The primer is purified by ion exchange chromatography or denaturing polyacrylamide gel electrophoresis prior to end labeling.

The primer is labeled and annealed to the template essentially as described in Tabor et al (supra). The primer is 5' end labeled in a reaction mixture (15 µl) containing 40 mM Tris.HCl, pH 7.5, 10 mM MgCl$_2$, 5 mM dithiothreitol, 100 mM NaCl, 50 µg/ml BSA, 50 µCi [$\gamma^{32}$P]ATP, 6000 Ci/mmol, 5 pmoles of primer, and 10 units of T4 polynucleotide kinase prepared from the PseT1 mutant, which is deficient in phosphatase activity. The mixture is incubated at 37° C. for 15, min, followed by 70° C. for 15 min to inactivate the kinase. 60 µl of single-stranded M13 mGP1-2 DNA (0.25 mg/ml), 6 µl of 1M NaCl and 3 µl of 0.2M MgCl$_2$ are added, and the mixture is slowly cooled from 70° C. to room temperature (about 20°–25° C.) over a period of 30 min. The mixture is then extracted once with a 1:1 mixture of phenol and chloroform, and after centrifugation for 30 sec in a microfuge, the aqueous phase (70 µl) is placed on a 1 ml column of Sepharose CL-6B equilibrated in 20 mM Tris.HCl, pH 7.5, 2 mM EDTA, and 100 mM NaCl. The labeled primer-template complex is eluted from the column with the same buffer used for equilibration; the labeled complex elutes in the void volume. After elution, the complex is at a concentration of approximately 50 µg/ml (0.015 pmoles of molecules per µl) with a specific activity of approximately 200,000 cpm/µl.

Example 4

Determination of the Processivity of a DNA Polymerase by Dilution Test

Processivity is determined by enzyme dilution essentially as described in Tabor et al (supra) and Tabor and Richardson, 84 *Proc. Natl. Acad. Sci USA* 4767, 1987. The reactions are carried out under the same conditions as in the extension/termination reactions used in DNA sequencing (Tabor and Richardson, supra), except that ddNTPs are omitted and the polymerase concentration is reduced in order to have an excess of primer-template molecules over polymerase molecules in some of the reactions. The primer-template consists of the single 5' end-labeled primer annealed to a single-stranded M13 DNA molecule as described in Example 3.

The extension reaction mixtures are prepared substantially as described in Tabor et al (supra). Each reaction mixture (18 µl) contains 1.0 µl annealed $^{32}$P-labeled primer-M13 DNA as described in Example 3 (~0.015 pmoles, ~200,000 cpm), 40 mM Tris.HCl, pH 8.0, 5 mM MgCl$_2$, 5 mM dithiothreitol, and 300 µM 4 dNTPs. The mixtures are incubated at 37° C. for 1 min (70° C. for thermophilic DNA polymerases). The reactions are initiated by the addition of 2 µl aliquots of dilutions of the DNA polymerase being analyzed, diluted in 20 mM Tris.HCl, pH 7.5, 10 mM 2-mercaptoethanol and 0.05% bovine serum albumin. The reaction mixtures are further incubated at 37° C. (70° C. for thermophilic DNA polymerases) for either 30 sec or 3 min. At the indicated times, 8 µl aliquots are removed and added to either 8 µl of 90% formamide, 20 mM EDTA, 0.05% bromphenol blue for denaturing polyacrylamide gel electrophoresis, or 2 µl of 100 mM EDTA, 2% sodium dodecyl sulfate for alkaline agarose gel electrophoresis.

The samples are analyzed by either denaturing polyacrylamide gel electrophoresis or alkaline agarose gel electrophoresis. Denaturing polyacrylamide gel electrophoresis is most suitable for analyzing polymerases with an average processivity of less than 500 nucleotides, while alkaline agarose gel electrophoresis provides a more sensitive estimate of the processivity of DNA polymerases with an average processivity greater than 500 nucleotides; however, either method can be used successfully to determine the average processivity of any DNA polymerase.

To determine the processivity by denaturing polyacrylamide gel electrophoresis, aliquots in formamide are heated at 90° C. for 2 min immediately prior to loading 6 µl of each sample onto a gel consisting of 8% polyacrylamide, 0.4% N,N'-methylenebisacrylamide, 7M urea in 100 mM Tris.borate, pH 8.3, 1 mM EDTA. Electrophoresis is at 2000 Volts for 90 min (until the bromphenol blue has just run off the bottom of the gel). Suitable 5' $^{32}$P-end labeled molecular weight markers are also loaded onto the gel that allow the determination of fragment sizes 100 to 500 nucleotides in length. An example of such suitable markers are T7 HpaI fragments that have been dephosphorylated with alkaline phosphatase and then 5' $^{32}$P-end labeled using [γ-$^{32}$P]ATP and T4 polynucleotide kinase using standard procedures (Sambrook et al., 1989, Molecular Cloning A Laboratory Manual, Cold Spring Harbor Laboratory, N.Y. pp. 6.20–6.21 and Ausubel et al., 1989, Current Protocols in Molecular Biology, Greene Publishing Associates and Wiley Interscience, N.Y.). After electrophoresis, the gel is dried under vacuum, and autoradiographed. After autoradiography, the distribution of radioactively labeled fragments is determined by Phosphorimager analysis (Molecular Dynamics).

Products are analyzed by alkaline agarose gel electrophoresis as described by (1) Villani et al., 256 *J. Biol. Chem.* 8202, 1981, by (2) Sabatino et al., 27 *Biochemistry* 2998, 1988, and by (3) Sambrook, et al., supra. To prepare the agarose gel, 250 ml of a 1.5% agarose solution in 2 mM EDTA, pH 8.0 is heated in a microwave oven to dissolve the agarose, and then allowed to cool to 60° C. 8.75 ml of 1N NaOH (final concentration 35 mM NaOH) is added, the gel is poured into an agarose gel electrophoresis mold. The gel is allowed to set for 2 hours before use. The electrophoresis buffer is 35 mM NaOH and 2 mM EDTA. The samples are prepared by taking the 10 µl aliquots described above (in 20 mM EDTA, 0.4% sodium dodecyl sulfate) and denatured by the addition of 1 µl of 1N NaOH and heating at 60° C. for 10 min. 7 µl of 75% glycerol, 0.2% bromcresol green are added to each sample, and then the samples are loaded onto the alkaline agarose gel. Electrophoresis is carried out at 4° C. at a constant current of 150 mA for 15 hours (until the bromcresol green has migrated about 14 cm). The electrophoresis chamber has dimensions of 26 cm (length)×20 cm (width) by 2 cm (height). After electrophoresis, the gel is soaked for 2 hours in 10% trichloracetic acid, dried under vacuum, and autoradiographed. After autoradiography, the distribution of radioactively labeled fragments is determined by Phosphorimager analysis (Molecular Dynamics).

To test the processivity of a given DNA polymerase, the concentration of that polymerase in the reaction mixture is diluted by 2-fold increments until only a fraction (e.g. 25%) of the primers are extended, while the majority (e.g. 75%) remained unchanged, 40 nucleotides in length. Under these conditions, a two-fold increase or decrease in DNA polymerase concentration should result in about a two fold increase or decrease, respectively, in the fraction of primers extended. The average length of the labeled fragments that are extended is determined either by visual inspection of the autoradiograph or by quantitation using a phosphoimager. For example, using this test, the exonuclease-deficient T7 DNA polymerase complexed to its processivity factor thioredoxin (e.g. SEQUENASE® Version 2.0, United States Biochemical Corporation) has an average processivity of more than 500 nucleotides, while Klenow fragment of *E. coli* DNA polymerase I has a processivity of less than 50 nucleotides.

Example 5

Determination of the Rate of Cycling of a DNA Polymerase

The rate of cycling is determined essentially as described Tabor et al (supra). The reactions are carried out under the same conditions as in the extension/termination reactions used in DNA sequencing (Tabor and Richardson, supra), except that ddNTPs are omitted and the polymerase concentration is reduced in order to have an excess of primer-template molecules over polymerase molecules. The primer-template consists of the 5'[$^{32}$P]end-labeled primer annealed to single-stranded M13 DNA molecule as described in Example 3.

First a test is carried out to determine the functional ratio of primer-template molecules to polymerase molecules, for example, using the large fragment of *E. coli* DNA polymerase I (Klenow fragment). A dilution experiment is carried out as described in Example 4, to determine the concentration of polymerase molecules necessary to extend 20% of the labeled primer-template molecules in 10 sec. This ratio of polymerase to primer-template is defined as being less than or equal to 1:5, and is used to determine the maximum rate of cycling of the polymerase as described below.

Extension reactions are carried out as described in Example 4 using the ratio of DNA polymerase to primer-template less than or equal to 1:5, as defined in the previous paragraph. Reactions are carried out under conditions (i.e. buffer, pH, salt, temperature) optimal for the polymerase being tested. Aliquots are removed at 10 sec, 20 sec, 40 sec and 80 sec, and the reactions are terminated and the products analyzed as described in Example 4. For DNA polymerases with low processivity (less than 100 nucleotides), such as the large fragment of *E. coli* DNA polymerase I, samples are analyzed preferably by denaturing polyacrylamide gel electrophoresis. For DNA polymerases with high processivity (greater than 100 nucleotides), such as T7 DNA polymerase, samples are analyzed preferably by alkaline agarose gel electrophoresis. After electrophoresis, the gels are dried under vacuum and analyzed either by autoradiography or with a Phosphoimager.

When reactions are carried out with a polymerase that cycles very slowly, such as T7 DNA polymerase, there is not a significant decrease (i.e. less than a factor of two) in the number of unextended primers between 10 sec and 80 sec. Thus, if the number of unextended labeled primers does not decrease by more than two fold between the 10 sec and 80 sec time points, then the DNA polymerase cycles slower than once per 70 sec. For polymerases that cycle rapidly, the number of unextended primers will decrease by a significant fraction (i.e. by more than 2 fold) between the 10 and 80 sec time points. To determine the rate of cycling for these polymerases, the following equation is used:

$$R = N_1 \times L(t_2) / \{L(t_1) \times (t_2 - t_1)\}$$

where:

R=minimum rate of cycling in cycles per sec.

$N_1$=ratio of primer-template molecules over functional DNA polymerase molecules. ($N_1$=5 in the example above.)

$L(t_1)$=the maximum processivity of the DNA polymerase being investigated, in nucleotides. This is defined as the maximum number of nucleotides extended from the labeled primers under conditions of limiting DNA polymerase (where only 20% of the primers are extended in the 10 sec time point), as described in Example 3.

$L(t_2)$=the maximum length of extension (in nucleotides) of the labeled primers at time $t_2$, which is 80 sec in this example.

$t_1$: the shortest time at which an aliquot is taken, or 10 sec in this example.

$t_2$: the longest time the reaction is allowed to precede before removing an aliquot, or 80 sec in this example.

When this test is carried out for the large fragment of *E. coli* DNA polymerase I, a value of more than 0.2 cycles per sec is obtained.

Examples 6 and 7 provide tests to determine the efficiency of incorporation of dideoxynucleotides for an unknown DNA polymerase using a 5' $^{32}$P-labeled 40-mer primer annealed to a single-stranded M13 DNA template and a gel electrophoresis-based analysis. Example 6 is best for DNA polymerases that efficiently incorporates dideoxynucleotides (e.g. wild-type T7 DNA polymerase and Taq DNA polymerase F667Y) while Example 7 is best for DNA polymerases that discriminate strongly against the incorporation of dideoxynucleotides (e.g. T7 DNA polymerase Y526F and wild-type Taq DNA polymerase).

Example 6

Gel Electrophoresis-based Determination of the Rate of Incorporation of Dideoxynucleotides Relative to Deoxynucleotides Using a 1:1 Ratio of dNTPs to ddNTPs The primary application of this test is to determine the absolute ratio of incorporation of a ddNMP to a dNMP for a DNA polymerase that efficiently incorporates dideoxynucleotides, such as T7 DNA polymerase, *E. coli* DNA polymerase I mutant F762Y or Taq DNA polymerase mutant F667Y. It can also indicate the level of discrimination against ddNTPs of any DNA polymerase; however, for DNA polymerases that discriminate strongly against ddNTPs, such as T7 DNA polymerase mutant Y526F, *E. coli* DNA polymerase I or Taq DNA polymerase, higher ratios of ddNTP to dNTP are necessary to determine precisely their level of discrimination, which is described in detail in Example 7.

DNA synthesis reactions are carried out on the $^{32}$P-end labeled 40 mer-M13 mGP1-2 DNA template complex prepared as described in Example 3. Reaction conditions are used that are optimum for the DNA polymerase being tested with regard to buffer, pH, salts, and temperature of the reaction. A concentration of DNA polymerase is chosen whereby most of the primers are extended in a 10 min reaction and are terminated by the incorporation of a dideoxynucleotide. The reaction mixture contains 100 µM 4 dNTPs and 100 µM of one of the four ddNTPs.

We used this test to compare the ability of six DNA polymerases to incorporate each of the four ddNMPs. The DNA polymerases tested were (1) T7 DNA polymerase with a 28 amino acid deletion in the exonuclease domain and complexed in a one-to-one ratio with thioredoxin (Tabor and Richardson 264 *J. Biol. Chem.* 6447, 1989) (referred to here as "T7 DNA polymerase"), (2) The large fragment of *E. coli* DNA polymerase I, commonly called the Klenow fragment (referred to here as "*E. coli* DNA polymerase I'"), (3) Unmodified DNA polymerase from *Thermus aquaticus* (referred to here as "Taq DNA polymerase"), (4) T7 DNA polymerase as described above in which the tyrosine at residue 526 has been changed to a phenylalanine (referred to here as "T7 DNA polymerase Y526F"), (5) *E. coli* DNA polymerase I as described above in which the phenylalanine at residue 762 has been changed to a tyrosine (referred to here as "*E. coli* DNA polymerase I F762Y"), and (6) Taq DNA polymerase as described above in which the phenylalanine at residue 667 has been changed to a tyrosine (referred to here as "Taq DNA polymerase F667Y").

To test the relative rate of use of each of the four ddNTPs compared to the comparable dNTPs for each of the DNA polymerases indicated above, the reaction mixtures (8 µl) contained 1.0 µl annealed $^{32}$P-labeled primer-M13 DNA as described in Example 3 (~0.015 pmoles, ~200,000 cpm), 40 mM Tris.HCl, pH 8.0, 5 mM $MgCl_2$, 5 mM dithiothreitol, 50 mM NaCl, 100 µM 4 dNTPs, and 100 µM ddCTP. The reaction mixtures also contained 10 ng of yeast inorganic pyrophosphatase to inhibit pyrophosphorolysis that could otherwise increase the apparent discrimination by the DNA polymerase (Tabor and Richardson 265 *j. Biol. Chem.* 8322, 1990). The reactions were initiated by the addition of 2 µl of each DNA polymerase, diluted in 20 mM Tris.HCl, pH 7.5, 10 mM 2-mercaptoethanol and 0.05% bovine serum albumin to a concentration of approximately 0.025 units/µl. The concentration of each DNA polymerase was sufficient to extend most of the labeled primers by more than 500 nucleotides in the absence of ddNTPs in a 15 min reaction. The reaction mixtures were incubated for 15 min at either 37° C. (T7 DNA polymerase, T7 DNA polymerase Y526F, *E. coli* DNA polymerase I, and *E. coli* DNA polymerase I F762Y) or 70° C. (Taq DNA polymerase and Taq DNA polymerase F667Y). The reactions were terminated by the addition of 10 µl 90% formamide, 20 mM EDTA, 0.05% bromphenol blue. Each sample was heated at 90° C. for 2 min immediately prior to loading 6 µl of each sample onto a gel consisting of 8% polyacrylamide, 0.4% N,N'-methylenebisacrylamide, 7M urea in 100 mM Tris.borate, pH 8.3, 1 mM EDTA. Electrophoresis was at 2000 Volts for 90 min (until the bromphenol blue had just run off the bottom of the gel). After electrophoresis, the gel was dried under vacuum, and autoradiographed. After autoradiography, the distribution of radioactively labeled fragments was determined by Phosphorimager analysis (Molecular Dynamics). Alternatively, the relative intensities of dideoxy-terminated bands can be determined by scanning the autoradiograph using an instrument such as the SciScan 5000 imaging densitometer (United States Biochemical Corp).

When the set of four reactions (each containing a single ddNTP at an equimolar concentration as the dNTP) was carried out with each of the six DNA polymerases described above, the reactions with three of the DNA polymerases (T7 DNA polymerase Y526F, *E. coli* DNA polymerase I and Taq DNA polymerase) resulted in most (>50%) of the radioactivity in the primers that had been extended migrating at the top of the gel, corresponding to fragments greater than 300 bases in length. Based on the predicted exponential decay of signal with increasing fragment size, this corresponds to discrimination by these three DNA polymerases of more than 100 fold against all four ddNTPs. A more precise measurement of the discrimination against ddNTPs by these three DNA polymerases is obtained using the test in Example 7 below.

For the other three DNA polymerases (T7 DNA polymerase, E. coli DNA polymerase I F762Y and Taq DNA polymerase F667Y) the autoradiograph showed a series of dideoxy-terminated fragments with all of the reactions. In general, the average lengths of the labeled synthesized fragments were lowest for Taq DNA polymerase F667Y, with only about six radioactively labeled dideoxy-terminated fragments visible with even a several day exposure of the film. The average lengths of labeled fragments with E. coli DNA polymerase I F762Y are slightly longer than with Taq DNA polymerase F667Y, while the average lengths are significantly longer with T7 DNA polymerase. The fragments are more uniform in intensity when synthesized by E. coli DNA polymerase I F762Y and Taq DNA polymerase F667Y that by T7 DNA polymerase.

The distribution of radioactivity in the fragments was quantitated by Phosphoimager analysis (Molecular Dynamics). The total amount of labeled primers in each lane was determined by running three control reactions in which no DNA polymerase was present, and the radioactivity in each of the corresponding radioactive bands on the gel at the position of the unextended primer was determined. With some preparations of radioactively labeled primers, a certain percentage (<10%) is not extended by any of the DNA polymerases, regardless of the concentration of DNA polymerase used; this background level is determined by measuring the percentage of radioactivity remaining at the position of unextended primer for a series of four reactions containing ddNTPs, and subtracting the average of these four values from the total number of counts determined previously. This value is defined as the total number of counts in primers that are capable of being extended by a DNA polymerase.

The total number of counts (i.e. radioactivity) in the first three dideoxy-terminated fragments were determined for T7 DNA polymerase, E. coli DNA polymerase I F762Y and Taq DNA polymerase F667Y for each of the four ddNTP reactions. The values are presented in the Table below as the percentage of counts in the first three dideoxy-terminated fragments to the total number of counts in the primers capable of being extended by a DNA polymerase.

|  | Polymerase Reaction | | | |
| --- | --- | --- | --- | --- |
|  | ddGTP | ddATP | ddTTP | ddCTP |
| T7 DNA polymerase | 67% | 66% | 76% | 61% |
| E. coli DNA polymerase I F762Y | 95% | 92% | 96% | 92% |
| Taq DNA polymerase F667Y | 97% | 95% | 95% | 99% |

As a further test of the efficiency of each DNA polymerase to incorporate dideoxynucleotides, the number of counts in each fragment with a significant signal was determined for each reaction, and the data were plotted as a function of the fragment number using the Macintosh program Kaleidograph Version 3.0 (Synergy Software). The resulting plots were fit to an exponential decay curve using the Kaleidograph library routine for this function. The decay curve is given by the equation:

$$Y = e^{M*X}$$

where:

Y=1—(the fraction of labeled primers in fragments 1 to X compared to the total number of primers that can be extended)

X=the fragment number (the first dideoxy-terminated fragment is 1)

M=the exponential decay function calculated for the data by the Kaleidograph library routine.

In the Table below, the following data are provided for each of the four ddNTP reactions using T7 DNA polymerase, E. coli DNA polymerase I F762Y and Taq DNA polymerase F667Y:

N, the number of fragments used to fit each exponential curve.

M, the calculated exponential decay function as described above.

D, the discrimination factor given as the ratio of the use of a specific dNTP to the use of the comparable ddNTP when both nucleotides are present at equal concentrations. D is calculated from the equation above using the calculated value of M to determine Y when X=1, and defining D, the ratio of preference of the dNTP to the ddNTP, as Y/(1−Y).

$R^2$, the correlation index for the data, was calculated by the Kaleidograph library routine. This is a measure of the variability in band intensities, or the sequence-specific variability in the ability of a DNA polymerase to incorporate the specific dideoxynucleotide.

| Polymerase | ddNTP | N | M | D | $R^2$ |
| --- | --- | --- | --- | --- | --- |
| T7 DNA polymerase | ddGTP | 8 | −0.375 | 2.2 | 0.813 |
|  | ddATP | 6 | −0.356 | 2.3 | 0.996 |
|  | ddTTP | 5 | −0.450 | 1.8 | 0.997 |
|  | ddCTP | 8 | −0.317 | 2.7 | 0.889 |
| E. coli DNA polymerase I F762Y | ddGTP | 5 | −1.03 | 0.56 | 0.999 |
|  | ddATP | 5 | −0.860 | 0.72 | 0.998 |
|  | ddTTP | 5 | −1.06 | 0.54 | 1.000 |
|  | ddCTP | 6 | −0.842 | 0.75 | 1.000 |
| Taq DNA polymerase F667Y | ddGTP | 5 | −1.18 | 0.45 | 0.995 |
|  | ddATP | 6 | −0.997 | 0.59 | 0.997 |
|  | ddTTP | 6 | −1.01 | 0.56 | 0.996 |
|  | ddCTP | 4 | −1.44 | 0.32 | 0.996 |
| Averages: | | | | | |
| T7 DNA4 polymerase | ddNTP | | | 2.3 | .924 |
| E. coli DNA4 polymerase I | ddNTP | | | 0.64 | .999 |
| Taq DNA4 polymerase F667Y | ddNTP | | | 0.48 | .996 |

In summary, T7 DNA polymerase discriminates an average of 2.3 fold against ddNTPs, while E. coli DNA polymerase I F762Y and Taq DNA polymerase F667Y actually prefer ddNTPs over dNTPs an average of 1.6 fold (1/0.64) and 2.1 fold (1/0.48), respectively. A comparison of $R^2$ indicates that the intensity of neighboring fragments are more uniform with E. coli DNA polymerase I F762Y and Taq DNA polymerase F667Y than with T7 DNA polymerase. For a more accurate measure of uniformity, a greater number of fragments could be included in the analysis by reducing the level of ddNTPs (for example by 5 fold) in each reaction, reducing the decay in intensity at each position (see Example 13).

To determine the amount of discrimination against ddNTPs by a new DNA polymerase, reactions analogous to those described above would be carried out, and identical reactions would be carried out in parallel using T7 DNA polymerase (SEQUENASE Version 2.0, United States Biochemical Corporation), with all reactions analyzed on the same gel. An initial comparison of the distribution of dideoxy-terminated bands obtained with the new DNA polymerase compared with those obtained with T7 DNA polymerase would indicate whether the new DNA polymerase discriminated more or less against ddNTPs than T7 DNA polymerase. For example, such a visual inspection using *E. coli* DNA polymerase I F762Y clearly shows that for reactions with each of the 4 ddNTPs, the number of fragments visible on the gel in reactions using *E. coli* DNA polymerase I F762Y are less (and smaller in average size) than those using T7 DNA polymerase. A more quantitative analysis could then be carried out analogous to that described above in order to calculate the exponential decay factor (M), average relative rate of utilization of dNTPs relative to dNTPs (D) and variability in intensity ($R^2$) for the new DNA polymerase as described above.

One complication that can occur in this test is when the DNA polymerase has an associated exonuclease activity, such as the 5' to 3' exonuclease activity associated with Taq DNA polymerase and the 3' to 5' exonuclease activity associated with *E. coli* DNA polymerase I and native T7 DNA polymerase (not the Δ28 T7 DNA polymerase deletion mutant used in the experiments above). A 5' to 3' exonuclease activity is detrimental since it can remove the label on the 5' end of the primer, reducing the radioactivity signal being detected. This problem can be partially avoided by reducing the amount of DNA polymerase in the reaction mixture. In the example above, 0.025 units of Taq DNA polymerase resulted in virtually all of the primers being extended until terminated by incorporation of a dideoxynucleotide, without appreciable loss in radioactivity due to 5' to 3' exonuclease activity, whereas a 40 fold increase in Taq DNA polymerase activity, or 1 unit per reaction, resulted in the loss of virtually all $^{32}$P from the 5' ends of the primer. An alternative approach to measuring the extent of discrimination for a DNA polymerase with a 5' to 3' exonuclease activity is to use a different assay such as those described in Examples 8–10.

A 3' to 5' exonuclease activity can complicate the assay described above by making the DNA polymerase appear to discriminate more against a ddNTP than it actually does (for example, see Tabor and Richardson, 86 *Proc. Natl. Acad. Sci.* 4076, 1987). This is because once a dideoxynucleotide has been incorporated, the exonuclease activity can preferentially remove the dideoxynucleotide so that DNA synthesis can continue, resulting in an increase in the length of the fragment. Preferably, the enzymes assayed in the test described above are devoid of such 3' to 5' exonuclease activity; examples are modified T7 DNA polymerase (Sequenase®, United States Biochemical Corporation), Taq DNA polymerase, exonuclease-deficient Vent (*Thermococcus litoralis*) DNA polymerase (New England Biolabs catalog number 257), exonuclease-deficient Deep Vent (Pyrococcus GB-1) DNA polymerase (New England Biolabs catalog number 259), exonuclease-deficient Pfu (*Pyrococcus furiosus*) DNA polymerase (Stratagene catalog number 600163), and exonuclease-deficient Klenow fragment (*E. coli* DNA polymerase I, United States Biochemical Corporation, catalog number 70057). In some instances, such as with *E. coli* DNA polymerase I (Klenow fragment) the 3' to 5' exonuclease activity is weak and does not interfere significantly with this assay (see for example Tabor and Richardson 264 *J. Biol. Chem.* 6447, 1989). One method to determine whether a new DNA polymerase being tested has a 3' to 5' exonuclease activity that is interfering with the ability to accurately measure the discrimination against ddNTPs is to carry out the experiment described above, removing aliquots at different time points up to 60 min. If the size distribution of the dideoxy-terminated fragments increases with time, then it is likely that such a 3' to 5' exonuclease activity is interfering with the assay, while if the distribution of fragments is constant over time then such an activity is not having a significant effect. If the average fragment length is increasing with time, then one should use a shorter incubation time and/or decrease the DNA polymerase concentration to a range in which the fragment sizes remain constant with time.

Pyrophosphorolysis, or the reversal of the polymerase reaction, can have a similar effect as the 3' to 5' exonuclease activity, allowing the DNA polymerase to remove the chain terminating dideoxynucleotide and further increase the length of the fragments (see Tabor and Richardson, 265 *J. Biol. Chem.* 8322, 1990). This activity is readily avoided by including pyrophosphatase in the reaction mixture, in order to remove the pyrophosphate that accumulates during DNA synthesis and is a necessary substrate for pyrophosphorolysis.

Example 7

Gel Electrophoresis-based Determination of the Rate of Incorporation of Dideoxynucleotides Relative to Deoxynucleotides by Varying the Ratio of dNTPs to ddNTPs This example is similar to that described in Example 6. While it is the preferred test for DNA polymerases that discriminate strongly against the incorporation of dideoxynucleotides (e.g. T7 DNA polymerase Y526F, *E. coli* DNA polymerase I and Taq DNA polymerase), it also works well with DNA polymerases that efficiently incorporate ddNMPs (e.g. T7 DNA polymerase, *E. coli* DNA polymerase I mutant F762Y and Taq DNA polymerase mutant F667Y). In this test, the ratio of ddNTP to dNTP is varied for two different DNA polymerase preparations, keeping all other aspects of the reactions identical, and the distributions of dideoxy-terminated radioactively labeled fragments are compared to determine the ratios required for the two DNA polymerases being tested to obtain fragments of comparable average length.

The average length of a series of fragments is determined in one of two ways. In the first, which is best for DNA polymerases that incorporate ddNMPs efficiently, one inspects the autoradiograph and determines the position of the largest fragments visible on a given exposure for a series of reactions containing ddNTP:dNTP ratios that vary by two-fold increments using one DNA polymerase, and compares that to an analogous series using the second DNA polymerase, to determine the ratios required to generate fragments of comparable size for the two DNA polymerases. The position of the front marking the appearance of visible radioactive bands is usually relatively sharp and readily observed by eye. However, it is also possible to determine such positions more precisely using the Phosphoimager to locate the position in each lane where a certain threshold of radioactivity per unit area occurs, starting at the top of the gel and moving down the gel.

Some DNA polymerases discriminate very strongly against the incorporation of dideoxynucleotides, in which case it is difficult to add sufficient ddNTPs to the reaction to clearly detect the position of the largest dideoxy-terminated fragments on a denaturing polyacrylamide gel. For such DNA polymerases, one can use an alkaline agarose gel electrophoresis to compare the lengths of the dideoxy-terminated fragments in the different series. If one uses a denaturing polyacrylamide gel, then an alternative method to determine the ratios of ddNTP:dNTP required for the two DNA polymerases to generate dideoxy-terminated fragments of comparable average lengths is to focus on one or several bands and determine the ratio of ddNTPs to dNTPs required to obtain a specific level of radioactivity in those fragments, as analyzed by the Phosphoimager, for the two DNA polymerases being tested.

These tests were carried out using the six DNA polymerases described in Example 6. The reaction conditions were identical to that described in Example 6 except for the concentrations of dNTPs and ddNTPs. All reaction mixtures contained 10 μM 4 dNTPs. Each of the four ddNTP concentrations were varied by two-fold increments in the following ranges for the six DNA polymerases as follows: T7 DNA polymerase, E. coli DNA polymerase I F762Y, and Taq DNA polymerase F667Y, 0.02 μM to 1 μM, and T7 DNA polymerase Y526F, E. coli DNA polymerase I and Taq DNA polymerase, 100 to 2,000 μM. The reactions were carried out and the samples were analyzed by denaturing polyacrylamide gel electrophoresis as described in Example 6. Drying of the gel, autoradiography, and Phosphoimager analysis were as described in Example 6. The Table below summarizes the results from this experiment; the values shown for T7 DNA polymerase, E. coli DNA polymerase I F762Y, and Taq DNA polymerase F667Y are the absolute ratios obtained in Example 6 by statistical analysis of the rate of exponential decay in intensity of dideoxy-terminated fragments obtained using a 1:1 ratio of dNTPs to ddNTPs. The values obtained for T7 DNA polymerase Y526F, E. coli DNA polymerase I and Taq DNA polymerase were obtained by determining the ratios of ddNTP to dNTP required to generate a series of dideoxy-terminated fragments of comparable average length to a series generated using T7 DNA polymerase, E. coli DNA polymerase I F762Y, and Taq DNA polymerase F667Y, respectively; i.e., for each pair of wild-type and mutant DNA polymerases the ratios of ddNTPs:dNTPs were determined that give a comparable distribution of dideoxy-terminated fragments. The ddNTP:dNTP ratio used in the reaction with the strongly discriminating enzyme (i.e. the one that contains phenylalanine at the critical position) divided by the ddNTP:dNTP ratio used to obtain a comparable distribution of dideoxy-terminated fragments with the relatively non-discriminating enzyme (i.e. the one that contains tyrosine at the critical position) gives a factor that corresponds to the difference in efficiency between the two DNA polymerases in their use of ddNTPs relative to the comparable dNTP. This factor was multiplied by the absolute ratios obtained for T7 DNA polymerase, E. coli DNA polymerase I F762Y, and Taq DNA polymerase F667Y in Example 6 in order to obtain the values shown below for T7 DNA polymerase Y526F, E. coli DNA polymerase I and Taq DNA polymerase, respectively.

| | Polymerase Incorporation Rate Ratios | | | |
|---|---|---|---|---|
| | dG/ddG | dA/ddA | dT/ddT | dC/ddC |
| T7 DNA polymerase | 3.2 | 3.3 | 2.8 | 3.7 |
| T7 DNA polymerase Y526F | 6,400 | 7,300 | 8,400 | 11,000 |
| E. coli DNA polymerase I | 140 | 720 | 1,100 | 250 |
| E. coli DNA polymerase I F762Y | 0.56 | 0.72 | 0.54 | 0.75 |
| Taq DNA | 1,400 | 4,700 | 4,500 | 2,600 |

| | Polymerase Incorporation Rate Ratios | | | |
|---|---|---|---|---|
| | dG/ddG | dA/ddA | dT/ddT | dC/ddC |
| polymerase Taq DNA polymerase F667Y | 0.45 | 0.59 | 0.56 | 0.32 |

The Table below summarizes the effect of having tyrosine in place of phenylalanine at the critical selectivity residue of T7 DNA polymerase, E. coli DNA polymerase I and Taq DNA polymerase on the use of ddNTPs relative to dNTPs.

| Polymerase | Residue | Average Rate dN/ddN | Improvement in Use of ddNTPs |
|---|---|---|---|
| T7 DNA polymerase | Tyrosine (WT) | 3.0 | 3,000 × |
| | Phenylalanine | 8,000 | |
| E. coli DNA polymerase I | Phenylalanine (WT) | 600 | |
| | Tyrosine | 0.6 | 1,000 × |
| Taq DNA polymerase | Phenylalanine (WT) | 3,000 | |
| | Tyrosine | 0.5 | 6,000 × |

To use this test to determine the extent of discrimination of a new DNA polymerase, reactions would be carried out as described above initially using a wide range of ratios of ddNTPs to dNTPs, and comparing the distribution of dideoxy-terminated fragments on a denaturing polyacrylamide gel to those of a standard, e.g. T7 DNA polymerase. Matching the lanes that have comparable average lengths of DNA fragments, the ratio of ddNTPs:dNTPs of the new DNA polymerase is divided by the ratio used with T7 DNA polymerase to give the level of discrimination against ddNTPs by the new DNA polymerase relative to T7 DNA polymerase.

To use this test to determine whether the modification of a DNA polymerase results in a decrease in its ability to discriminate against ddNTPs (i.e. incorporate dideoxynucleotides more efficiently), an identical number of units of modified and unmodified DNA polymerases would be used in a series of reactions containing varying ratios of ddNTPs to dNTPs as described above. The average length of dideoxy-terminated fragments are compared for identical ratios of ddNTPs to dNTPs for the two enzymes. If the modification has resulted in a DNA polymerase that incorporates dideoxynucleotides more efficiently, the average length of dideoxy-terminated fragments will be shorter for reactions using the modified DNA polymerase compared with those using the unmodified DNA polymerase at the same ratios of ddNTP to dNTP, while the average length will be longer for reactions using the modified DNA polymerase if the modification resulted in a DNA polymerase that is more discriminatory towards ddNTPs.

This test can also be used to determine whether a modification of a DNA polymerase results in a decrease in its ability to discriminates against analogs of ddNTPs, for example fluorescently tagged ddNTPs. This is possible even if one does not know the concentration of the analogs being tested. As an example of this, we compared the ability of Taq DNA polymerase and Taq DNA polymerase F667Y to use each of the four DyeDeoxy Terminators manufactured by Applied Biosystems (part number 401150). These DyeDeoxy Terminators have four different fluorescent moieties covalently bound to each of the four ddNTPs (see Example 12 for more detail). For each of the DyeDeoxy Terminators, the ratio of dNTPs to DyeDeoxy Terminators was varied over a 16,000 fold range by intervals of two-fold, and the pattern of dideoxy-terminated fragments was compared on the autoradiograph to determine the ratios required for each of the two enzymes to obtain the same average length of dideoxy-terminated fragments. The Table below summarizes these results. For each Terminator, the column labeled "Ratio" represents the ratio of the ratios of ddNTP to dNTP required to give fragments of identical average length for Taq DNA polymerase versus Taq DNA polymerase F667Y. As with normal ddNTPs, Taq DNA polymerase F667Y incorporates the fluorescent ddNTP derivatives much more efficiently that does the unmodified Taq DNA polymerase, by at least a factor of 400.

| DyeDeoxy Terminator | Ratio |
| --- | --- |
| G Terminator | >400 |
| A Terminator | >2,000 |
| T Terminator | >2,000 |
| C Terminator | >2,000 |

As discussed previously, one complication that can arise in the use of this test is when the DNA polymerase being tested has an associated exonuclease activity. The problems that 5' to 3' and 3' to 5' exonucleases can cause and ways to minimize their effects when present are discussed in Example 6. When testing to determine whether the modification of a polymerase decreases its ability to incorporate dideoxynucleotides, one class of mutants that can have this effect are ones that inactivate a normally very active 3' to 5' exonuclease activity (see for example Tabor and Richardson 84, Proc. Natl. Acad. Sci. 4767, 1987). This class of mutants are not claimed in this patent. If one has a modified DNA polymerase that gives an apparent increase in the ability of the DNA polymerase to incorporate dideoxynucleotides, and one wants to determine whether it is in the polymerase domain or the exonuclease domain, it is necessary to carry out an exonuclease assay on the modified and unmodified forms of the enzyme; a mutation that affects primarily the exonuclease activity of the enzyme will have a greater effect on the exonuclease activity of the enzyme than on the polymerase activity. Preferably, one would measure the exonuclease activity on a DNA substrate labeled at its 3' end with $^{32}$P-ddAMP (see Example 21). As in Example 6, it is important to inhibit pyrophosphorolysis in these reactions in order to avoid it increasing the apparent discrimination against ddNTPs by a DNA polymerase. This is readily accomplished by including pyrophosphatase in the reaction.

Example 8

Determination of the Efficiency of Incorporation of Dideoxynucleotides by Inhibition of DNA Synthesis on a Single-Stranded M13 DNA - Unlabeled 40-mer Primer Complex In this example the sensitivity of a DNA polymerase to a ddNTP is determined by measuring the ability of varying concentrations of the ddNTP to inhibit a standard DNA synthesis reaction. The DNA synthesis assay is a modification of that described in Tabor and Richardson 264 *J. Biol. Chem.* 6447, 1989. The 40-mer primer and the M13 mGP1-2 template are as described in Example 3. The primer is annealed to the M13 mGP1-2 single-stranded DNA template in a reaction mixture (1X=25 μl) containing 2 μg of M13 mGP1-2 DNA, 6 pmoles of primer (a 10-fold molar excess to template), 40 mM Tris.HCl, pH 8.0, 10 mM MgCl$_2$ and 100 mM NaCl. The mixture is incubated 65° C. for 2 min and then cooled to room temperature over 30 min. The standard reaction mixture (45 μl) contained 22 mM Tris.HCl, pH 8.0, 5.5 mM MgCl$_2$, 55 mM NaCl, 300 μM dGTP, dATP, dCTP and [$^3$H]TTP (30 cpm/pmol), and varying concentrations of one of the four or all four ddNTPs. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 μl aliquots of dilutions (0.01 to 1 unit) of the DNA polymerase being analyzed, diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 μl of 100 mM EDTA, and 45 μl is spotted onto Whatman DE81 filter discs. The discs are washed in 4 changes of 150 ml of 0.3M ammonium formate, pH 8.0, followed by 2 changes of 150 ml of 90% ethanol, each of 5–10 min duration. The disks are then dried under a heat lamp and counted in a scintillation counter in the presence of 5 ml of fluor (Opti-Fluor O, Packard). From the amount of radioactivity on each disk, the amount of total DNA synthesis is calculated.

Specific DNA polymerases being tested may have optimum buffer, pH, salt, or temperature conditions that differ from those suggested above. Each DNA polymerase should be tested under the conditions that give optimum specific polymerase activity for that enzyme.

To determine whether a modification of a given DNA polymerase results in a decrease in its ability to discriminate against dideoxynucleotides, first a series of reactions are carried out in the absence of ddNTPs, varying the DNA polymerase concentration to determine the range where the activity varies approximately linearly with enzyme concentration for both the modified and unmodified forms of the enzyme. An enzyme concentration is chosen that is in this linear range for both forms of the enzyme; e.g., an enzyme concentration whereby about 30% of the template is replicated in the 10 min reaction is likely to be in such a linear range.

Once a proper enzyme concentration is chosen, a series of reactions are carried out varying the amount of either one ddNTP or preferably all four ddNTPs in the mixture, in order to determine the concentration required to inhibit 50% of the DNA synthesis. For example, under the conditions stated above (300 μM 4 dNTPs), the following concentrations of a mixture of 4 ddNTPs are required to inhibit 50% of the DNA synthesis for the following six DNA polymerases:

| Polymerase | [4ddNTP] for 50% inhibition |
| --- | --- |
| T7 DNA polymerase | 0.1 μM |
| T7 DNA polymerase Y526F | 300 μM |
| E. coli DNA polymerase I | 20 μM |
| E. coli DNA polymerase I F762Y | 0.04 μM |
| Taq DNA polymerase | 150 μM |
| Taq DNA polymerase F667Y | 0.4 μM |

This test can be used to determine if a modification in a new DNA polymerase results in a decrease in its ability to discriminate against ddNTPs; if the mutation does have this effect, then a higher concentration of 4 ddNTPs will be required to inhibit 50% of the DNA synthesis in the assay described above.

Example 9

Determination of the Efficiency of Incorporation of Dideoxynucleotides by Measuring the Incorporation of [α-$^{32}$P]dAMP into Synthetic Primer-Template Complexes

In this example the competition between a dNTP and a ddNTP is assayed for use at a single site in a synthetic primer-template. This assay differs from the others in that it limits the comparison of the use of the two substrates to a single site, avoiding the complication of sequence-specific variability in discrimination. While this relatively simple assay is suitable for a preliminary screen of DNA polymerases for their ability to discriminate against ddNTPs, it should not be used to the exclusion of the assays presented in Examples 6–8 since often the discrimination against ddNTPs is strongly influenced by the neighboring sequences, an important problem for DNA sequence analysis (see for example Tabor and Richardson 265 *J. Biol. Chem.* 8322, 1990).

The two primer-templates shown below are used in this example. The first is used to determine the discrimination between dATP versus ddATP, while the second is used to determine the discrimination between dCTP versus ddCTP, dTTP versus ddTTP, and dGTP versus ddGTP.

Primer-Template A:

| | |
|---|---|
| 5' GGCGACGTTGTAAAACGACGGCCAGTGCCA 3' | SEQ ID NO: 27 |
| 3' GCTGCAACATTTTGCTGCCGGTCACGGTTCCCC 5' | SEQ ID NO: 28 |

Primer-Template B:

| | |
|---|---|
| 5' GGCGACGTTGTAAAACGACGGCCAGTGCCA 3' | |
| 3' GCTGCAACATTTTGCTGCCGGTCACGGTCAGTTTT 5' | SEQ ID NO: 29) |

Each reaction mixture contains 25 pmoles each of primer and template. The primer and template are mixed together and annealed in a reaction mixture (1X=10 μl) containing 40 mM Tris.HCl, pH 8.0, 10 mM MgCl$_2$ and 100 mM NaCl. The mixture is incubated 65° C. for 2 min and then cooled to room temperature over 30 min. The standard reaction mixture (45 μl) for reactions carried out with Primer-Template A contains 22 mM Tris.HCl, pH 8.0, 5.5 mM MgCl$_2$, 55 mM NaCl, 25 pmoles of the Primer-Template A complex, 5 μM [α-$^{32}$P]dGTP (4,000 cpm/pmole) and varying concentrations of dATP and ddATP. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 μl of 100 mM EDTA, and 45 μl is spotted onto Whatman DE81 filter discs. The discs are washed in 4 changes of 150 ml of 0.3M ammonium formate, pH 8.0, followed by 2 changes of 150 ml of 90% ethanol, each of 5–10 min duration. The disks are then dried under a heat lamp and counted in a scintillation counter in 5 ml of fluor (Opti-Fluor O, Packard). From the amount of radioactivity on each disk, the amount [$^{32}$P] dGMP incorporated was determined. The assumption is made once a single dAMP residue has been incorporated to remove the block for the incorporation of dGMP residues, four [$^{32}$P]dGMPs will be incorporated into each primer, and thus the number of dAMPs incorporated are one fourth the number of dGMPs incorporated.

All reactions are carried out with a constant amount of the DNA polymerase being analyzed; the amount of DNA polymerase should be sufficient to replicate 50% of the total dCMP residues in the single-stranded region of the template in the 10 min incubation in the presence of 10 μM dATP and the absence of ddATP. Specific DNA polymerases being tested may have optimum buffer, pH, salt, or temperature conditions that differ from those suggested above. Each DNA polymerase should be tested under the conditions that give optimum specific polymerase activity for that enzyme. Control reactions should also be carried out in which neither dATP nor ddATP are present; this defines the background DNA synthesis that should be subtracted from each sample. In general this is less than 10% of the DNA synthesis obtained when dATP is present.

Reactions are then carried out with 10 μM dATP and varying concentrations of ddATP, to determine the amount of ddATP required to inhibit DNA synthesis by 50%. Examples are shown in the Table below for the concentration of ddATP required to inhibit 50% of the DNA synthesis in the presence of 10 μM dATP. The polymerases are defined as in Example 6.

| Polymerase | [ddATP] for 50% inhibition |
|---|---|
| T7 DNA polymerase | ~30 μM |
| T7 DNA polymerase Y526F | >500 μM |
| *E. coli* DNA polymerase I | >500 μM |
| *E. coli* DNA polymerase I F762Y | ~6 μM |
| Taq DNA polymerase | >500 μM |
| Taq DNA polymerase F667Y | ~5 μM |

In order to carry out an analogous test measuring the discrimination against ddGTP, ddTTP or ddCTP, reactions are carried out identical to that described above except that Primer-Template B is used instead of Primer-Template A, and the reactions containing 10 μM dGTP, dTTP and dCTP and 5 μM [α-$^{32}$P]dATP (4,000 cpm/pmole) and varying concentrations of either ddGTP, ddTTP or ddCTP.

As with the other examples, DNA polymerases with a 3' to 5' exonuclease activity can interfere with this assay, making an enzyme more discriminatory against ddNTPs than that due to discrimination at the level of incorporation of the analog. In addition, enzymes with high levels of exonuclease activity can use up all the dNTPs in the reaction mixture (especially with the relatively low level of dNTPs present in these reactions), resulting in no net DNA synthesis (e.g. the native T7 DNA polymerase, see Tabor and Richardson 264 *J. Biol. Chem.* 6447, 1989). In these cases the concentration of DNA polymerase and the incubation time of the reaction should be adjusted to obtain the maximum level of DNA synthesis in the absence of ddNTPs.

Example 10

Determination of the Efficiency of Incorporation [α-$^{32}$P]ddNMPs into a Synthetic Primer-Template Complex In this example the competition between a dNMP and a ddNMP is assayed for incorporation at a single site in a synthetic primer-template. This assay differs from that in Example 9 in that the label is in [α-$^{32}$P]ddATP, and thus the incorporation of ddAMP is being measured. This assay can be used to test whether a ddNTP is inhibiting a DNA polymerase by acting as a chain terminator, being incorporated into the 3' end of the primer, or simply by binding the DNA polymerase and preventing further DNA synthesis without actually being incorporated into the primer.

In the example below the incorporation of ddAMP is measured using [α-$^{32}$P]ddATP and Primer-Template A (Example 9):

| Primer-Template A: | |
|---|---|
| 5' GGCGACGTTGTAAAACGACGGCCAGTGCCA 3' | SEQ ID NO: 27 |
| 3' GCTGCAACATTTTGCTGCCGGTCACGGTTCCCC 5' | SEQ ID NO: 28 |

Incorporation of [α-$^{32}$P]ddGMP, [α-$^{32}$P]ddCMP and [α-$^{32}$P]ddTMP could be similarly tested on the appropriate template (for example, Primer-Template B in Example 9).

Each reaction mixture contains 25 pmoles each of primer and template (Primer-Template A, see above). The primer and template are mixed together and annealed in a reaction mixture (1X=10 µl) containing 40 mM Tris.HCl, pH 8.0, 10 mM MgCl$_2$ and 100 mM NaCl. The mixture is incubated 65° C. for 2 min and then cooled to room temperature over 30 min. The standard reaction mixture (45 µl) contains 22 mM Tris.HCl, pH 8.0, 5.5 mM MgCl$_2$, 55 mM NaCl, 25 pmoles of the Primer-Template A complex, 2.5 µM [α-$^{32}$P]ddATP (Amersham PB10235, >5000 Ci/mmol diluted with cold ddATP to a specific activity of 4,000 cpm/pmole) and varying concentrations of dATP. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 5 µl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are terminated by the addition of 5 µl of 100 mM EDTA, and 45 µl is spotted onto Whatman DE81 filter discs. The discs are washed in 4 changes of 150 ml of 0.3M ammonium formate, pH 8.0, followed by 2 changes of 150 ml of 90% ethanol, each of 5–10 min duration. The disks are then dried under a heat lamp and counted in a scintillation counter 5 ml of fluor (Opti-Fluor O, Packard). From the amount of radioactivity on each disk, the amount [$^{32}$P] ddAMP incorporated is determined.

All reactions are carried out with a constant amount of the DNA polymerase being tested; the amount of DNA polymerase should be that concentration which gives the highest level of incorporation of [$^{32}$P]ddAMP into Primer-Template A in the 10 min incubation in the absence of dATP. Specific DNA polymerases being tested may have optimum buffer, pH, salt, or temperature conditions that differ from those suggested above. Each DNA polymerase should be tested under the conditions that give optimum specific polymerase activity for that enzyme.

In order to use this assay to determine the level of discrimination against a ddNTP, reactions are carried out with a constant amount of the DNA polymerase and [$^{32}$P] ddATP, in the presence or absence of 2.5 µM dATP (an equimolar concentration to [$^{32}$P]ddATP) and the effect the presence of dATP has on the incorporation of [$^{32}$P]ddAMP is determined. If a DNA polymerase does not discriminate between the incorporation of ddAMP and dAMP, and it has no 3' to 5' exonuclease activity, then the addition of dATP will inhibit incorporation of [$^{32}$P]ddAMP by 50%.

This test is best for a DNA polymerase that efficiently incorporates ddNMPs, such as Taq DNA polymerase F667Y. For DNA polymerases that discriminate strongly against ddNMPs, the previous assay is preferred, in which the label is in a dNTP other than the one being used in competition with the ddNTP, since in that case much higher concentrations of the ddNTP can be used. However, with DNA polymerases that discriminate strongly against ddNMPs, if one is interested in testing whether a given mutation is reducing the level of discrimination against ddNMPs, this assay could be used by assaying the unmodified DNA polymerase on this substrate in the absence of dATP (measuring the incorporation of [$^{32}$P]ddAMP as a function of DNA polymerase concentration), and comparing the rate of incorporation to that of the mutant enzyme. If the mutation is reducing the discrimination against ddATP, then the mutant enzyme should have a higher specific activity for incorporation of [$^{32}$P]ddAMP.

As with the other examples, DNA polymerases with a 3' to 5' exonuclease activity can interfere with this assay, making an enzyme more discriminatory against ddNTPs than that due to discrimination at the level of incorporation of the analog. And as in Example 9, enzymes with high levels of exonuclease activity can deplete all the dNTPs, resulting in no net incorporation of [$^{32}$P]ddAMP. In these cases the concentration of DNA polymerase and the incubation time of the reaction should be adjusted to obtain the maximum level of incorporation of [$^{32}$P]ddAMP by the DNA polymerase being tested.

All of the above methods are based on radioactivity to detect either the length of the extended primer or the amount of DNA synthesis on the primer. The efficiency of incorporation of dideoxynucleotides by a DNA polymerase can also be measured nonradioactively. Two examples are presented below that make use of either fluorescent primers or fluorescent dye-dideoxy terminators that are detected on an Applied Biosystems Model 373A DNA Sequencing System.

Example 11

Determination of the Efficiency of Incorporation of Dideoxynucleotides Using a Fluorescent Primer Annealed to Single-Stranded DNA and Gel Electrophoresis In this example a fluorescently labeled primer is annealed to single-stranded DNA and DNA synthesis reactions are carried out using varying ratios of dNTPs to ddNTPs. The samples are then loaded onto an Applied Biosystems Model 373A DNA Sequencing System, and the length of each fluorescent fragment is determined by direct fluorescent detection during gel electrophoresis. Reactions are carried out as described in Tabor and Richardson 265 *J. Biol. Chem.* 8322, 1990. The fluorescent primer used is "Fam" primer (Applied Biosystems). The DNA used is single-stranded M13 mGP1-2 DNA as described in Example 3. The primer is annealed to the M13 mGP1-2 single-stranded DNA template in a reaction mixture (1X=10 μl) containing 2 μg of M13 mGP1-2 DNA, 5 ng of primer, 40 mM Tris.HCl, pH 8.0, 10 mM $MgCl_2$ and 100 mM NaCl. The mixture is incubated 65° C. for 2 min and then cooled to room temperature over 30 min. The standard reaction mixture (18 μl) contains 22 mM Tris.HCl, pH 8.0, 5.5 mM $MgCl_2$, 55 mM NaCl, and varying concentrations of the 4 dNTPs and one of the four ddNTPs. The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 2 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are by the addition of 8 μl of 20 mM DTPA, 1M potassium acetate, pH 5.0, and 60 μl of ethanol. After centrifugation, the DNA is resuspended in 6 μl of 80% formamide, 10 mM Tris.HCl, pH 8.0, and 1 mM EDTA, and heated at 80° C. for 2 min immediately prior to loading on the polyacrylamide gel on the Applied Biosystems 373A DNA Sequencing System following the manufacturer's procedures.

Specific DNA polymerases being tested may have optimum buffer, pH, salt, or temperature conditions that differ from those suggested above. Each DNA polymerase should be tested under the conditions that give optimum specific polymerase activity for that enzyme. The concentration of DNA polymerase should be sufficient to extend most of the primers at least several hundred nucleotides or until a dideoxynucleotide has been incorporated in the 10 min reaction.

The ratio of dNTPs to ddNTPs is adjusted to obtain optimum peak intensities for approximately three hundred bases. For example, for Taq DNA polymerase approximately 10 μM 4 dNTPs and 200–600 μM ddNTPs is optimal, while for Taq DNA polymerase F667Y approximately 300 μM 4 dNTPs and 0.5–5 μM ddNTPs is optimal.

To determine whether a modification of a given DNA polymerase results in a decrease in its ability to discriminate against dideoxynucleotides, reactions should be carried out at varying ratios of dNTPs to ddNTPs for both the unmodified and modified DNA polymerases, and the intensities of dideoxy-terminated fragments of different lengths are compared to determine whether the modified DNA polymerase is using ddNTPs more efficiently than the unmodified enzyme.

Example 12

Determination of the Efficiency of Incorporation of Fluorescent Dideoxynucleotides by Gel Electrophoresis In this example a nonfluorescent primer is annealed to single-stranded DNA and DNA synthesis reactions are carried out using varying ratios of dNTPs to a single fluorescently labeled-ddNTP. The samples are then loaded onto an Applied Biosystems Model 373A DNA Sequencing System, and the length of each fluorescent fragment is determined by direct fluorescent detection during gel electrophoresis. The primer used in this example is the 40-mer described in Example 3, and the template is the single-stranded M13 mGP1-2 described in Example 3. The primer is annealed to the M13 mGP1-2 single-stranded DNA template in a reaction mixture (1X=10 μl) containing 2 μg of M13 mGP1-2 DNA, 6 pmoles of primer (a 10-fold molar excess to template), 40 mM Tris.HCl, pH 8.0, 10 mM $MgCl_2$ and 100 mM NaCl. The mixture is incubated 65° C. for 2 min and then cooled to room temperature over 30 min. The standard reaction mixture (18 μl) contains 22 mM Tris.HCl, pH 8.0, 5.5 mM $MgCl_2$, 55 mM NaCl, and varying concentrations of the 4 dNTPs plus one of the four fluorescently-labeled ddNTPs. The four fluorescently labeled ddNTPs are from Applied Biosystems (Taq DyeDeoxy Terminator Cycle Sequencing Kit, part number 401150), and are referred to as G, A, T or C "DyeDeoxy Terminators" (manual for Taq DyeDeoxy Terminator Cycle Sequencing Kit, part number 901497, Rev. E). The reaction mixtures also contained 10 ng of yeast inorganic pyrophosphatase to inhibit pyrophosphorolysis that could otherwise increase the apparent discrimination by the DNA polymerase (Tabor and Richardson 265 *J. Biol. Chem.* 8322, 1990). The mixtures are incubated at 37° C. for 1 min (70° C. for thermophilic DNA polymerases), and the reactions are initiated by the addition of 2 μl aliquots (0.01 to 1 unit) of the DNA polymerase being analyzed diluted in 20 mM Tris.HCl, pH 7.5, 10 mM 2-mercaptoethanol and 0.05% bovine serum albumin. The reaction mixtures are further incubated at 37° C. for 10 min (70° C. for thermophilic DNA polymerases). The reactions are by the addition of 8 μl of 20 mM EDTA, 1M potassium acetate, pH 5.0, and 60 μl of ethanol. After centrifugation, the DNA is resuspended in 6 μl of 80% formamide, 10 mM Tris.HCl, pH 8.0, and 1 mM DTPA, and heated at 80° C. for 2 min immediately prior to loading on the polyacrylamide gel on the Applied Biosystems 373A DNA Sequencing System following the manufacturer's procedures.

Specific DNA polymerases being tested may have optimum buffer, pH, salt, or temperature conditions that differ from those suggested above. Each DNA polymerase should be tested under the conditions that give optimum specific polymerase activity for that enzyme. The concentration of DNA polymerase used in these reactions should be that concentration that is sufficient to extend most of the primers at least several hundred nucleotides or until a dideoxynucleotide has been incorporated in the 10 min reaction. For DNA polymerases that have a 5' to 3' exonuclease activity, such as Taq DNA polymerase, the DNA polymerase concentration must be kept low enough to avoid this activity degrading a significant percentage of the 5' ends of the fragments.

To determine whether a DNA polymerase discriminates strongly or weakly against a fluorescent ddNTP, reactions are carried out using 20 μM dNTPs and 0.01 μl of each DyeDeoxy Terminator provided by Applied Biosystems (part number 401150). When Taq DNA polymerase is used under these conditions, most of the fluorescence is either in unincorporated dye-ddNTPs at the leading front of the gel, or in fragments greater than several hundred bases in length. In contrast, with the Taq DNA polymerase mutant F667Y, under these conditions most of the fluorescence is in fragments that are less than several hundred bases in length, and a significantly lower percentage of the total fluorescence is in unincorporated dye-ddNTPs at the leading front of the gel.

To determine whether a modification of a given DNA polymerase results in a decrease in its ability to discriminate against dideoxynucleotides, reactions are carried out at varying ratios of dNTPs to DyeDeoxy Terminators for both the unmodified and modified DNA polymerases, and the average length of the resulting fluorescent fragments are compared to determine whether the modified DNA polymerase is using the DyeDeoxy Terminators more efficiently than the unmodified enzyme.

The following examples provide tests for determining the uniformity of band intensities produced from dideoxy-terminated fragments synthesized by different DNA polymerases.

Example 13

Determination of Uniformity of Incorporation of Dideoxynucleotides Using a Single-Stranded M13 DNA - 5' $^{32}$P-labeled 40-mer Primer Complex and Gel Electrophoresis In this example the uniformity of dideoxynucleotide incorporation is measured on a 5' $^{32}$P-end labeled primer extended on a single-stranded M13 DNA template. Three activities can cause variability in band intensity of dideoxy-terminated fragments. One is exonuclease activity that can preferentially at some sequences; this is avoided by removal of the activity selectively either by chemical or genetic means (see for example Tabor and Richardson 264, *J. Biol. Chem.* 6447, 1989). The second is pyrophosphorolysis; this is readily avoided by including pyrophosphatase in the reaction mixture, which degrades the pyrophosphate that accumulates during DNA synthesis and is a necessary substrate for pyrophosphorolysis. The third is sequence-specific variability in the incorporation of dideoxynucleotides. Variability in band intensity is detrimental to DNA sequence analysis, decreasing the accuracy of the DNA sequence determined. This test is designed to compare the degree of variability in band intensities in fragments synthesized by different DNA polymerases, including mutant DNA polymerases that may incorporate dideoxynucleotides more efficiently.

The primer, template and reaction conditions in this Example are identical to that described in Examples 6 and 7. The template is M13 mGP1-2 single-stranded DNA described in Example 3, and the primer is the 40 mer also described in Example 3. Reaction conditions used are those that are optimum for the DNA polymerase being tested with regard to buffer, pH, salts, and temperature of the reaction. It is preferred that magnesium is the only metal ion present in the reaction mixture (i.e. the reactions are carried out in the absence of added manganese ions). A concentration of DNA polymerase is chosen whereby most of the primers are extended in a 10 min reaction and are terminated by the incorporation of a dideoxynucleotide. The ratios of dNTPs to ddNTPs are adjusted for the specific DNA polymerase being tested so that the average fragment size is approximately 100–300 nucleotides. ddCTP is the preferred ddNTP to use for the test of uniformity since fragments terminated with this dideoxynucleotide tend to have the most variability in intensities (see for example Tabor and Richardson 86 *Proc. Natl. Acad. Sci.* 4076, 1989). Gel electrophoresis, autoradiography, and analysis of the band intensities by either scanning of the gel or phosphoimager analysis are as described in Example 6. Electrophoresis is carried out until fragments of approximately 55 nucleotides in length are at the bottom of the gel (the dye bromphenol blue has run off the bottom of the gel and the dye xylene cyanol is approximately 8 cm from the bottom of the gel).

For a given series of ddNMP-terminated fragments, for example a series of ddCMP-terminated fragments, the intensities of the first 20 fragments from the bottom of the gel are determined, preferably by Phosphoimager analysis. Alternatively, the autoradiograph can be scanned by an imaging densitometer to determine the relative intensities of the first 20 fragments. These intensities are then analyzed statistically as described in Example 6 in order to determine their variability. For example, the values can be plotted using the Macintosh program Kaleidograph Version 3.0 (Synergy Software). The resulting plots are fit to an exponential decay curve using the Kaleidograph library routine for this function. $R^2$, the correlation index for the data, is calculated by the Kaleidograph library routine. This is a measure of the variability in band intensities. The values obtained for $R^2$ using a new DNA polymerase are compared to those obtained using known DNA polymerases, for example Δ28 T7 DNA polymerase (Sequenase Version 2.0, United States Biochemical Corporation) in the presence of magnesium or manganese (see Tabor and Richardson 265 *J. Biol. Chem.* 8322, 1990), *E. coli* DNA polymerase I (either Klenow fragment or Klenow fragment with the mutation F762Y) or Taq DNA polymerase (either wild-type or the mutant F667Y). The $R^2$ values obtained with these known DNA polymerases are used as standards by which to compare a new DNA polymerase for its uniformity.

Example 14

Determination of Uniformity of Incorporation of [α-$^{32}$P]ddNMPs Using a Single-Stranded M13 DNA - Unlabeled Primer Complex and Gel Electrophoresis In this example the uniformity of dideoxynucleotide incorporation is measured using an unlabeled primer annealed to a single-stranded M13 DNA template and carrying out DNA synthesis in the presence of [α-$^{32}$P]ddATP. The test described in Example 13 is preferred over this one for measuring uniformity of dideoxynucleotide-terminated fragments, since it is more amenable to use of high concentrations of ddNTPs, which are required for use in enzymes that discriminate strongly against ddNTPs, such as *E. coli* DNA polymerase I, Taq DNA polymerase and T7 DNA polymerase Y526F. The test in this example is most suited for use with enzymes that incorporate dideoxynucleotides efficiently, such as T7 DNA polymerase, *E. coli* DNA polymerase I F762Y and Taq DNA polymerase F667Y.

The primer, template and general reaction conditions in this example are similar to those described in Example 8, with the following exceptions. The template is M13 mGP1-2 single-stranded DNA described in Example 3, and the primer is the 40 mer also described in Example 3. Reaction conditions used are those that are optimum for the DNA polymerase being tested with regard to buffer, pH, salts, and temperature of the reaction. It is preferred that magnesium is the only metal ion present in the reaction mixture (i.e. the reactions are carried out in the absence of added manganese ions). The reactions are carried out with 50 µM dGTP, dCTP and dTTP, and varying concentrations of dATP and [α-$^{32}$P] ddATP. The concentrations of dATP and [α-$^{32}$P]ddATP are chosen to maximize the amount of radioactivity in fragments approximately 100 nucleotides in length. All other aspects with respect to gel electrophoresis and analysis of the radioactive fragments are as described in Example 13.

Example 15

Determination of Uniformity of Incorporation of Dideoxynucleotides Using a Single-Stranded M13 DNA - Fluorescently-Labeled Primer Complex and Gel Electrophoresis In this example, reactions are carried out as described in Example 11. The template is M13 mGP1-2 single-stranded DNA described in Example 3, and the primer is the 40 mer also described in Example 3. Reaction conditions used are those that are optimum for the DNA polymerase being tested with regard to buffer, pH, salts, and temperature of the reaction. It is preferred that magnesium is the only metal ion present in the reaction mixture (i.e. the reactions are carried out in the absence of added manganese ions). A concentration of DNA polymerase is chosen whereby most of the primers are extended in a 10 min reaction and are terminated by the incorporation of a dideoxynucleotide. The ratios of dNTPs to ddNTPs are adjusted for the specific DNA polymerase being tested so that the average fragment size is approximately 100–200 nucleotides. ddCTP is the preferred ddNTP to use since fragments terminated with this dideoxynucleotide tend to have the most variability in intensities (see for example Tabor and Richardson 86 *Proc. Natl. Acad. Sci.* 4076, 1989). The intensities of up to the first 50 dideoxy-terminated fragments from the primer (approximately 200 nucleotides) are determined, and they are analyzed statistically as described in Example 13. The correlation index $R^2$ is determined for the DNA polymerase being tested, and compared with that obtained with known DNA polymerases such as those described in Example 13. Alternatively, the heights of the first 50 bands are determined and the ratio of heights of adjacent bands are calculated and used as a measure of variability; the maximum and mean of these ratios obtained from reactions carried out with the DNA polymerase being tested are compared with the values obtained for reactions carried out using known DNA polymerases such as those described in Example 13.

Example 16

Determination of Uniformity of Incorporation of Fluorescent Dideoxynucleotides by Gel Electrophoresis In this example, reactions are carried out as described in Example 12. In order to determine the uniformity of incorporation of the DyeDeoxy Terminators for a specific DNA polymerase, the concentration of dNTPs and the specific DyeDeoxy Terminator are chosen to obtain fluorescently labeled fragments that average 100–200 nucleotides in length. The intensity of fluorescence is determined for fragments 10 to 40 from the primer (the first 10 fragments near the fluorescently labeled primer are ignored). The fragments are analyzed statistically as described in Example 13, and the average variability is defined by $R^2$, the correlation index for the data fitted to an exponential decay curve. The values obtained for $R^2$ are compared with those obtained using known DNA polymerases as described in Example 13. To determine if a specific mutation in a DNA polymerase is resulting in that DNA polymerase producing bands that have less variability, the $R^2$ value obtained for the mutant DNA polymerase is compared to that obtained for the unmodified DNA polymerase.

Example 17

DNA Sequence Analysis Using a DNA Polymerase That Efficiently Incorporates Dideoxynucleotides DNA sequence analysis with a DNA polymerase of this invention is carried out using standard procedures, with the ratio of dNTPs to ddNTPs adjusted to obtain dideoxy-terminated fragments of an average length appropriate for separation by electrophoresis. For the mutant in the large fragment of *E. coli* DNA polymerase I, "Klenow fragment F762Y", reactions are carried out essentially as with modified T7 DNA polymerase and described in Tabor and Richardson U.S. Pat. No. 4,795,699, Tabor and Richardson 84, *Proc. Natl. Acad. Sci. USA* 4767, 1987, and SEQUENASE manual, "Step-By-Step Protocols For DNA Sequencing With SEQUENASE" 3rd Edition, United States Biochemical Corporation. Since Klenow fragment F762Y incorporates dideoxynucleotides approximately 5 times more efficiently than modified T7 DNA polymerase, the concentration of ddNTPs in the extension-termination mixtures should be reduced by a factor of five compared with the standard mixtures recommended for modified T7 DNA polymerase (Sequenase manual, supra).

DNA sequence analysis with a thermostable DNA polymerase such as Taq DNA polymerase F667Y is as described by Innis et al. 85, *Proc. Natl. Acad. Sci. USA* 9436, 1988, with the following modification. Whereas Innis et al. recommend, dNTP/ddNTP ratios of 1:6 dGTP:ddGTP, 1:32 dATP:ddATP, 1:48 dTTP:ddTTP and 1:16 dCTP:ddCTP, these ratios must be adjusted to take into account the 3,000–8,000 fold more efficient use of the 4 ddNTPs by the Taq DNA polymerase F667Y compared with the wild-type Taq DNA polymerase. Thus the extension-termination reactions with Taq DNA polymerase F667Y should contain 100 µM 4 dNTPs and 0.1–5 µM each of the four ddNTPs; the exact amount of each ddNTP should be adjusted based on the desired average fragment size for optimum determination of DNA sequence. All other aspects of the DNA sequencing reactions and denaturing gel electrophoresis are as described in Innis et al. (supra).

Example 18

Cycle DNA Sequence Analysis Using a Thermostable DNA Polymerase That Efficiently Incorporates Dideoxynucleotides Cycle DNA sequencing with a thermostable DNA polymerase such as Taq DNA polymerase F667Y is carried out as described in Carothers et al. 7 *Bio Techniques* 494, 1989 except that: (1) The four deoxy/dideoxy NTP mixes contain 250 µM of all four dNTPs and 0.1–10 µM of either ddGTP, ddATP, ddTTP or ddCTP, the exact amount of each ddNTP adjusted empirically based on the desired average fragment size for optimum determination of DNA sequence. (2) Taq DNA polymerase F667Y is used in place of Taq DNA polymerase, using the same number of units of DNA polymerase as recommended by Carothers et al. (supra). (3) The reaction mixtures contain 10 ng of inorganic pyrophosphatase to inhibit pyrophosphorolysis that could otherwise increase the apparent discrimination by the DNA polymerase at specific sequences, reducing the uniformity of band intensities (Tabor and Richardson 265 *j. Biol. Chem.* 8322, 1990). Preferably this pyrophosphatase is purified from a thermophilic organism, for example from *Thermus thermophilus* (Hohne et al. 47 *Biomed. Biochim. Acta* 941, 1988).

Example 19

Automated Cycle DNA Sequencing Using Modified Taq DNA Polymerase and Fluorescent Primers Cycle DNA sequencing with a thermostable DNA polymerase such as Taq DNA polymerase F667Y and the Applied Biosystems Dye Primers is a modification of the procedure described in the Applied Biosystems manual (Part Number 901482, Rev. B). The procedure is identical to that described in the manual with the following modifications: (1) The dNTP/ddNTP mixes must be modified to take into account the more efficient use of ddNTPs by Taq DNA polymerase F667Y compared to Taq DNA polymerase. The new mixes that should be used in place of the ones listed in the Applied Biosystems manual are as follows:

dG/ddG mix=100 µM $c^7$dGTP, dATP, dTTP and dCTP, and 0.05 µM ddGTP dA/ddT mix=100 µM $c^7$dGTP, dATP, dTTP and dCTP, and 0.3 µM ddATP dT/ddT mix=100 µM $c^7$dGTP, dATP, dTTP and dCTP, and 0.25 µM ddTTP dC/ddC mix=100 µM $c^7$dGTP, dATP, dTTP and dCTP, and 0.15 µM ddCTP The concentrations of ddNTPs should be varied to optimize the intensity of fluorescence in fragments of specific size ranges, depending on the application. For example, increasing the concentration of ddNTPs will increase the fluorescence of fragments of shorter length. (2) Taq DNA polymerase F667Y is used in place of Taq DNA polymerase. The same number of units of enzyme are used in both cases, when assayed under standard DNA polymerase assay conditions. Alternatively, the same number of DNA polymerase molecules can be used. (3) The reaction mixtures contain 10 ng of inorganic pyrophosphatase to inhibit pyrophosphorolysis that could otherwise increase the apparent discrimination by the DNA polymerase at specific sequences, reducing the uniformity of band intensities (Tabor and Richardson 265 *J. Biol. Chem.* 8322, 1990). Preferably this pyrophosphatase is purified from a thermophilic organism, for example from *Thermus thermophilus* (Hohne et al. 47 *Biomed. Biochim. Acta* 941, 1988). All other aspects of the procedures are identical to that described in the Applied Biosystems manual (supra).

Example 20

Automated Cycle DNA Sequencing Using Modified Taq DNA Polymerase and Fluorescent Dye Terminators Cycle DNA sequencing with a thermostable DNA polymerase such as Taq DNA polymerase F667Y and the Applied Biosystems DyeDeoxy Terminators is a modification of the procedure in the Applied Biosystems manual (Part Number 901497, Rev. E). The procedure is identical to that described in the manual with the following modifications: (1) The manual calls for the use of 1 µl of each of the 4 DyeDeoxy Terminators undiluted in each sequencing reaction (20 µl reaction). In this Example the Terminators should be diluted prior to addition to the sequencing reaction mixture, since they are incorporated more than several hundred fold more efficiently with Taq DNA polymerase F667Y than with Taq DNA polymerase. 1 µl of each of the following dilutions are added to each sequencing reaction in place of 1 µl of the undiluted Terminator solutions:

DyeDeoxy G Terminator, 1 to 500 in $H_2O$
DyeDeoxy A Terminator, 1 to 1,500 in $H_2O$
DyeDeoxy T Terminator, 1 to 1,500 in $H_2O$
DyeDeoxy C Terminator, 1 to 1,000 in $H_2O$ These dilutions are approximations only; the precise dilution of each DyeDeoxy Terminator should be determined empirically depending on the number of bases of DNA sequence to be determined from the primer. (2) Taq DNA polymerase F667Y is used in place of Taq DNA polymerase. The same number of units of enzyme are used in both cases, when assayed under standard DNA polymerase assay conditions. Alternatively, the same number of DNA polymerase molecules can be used. (3) The reaction mixtures contain 10 ng of inorganic pyrophosphatase to inhibit pyrophosphorolysis that could otherwise increase the apparent discrimination by the DNA polymerase at specific sequences, reducing the uniformity of band intensities (Tabor and Richardson 265 *J. Biol. Chem.* 8322, 1990). Preferably this pyrophosphatase is purified from a thermophilic organism, for example from *Thermus thermophilus* (Hohne et al. 47 *Biomed. Biochim. Acta* 941, 1988).

Since this procedure uses over 500 times less DyeDeoxy Terminators that previous procedures, there is much less of a problem with unincorporated DyeDeoxy Terminators after the reactions is complete. Thus it is not necessary to remove the unincorporated DyeDeoxy Terminators by passing the sample over a spin column, as recommended in the Applied Biosystems manual (supra). Rather, the sample can be precipitated with ethanol, taken up in 5 µl deionized formamide and 1 µl 50 mM EDTA, pH 8.0, heated at 90° C. for 2 min, and loaded onto the Applied Biosystems 373A DNA Sequencing System according to the instructions in the 373A User's Manual. It is possible that with a DNA polymerase that incorporates the DyeDeoxy Terminators efficiently (such as Taq DNA polymerase F667Y) that concentration of the DNA sequencing reaction by precipitation with ethanol is not necessary; the DNA cycle sequencing reactions, carried out using preferably a high concentration of primer and dNTPs (see below), can be terminated by the addition of an equal volume of deionized formamide, heated at 90° C. for 2 min, and loaded immediately onto the Applied Biosystems 373A DNA Sequencing System. This represents a major savings in time to the researcher preparing the samples for DNA sequence determination.

The procedure described above uses a relatively low concentration of dNTPs at the outset (7.5 µM dATP, dTTP and dCTP and 37.5 µM dITP). The concentration of dNTPs decrease during the cycle DNA sequencing reaction as the dNTPs are used. This concentration of dNTPs (less than 7.5 µM) is less than optimal for maximum DNA polymerase activity for most DNA polymerases. This low concentration was necessary with previous protocols because the DNA polymerase that was used discriminated strongly against ddNTPs, requiring a high ratio of ddNTPs to dNTPs. The use of a DNA polymerase of this invention that discriminates much less against the DyeDeoxy Terminators now allows the use of higher concentrations of dNTPs. For example, in the protocol described above a 10-fold higher concentration of dNTPs and DyeDeoxy Terminators could be used; i.e. 75 μM dATP, dTTP and dCTP, 375 μM dITP, and the following dilutions of each of the four DyeDeoxy Terminators: DyeDeoxy G Terminator, 1 to 50 in H$_2$O; DyeDeoxy A Terminator, 1 to 150 in H$_2$O; DyeDeoxy T Terminator, 1 to 150 in H$_2$O; DyeDeoxy C Terminator, 1 to 100 in H$_2$O. Thus in this example the DyeDeoxy Terminator concentrations are still at least lower than that in previous protocols by a factor of at least 50.

Example 21

Exonuclease Assay Using a [$^{32}$P]ddAMP Terminated DNA Substrate

The 3'[$^{32}$P]ddAMP-terminated DNA substrate is prepared by digesting native calf thymus DNA with HindIII in a reaction mixture (50 μl) that contains 10 μg double-stranded calf thymus DNA, 40 mM Tris.HCl, pH 7.5, 10 mM MgCl$_2$, 5 mM dithiothreitol, 50 mM NaCl, 50 μg/ml bovine serum albumin, and 10 units HindIII. After incubation at 37° C. for 60 min, 5 μl of [α-$^{32}$P]ddATP (Amersham PB10235, >5000 Ci/mmol) and 5 units Sequenase Version 2.0 (United States Biochemical Corporation, catalog number 70775) are added, and the mixture is incubated at 20° C. for 15 min. The reaction mixture is extracted once with an equal volume phenol:chloroform:isoamyl alcohol (24:24:1), and fractionated on a 1 ml column of Sephadex G100 (Pharmacia) in 20 mM Tris.HCl, pH 7.5, 2 mM EDTA, 100 mM NaCl. The 3' $^{32}$P-labeled DNA, that elutes in the void volume, has a specific activity of approximately 500 cpm/ng of total DNA.

Reaction mixtures for exonuclease assays (90 μl) contain 40 mM Tris.HCl, pH 7.5, 10 mM MgCl$_2$, 10 mM dithiothreitol, 50 mM KCl and 1 nmol 3' $^{32}$P-labeled DNA. The reaction mixtures also contain 10 ng of yeast inorganic pyrophosphatase to remove trace amounts of pyrophosphate and thus prevent pyrophosphorolysis (Tabor and Richardson 265 *j. Biol. Chem.* 8322, 1990). This mixture is preincubated at 20 ° C. for 1 min, then 10 μl of the appropriate enzyme dilution is added. After incubation at 37° C. for the indicated times, the reactions are stopped by the addition of 30 μl of bovine serum albumin (10 mg/ml) and 30 μl of trichloracetic acid (100% w/v). The precipitated DNA is incubated at 0° C. for 15 min, and then pelleted by centrifugation at 12,000 g for 30 min. The acid-soluble radioactivity is measured in 100 μl of the supernatant. One unit of 3'[$^{32}$P]ddAMP-DNA exonuclease activity catalyzes the acid solubilization of one pmol of [$^{32}$P]ddAMP in 15 min.

Other embodiments are within the following claims.

TABLE 1

Summary of T7 DNA Polymerase Dideoxy-Resistant Mutants

| Mutant | No. isolates | Modification | |
|---|---|---|---|
| DR1 | 1 | Ala 425 → Thr | Hydrophobic → Polar |
| DR2 | 1 | Phe 434 → Ser | Hydrophobic → Polar |
|  |  | Gly 442 → Ser | Hydrophobic → Polar |
| DR3 | 1 | Val 443 → Ile | Hydrophobic → Hydrophobic |
| DR4 | 2 | Arg 444 → His | Strong basic → Weak basic |
| DR5 | 1 | Arg 444 → Cys | Strong basic → Neutral, polar |
| DR6 | 8 | Ser 477 → Phe | Polar → Hydrophobic |
| DR7 | 4 | Asp 504 → Asn | Basic → Neutral |
| DR8 | 2 | Ala 513 → Thr | Hydrophobic → Polar |
| DR9 | 2 | Thr 517 → Ile | Polar → Hydrophobic |
| DR10 | 1 | Ala 532 → Ser | Hydrophobic → Polar |
| DR11 | 1 | Arg 566 → Cys | Strong basic → Neutral, polar |
| DR12 | 1 | Ala 619 → Thr | Hydrophobic → Polar |
| DR13 | 3 | Ala 700 → Thr | Hydrophobic → Polar |

Summary:
7 Hydrophobic → Polar
3 Strong basic → Neutral, polar or weak basic
2 Polar → Hydrophobic
1 Hydrophobic → Hydrophobic

TABLE 2

Effect of domain exchanges between *E. coli* DNA polymerase I, T7 DNA polymerase, and Taq DNA polymerase within helix O on discrimination against ddNTPs. The sequence of the three polymerases are shown at the top, with the number of the first residue indicated. Below the consensus sequence for these three polymerases the mutants characterized in T7 DNA polymerase (T7), *E. coli* DNA polymerase I (Pol) and Taq DNA polymerase (Taq) are shown, with the mutated residues underlined. Each mutant was tested for its relative rate of incorporation of ddNMP to dNMP by SDS activity gel analysis as described in example 2., and indicated on the right. Mutants T7 C-T8, Pol I C-K6, and Taq C-Q5 were purified along with the wild-type proteins for further analysis.

| ENZYME | SEQUENCE | ddNTP DISCRIMINATION | SEQUENCE ID NO. |
|---|---|---|---|
| Pol I 754 | RRSAKAINFGLIYG | HIGH | SEQUENCE ID NO 1 |
| Taq 658 | RRAAKTINFGVLYG | HIGH | SEQUENCE ID NO 2 |
| T7 517 | RDNAKTFIYGFLYG | LOW | SEQUENCE ID NO 3 |
| Consensus | R AK G YG |  |  |
| T7 WT | RDNAKTFIYGFLYG | LOW | SEQUENCE ID NO 4 |
| T7 C-T2 | RRSAKAINFGLIYG | HIGH | SEQUENCE ID NO 5 |
| T7 C-T3 | RRSAKTFIYGFLYG | LOW | SEQUENCE ID NO 6 |
| T7 C-T4 | RDNAKAINFGFLYG | HIGH | SEQUENCE ID NO 7 |
| T7 C-T5 | RDNAKAIYGFLYG | LOW | SEQUENCE ID NO 8 |
| T7 C-T6 | RDNAKTFNFGFLYG | HIGH | SEQUENCE ID NO 9 |
| T7 C-T7 | RDNAKTFNYGFLYG | LOW | SEQUENCE ID NO 10 |
| T7 C-T8 | RDNAKTFIFGFLYG | HIGH | SEQUENCE ID NO 11 |
| POL I WT | RRSAKAINFGLIYG | HIGH | SEQUENCE ID NO 12 |
| POL I C-K1 | RDNAKTFIYGFLYG | LOW | SEQUENCE ID NO 13 |

TABLE 2-continued

Effect of domain exchanges between *E. coli* DNA polymerase I, T7 DNA polymerase, and Taq DNA polymerase within helix O on discrimination against ddNTPs. The sequence of the three polymerases are shown at the top, with the number of the first residue indicated. Below the consensus sequence for these three polymerases the mutants characterized in T7 DNA polymerase (T7), *E. coli* DNA polymerase I (Pol) and Taq DNA polymerase (Taq) are shown, with the mutated residues underlined. Each mutant was tested for its relative rate of incorporation of ddNMP to dNMP by SDS activity gel analysis as described in example 2., and indicated on the right. Mutants T7 C-T8, Pol I C-K6, and Taq C-Q5 were purified along with the wild-type proteins for further analysis.

| ENZYME | SEQUENCE | ddNTP DISCRIMINATION | SEQUENCE ID NO. |
|---|---|---|---|
| POL I C-K2 | RRSAKTFIYGLIYG | LOW | SEQUENCE ID NO 14 |
| POL I C-K3 | RRSAKTFNFGLIYG | HIGH | SEQUENCE ID NO 15 |
| POL I C-K4 | RRSAKAIIYGLIYG | LOW | SEQUENCE ID NO 16 |
| POL I C-K5 | RRSAKAIIFGLIYG | HIGH | SEQUENCE ID NO 17 |
| POL I C-K6 | RRSAKAINYGLIYG | LOW | SEQUENCE ID NO 18 |
| Taq WT | RRAAKTINFGVLYG | HIGH | SEQUENCE ID NO 19 |
| Taq C-Q1 | RDNAKTINFGVLYG | HIGH | SEQUENCE ID NO 20 |
| Taq C-Q2 | RRAAKTFIYGFLYG | LOW | SEQUENCE ID NO 21 |
| Taq C-Q3 | RRAAKTIIYGVLYG | LOW | SEQUENCE ID NO 22 |
| Taq C-Q4 | RRAAKTIIFGVLYG | HIGH | SEQUENCE ID NO 23 |
| Taq C-Q5 | RRAAKTINYGVLYG | LOW | SEQUENCE ID NO 24 |

Specificity residue

---

We claim:

1. Modified gene encoding a modified Pol I-type DNA polymerase wherein said modified gene is modified to encode a tyrosine residue at an amino acid position corresponding to T7 DNA polymerase residue 526 or at an amino acid position corresponding to *E. coli* DNA polymerase residue 762 in its dNMP binding site to increase ability of said modified DNA polymerase to incorporate a dideoxynucleotide relative to a corresponding deoxynucleotide compared to the ability of a corresponding naturally-occurring unmodified DNA polymerase by at least 20-fold.

2. The modified gene of claim 1 wherein said modified DNA polymerase has sufficient DNA polymerase activity for use in DNA sequencing when combined with any factor necessary for said DNA polymerase activity.

3. The modified gene of claim 1 wherein said modified DNA polymerase has less than 500 units exonuclease activity per mg polymerase.

4. A modified DNA polymerase encoded by the modified gene of any of claims 1 to 3.

5. The modified gene of claim 1 wherein said modified DNA polymerase is a thermostable enzyme.

6. The modified gene of claim 5 wherein said thermostable enzyme is selected from the group consisting of DNA polymerase encoded by *Thermus aquaticus*, *Thermus thermophilis*, *Thermus flavus*, and *Bacillus sterothermophilus*.

7. The modified gene of claim 1 wherein said ability of said polymerase to incorporate a dideoxynucleotide relative to the corresponding deoxynucleotide is increased at least 25-fold compared to the corresponding naturally-occurring unmodified DNA polymerase.

8. The modified gene of claim 1 wherein said ability is increased at least 50-fold.

9. The modified gene of claim 1 wherein said ability is increased at least 100-fold.

10. The modified gene of claim 1 wherein said ability is increased at least 500-fold.

11. Method for production of a modified Pol I-type DNA polymerase having an increased ability to incorporate a dideoxynucleotide relative to a corresponding deoxynucleotide compared to ability of a corresponding naturally-occurring unmodified DNA polymerase comprising steps of: providing a nucleic acid molecule encoding a DNA polymerase and mutagenizing said nucleic acid molecule to incorporate one or more base changes in nucleotide base sequence at a region that encodes its dNMP binding site to encode a tyrosine residue at an amino acid position corresponding to T7 DNA polymerase residue 526 or at an amino acid position corresponding to *E. coli* DNA polymerase residue 762 in the dNMP binding site to alter ability of said polymerase encoded by said nucleic acid to incorporate a dideoxynucleotide by at least 20-fold.

12. Method for determining a nucleotide base sequence of a DNA molecule comprising the steps of:

incubating a DNA molecule annealed with a primer molecule able to hybridize to said DNA molecule in a vessel containing at least one deoxynucleoside triphosphate, a Pol I-type DNA polymerase modified by having a tyrosine residue at an amino acid position corresponding to T7 DNA polymerase residue 526 or at an amino acid position corresponding to *E. coli* DNA polymerase residue 762 in its dNMP binding site compared to a naturally-occurring unmodified DNA polymerase to have at least a 20-fold increased ability to incorporate a dideoxynucleotide relative to a corresponding deoxynucleotide compared to said naturally-occurring unmodified polymerase, said polymerase having sufficient DNA polymerase activity and less than 1000 units exonuclease activity per mg DNA polymerases, and at least one DNA synthesis terminating agent which terminates DNA synthesis at a specific nucleotide base, in an incubating reaction; and separating the DNA products of the incubating reaction according to size whereby at least a part of the nucleotide base sequence of said DNA molecule can be determined.

13. The method of claim 12 wherein said DNA polymerase is a thermostable DNA polymerase and sequencing is performed at a temperature above 50° C.

14. The method of claim 13 wherein said DNA polymerase is a thermostable DNA polymerase and said sequencing is performed at a temperature above 60° C.

15. The method of claim 14 wherein said thermostable enzyme is selected from the group consisting of DNA polymerase encoded by *Thermus aquaticus, Thermus thermophilis, Thermus flavus* and *Bacillus sterothermophilus*.

16. The method of claim 12 wherein said DNA polymerase discriminates between deoxynucleotides and dideoxynucleotides by less than a factor of 100.

17. The method of claim 12 wherein said DNA polymerase discriminates between deoxynucleotides and dideoxynucleotides by less than a factor of 50.

18. The method of claim 12 wherein said DNA polymerase has less than 500 units of exonuclease activity per mg of polymerase.

19. A kit for DNA sequencing comprising a modified Pol I-type DNA polymerase modified to include a tyrosine residue at an amino acid position corresponding to T7 DNA polymerase residue 526 or at an amino acid position corresponding to *E. coli* DNA polymerase residue 762 in its dNMP binding site of the DNA polymerase to increase the ability of said DNA polymerase to incorporate a dideoxynucleotide compared to ability of a corresponding naturally-occurring unmodified DNA polymerase by at least 20-fold relative to a corresponding deoxynucleotide; and a reagent necessary for said sequencing selected from the group consisting of dITP, a chain terminating agent, deaza-GTP and a manganese-containing compound.

20. A method for sequencing a strand of DNA comprising the steps of:

providing said strand hybridized with a primer able to hybridize to said strand, to form an hybridized mixture, incubating said hybridized mixture with one or more deoxyribonucleoside triphosphates, a modified Pol I-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase to incorporate a dideoxynucleotide at least 20-fold relative to a corresponding deoxynucleotide compared to ability of a corresponding naturally-occurring unmodified DNA polymerase, and a first chain terminating agent, wherein said DNA polymerase causes said primer to be elongated to form a first series of first DNA products differing in the length of the elongated primer, each said first DNA product having a said chain terminating agent at its elongated end, the number of molecules of each said first DNA products being approximately the same for substantially all DNA products differing in length by no more than 20 bases, and providing a second chain terminating agent in said hybridized mixture at a concentration different from said first chain terminating agent, wherein said DNA polymerase causes production of a second series of second DNA products differing in the length of the elongated primer, each said second DNA product having said second chain terminating agent at its elongated end, the number of molecules of each said second DNA products being approximately the same for substantially all second DNA products differing in length from each other by from 1 to 20 bases, and being distinctly different from the number of molecules of all said first DNA products having a length differing by no more than 20 bases from that of said second DNA products.

21. Method for sequencing a nucleic acid comprising:

combining an oligonucleotide primer, a nucleic acid to be sequenced, between one and four deoxyribonucleoside triphosphates, a modified Pol I-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase to incorporate a dideoxynucleotide at least 20-fold relative to a corresponding deoxynucleotide compared to ability of a corresponding naturally-occurring unmodified DNA polymerase, and at least two chain terminating agents in different amounts, under conditions favoring extension of said oligonucleotide primer to form nucleic acid fragments complementary to the nucleic acid to be sequenced; separating the nucleic acid fragments by size; and determining nucleic acid sequence wherein said agents are differentiated from each other by intensity of a label in the primer extension products.

22. A method for in vitro mutagenesis of a cloned DNA fragment comprising providing said cloned fragment and a modified Pol I-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase to incorporate a dideoxynucleotide at least 20-fold relative to a corresponding deoxynucleotide compared to ability of a corresponding naturally-occurring unmodified DNA polymerase, contacting said cloned fragment with said polymerase under conditions for synthesizing a DNA strand from said fragment, wherein said conditions cause formation of said DNA strand by incorporation of a plurality of individual contiguous bases able to base-pair with said fragment and incorporation of a nucleotide base unable to base pair with said fragment.

23. A method for in vitro mutagenesis of a template DNA fragment comprising providing a primer and said template, said primer having contiguous bases able to base-pair with contiguous bases of said template except at least one base which is unable to base-pair with said template, and extending said primer with a modified Pol I-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase at least 20-fold relative to a corresponding deoxynucleotide to incorporate a dideoxynucleotide compared to ability of a corresponding naturally-occurring unmodified DNA polymerase.

24. A method for producing blunt-ended double-stranded DNA from a linear DNA molecule having a 5' end comprising a single-stranded region, wherein 3' end of said molecule is double stranded and has no 3' protruding termini, comprising incubating said DNA molecule with a modified Pol I-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase at least 20-fold to incorporate a dideoxynucleotide relative to a corresponding deoxynucleotide compared to ability of a corresponding naturally-occurring unmodified DNA polymerase, wherein said polymerase acts on said single-stranded region to produce a blunt-ended double stranded DNA molecule.

25. A method for labeling a 3' end of a DNA fragment comprising incubating said DNA fragment with a modified Pol I-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase at least 20-fold to incorporate a dideoxynucleotide relative to a corresponding deoxynucleotide compared to ability of a corresponding naturally-occurring unmodified DNA polymerase, and a labelled deoxynucleotide species under conditions in which said 3' end of said DNA fragment is extended by said polymerase and thereby labelled by addition of said labelled deoxynucleotide to said DNA fragment.

26. A method of amplification of a DNA sequence comprising annealing a first and second primer to opposite strands of a double-stranded DNA sequence to form an annealed mixture and incubating the annealed mixture with a modified Pol I-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability at least 20-fold of said polymerase to incorporate a dideoxynucleotide relative to a corresponding deoxynucleotide compared to ability of a corresponding naturally-occurring unmodified DNA polymerase, wherein said first and second primers anneal to opposite strands of said DNA sequence with their 3' ends directed towards each other after annealing, and with the DNA sequence to be amplified located between the first and second annealed primers.

27. A *Thermus aquaticus* DNA polymerase having a tyrosine at residue 667.

28. An *E. coli* DNA polymerase I having a tyrosine at residue 762.

29. Purified Pol I type DNA polymerase having a tyrosine residue at an amino acid position corresponding to *E. coli* DNA polymerase residue 762 in its dNMP binding site provided that said polymerase is not a T7-type DNA polymerase or a mitochondrial DNA polymerase.

30. The Pol I type DNA polymerase of claim 29 wherein its dNMP binding site comprises the amino acid sequence K $N_1$ $N_2$ $N_3$ $N_4$ $N_5$ $N_6$ $N_7$ Y G/Q, wherein each N is independently any amino acid wherein the K corresponds to amino acid residue 758 of *E. coli* DNA Polymerase I and said position $N_4$ is tyrosine.

31. A modified alpha-type DNA polymerase comprising the sequence K $N_1$ $N_2$ $N_3$ $N_4$ $N_5$ $N_6$ Y G, at its dNMP binding site wherein each N is independently any amino acid, and wherein one said N is mutated to have a tyrosine residue at an amino acid position corresponding to T7 DNA polymerase residue 526 or at an amino acid position corresponding to E. coli DNA polymerase residue 762 in its dNMP binding site to provide a polymerase which does not discriminate against ddNMP incorporation more than 50 fold relative to the corresponding dNMP incorporation.

32. Recombinant nucleic acid encoding any of the DNA polymerases of claims 27 to 31.

33. Recombinant DNA polymerase which in the presence of magnesium as the only added divalent cation has an average processivity of less than 100 and discriminates less than 100 times against incorporation of a ddNMP relative to a corresponding deoxynucleotide, wherein said DNA polymerase is not reverse transcriptase and wherein said DNA polymerase includes a tyrosine residue at an amino acid position corresponding to T7 DNA polymerase residue 526 or at an amino acid position corresponding to *E. coli* DNA polymerase residue 762 in its dNMP binding site.

34. Recombinant DNA polymerase which in the presence of magnesium as the only divalent cation has an average processivity of less than 50 and discriminates less than 50 times against incorporation of a ddNMP relative to a corresponding deoxynucleotide and wherein said DNA polymerase includes a tyrosine residue at an amino acid position corresponding to T7 DNA polymerase residue 526 or at an amino acid position corresponding to *E. coli* DNA polymerase residue 762 in its dNMP binding site.

35. Recombinant DNA polymerase which in the presence of magnesium as the only divalent cation has an average processivity of less than 50 and discriminates less than 5 times against incorporation of a ddNMP relative to a corresponding deoxynucleotide and wherein said DNA polymerase includes a tyrosine residue at an amino acid position corresponding to T7 DNA polymerase residue 526 or at an amino acid position corresponding to *E. coli* DNA polymerase residue 762 in its dNMP binding site.

36. Recombinant Thermophilic DNA polymerase that discriminates against a ddNMP relative to a corresponding deoxynucleotide by less than a factor of 100 and wherein said DNA polymerase includes a tyrosine residue at an amino acid position corresponding to T7 DNA polymerase residue 526 or at an amino acid position corresponding to *E. coli* DNA polymerase residue 762 in its dNMP binding site.

37. Recombinant Thermophilic DNA polymerase that discriminates in the presence of magnesium as the only divalent cation against a ddNMP relative to a corresponding deoxynucleotide by less than a factor of 100 and wherein said DNA polymerase includes a tyrosine residue at an amino acid position corresponding to T7 DNA polymerase residue 526 or at an amino acid position corresponding to *E. coli* DNA polymerase residue 762 in its dNMP binding site.

38. The DNA polymerase of claim 37 wherein said polymerase has an average processivity less than 100.

39. The polymerase of claim 38 wherein said polymerase cycles from one primer-template to another more than once per five seconds.

40. Recombinant Nucleic acid encoding the polymerase of any of claims 33–39.

41. Method for cycle sequencing using a DNA polymerase of any one of claims 27–31 or 33–39 wherein said method comprises mixing said DNA polymerase with a DNA molecule to be sequenced, a primer, dNTPs, and at least one chain terminating agent to form a mixture and cycling temperature of the mixture to allow alternate extension of the primer and denaturation of the primer and DNA molecule.

42. A purified cellular DNA polymerase having a tyrosine residue in place of the naturally occurring amino acid residue at an amino acid position corresponding to T7 DNA polymerase residue 526 or at an amino acid position corresponding to *E. coli* DNA polymerase residue 762 in its dNMP binding site which causes said polymerase not to discriminate against a ddNMP relative to a corresponding deoxynucleotide by more than 50 fold.

43. The DNA polymerase alpha of claim 31 wherein said polymerase that incorporates ddNMPs more efficiently relative to a corresponding deoxynucleotide than a corresponding naturally occurring non-modified polymerase.

44. Method for cycle sequencing, comprising step of providing an excess or equal amount of all four dNTPs compared to each of the four ddNTPs in a cycle sequencing reaction and performing said cycle sequencing reaction using a DNA polymerase having a tyrosine residue at an amino acid position corresponding to T7 DNA polymerase residue 526 or at an amino acid position corresponding to *E. coli* DNA polymerase residue 762 in its dNTP binding site that does not discriminate against incorporation of a ddNMP relative to a corresponding deoxynucleotide by more than 50-fold.

45. Method for cycle sequencing comprising step of providing less than 10 times of an amount of all four fluorescently labelled dideoxynucleotide than a corresponding deoxynucleotides in a cycle sequencing reaction and performing said cycle sequencing reaction using a DNA polymerase having a tyrosine residue at an amino acid position corresponding to T7 DNA polymerase residue 526 or at an amino acid position corresponding to *E. coli* DNA polymerase residue 762 in its dNMP binding site that does not discriminate against incorporation of a ddNMP relative to a corresponding deoxynucleotide by more than 50-fold.

46. A purified thermostable DNA polymerase having a deoxynucleotide binding site with the sequence K $N_1$ $N_2$ $N_3$ $N_4$ $N_5$ $N_6$ $N_7$ Y G/Q wherein each $N_1$–$N_3$ and $N_5$–$N_7$ is independently any amino acid and $N_4$ is a tyrosine residue at an amino acid position corresponding to T7 DNA polymerase residue 526 or at an amino acid position corresponding to *E. coli* DNA polymerase residue 762 in its dNMP binding site.

47. The purified thermostable DNA polymerase according to any of claim 46 wherein said DNA polymerase is not a naturally-occurring DNA polymerase.

48. The purified thermostable DNA polymerase according to claim 47 wherein said thermostable DNA polymerase is modified from a DNA polymerase selected from the group consisting of DNA polymerases from *Thermus thermophilis, Thermus flavus* and *Bacillus sterothermophilus*.

49. The purified DNA polymerase according to claim 47 wherein said polymerase is modified from a *Thermus aquaticus* DNA polymerase to have a tyrosine residue at a position corresponding to residue 667 of a corresponding naturally occurring unmodified polymerase.

50. The purified DNA polymerase according to claim 47 wherein in the presence of magnesium as the only divalent cation said polymerase has an average processivity of less than 50 and discriminates less than 50 times against incorporation of a ddNMP relative to a corresponding deoxynucleotide.

51. The purified thermostable DNA polymerase according to claim 47 wherein said polymerase has an average processivity less than 100.

52. The purified thermostable DNA polymerase according to claim 47 wherein said polymerase cycles from one primer-template to another more than once per five seconds.

53. The purified DNA polymerase according to claim 47 wherein said polymerase is modified to remove or reduce by at least 50% any exonuclease activity associated with a corresponding naturally occurring unmodified DNA polymerase.

54. The purified DNA polymerase according to claim 49 wherein said polymerase is further modified to remove or reduce 5'–3' exonuclease activity.

55. Purified nucleic acid encoding a DNA polymerase according to claim 47.

56. Purified nucleic acid encoding a DNA polymerase according to claim 49.

57. A kit for DNA sequencing comprising a DNA polymerase according to claim 47 and a reagent selected from the group consisting of dITP, a chain terminating agent and deazaGTP.

58. A kit for DNA sequencing comprising a DNA polymerase according to claim 49 and a reagent selected from the group consisting of dITP, a chain terminating agent and deazaGTP.

59. A kit for DNA sequencing comprising a DNA polymerase according to claim 47 and a pyrophosphatase.

60. A kit for DNA sequencing comprising a DNA polymerase according to claim 49 and a pyrophosphatase.

61. A solution comprising a DNA polymerase according to claim 47 and a pyrophosphatase.

62. A solution comprising a DNA polymerase according to claim 49 and a pyrophosphatase.

63. Method for production of a modified DNA polymerase comprising steps of: providing a nucleic acid molecule encoding a thermostable DNA polymerase comprising the sequence K $N_1$ $N_2$ $N_3$ $N_4$ $N_5$ $N_6$ $N_7$ Y G/Q at its dNMP binding site wherein each N is independently any amino acid and mutagenizing said nucleic acid molecule to incorporate one or more base changes in the nucleotide base sequence to encode a tyrosine residue at position $N_4$ corresponding to T7 DNA polymerase residue 526 or at to *E. coli* DNA polymerase residue 762 in its dNMP binding site.

64. A purified Pol I-type DNA polymerase having a tyrosine residue at an amino acid position corresponding to T7 DNA polymerase residue 526 or at an amino acid position corresponding to *E. coli* DNA polymerase residue 762 in its dNMP binding site, whereby ability to incorporate a dideoxynucleotide relative to a corresponding deoxynucleotide is increased 20-fold compared to ability of a corresponding naturally occurring unmodified DNA polymerase.

65. The DNA polymerase according to claim 64 wherein the DNA polymerase is a Pol I type DNA polymerase and the dNMP binding site comprises the amino acid residue sequence K $N_1$ $N_2$ $N_3$ $N_4$ $N_5$ $N_6$ $N_7$ Y G/Q wherein each N is independently any amino acid residue and $N_4$ is tyrosine.

66. The DNA polymerase according to claim 64 wherein the DNA polymerase is *E. coli* DNA polymerase I having a tyrosine at residue 762 or a Pol I type DNA polymerase having a tyrosine at an amino acid position corresponding to *E. coli* DNA polymerase I residue 762.

67. The DNA polymerase according to claim 64 wherein the ability of said DNA polymerase to incorporate a dideoxynucleotide relative to a corresponding deoxynucleotide is increased at least 20-fold compared to a corresponding naturally occurring unmodified DNA polymerase.

68. The DNA polymerase according to claim 64 wherein said polymerase is modified to remove or reduce any exonuclease activity associated with the corresponding naturally occurring unmodified DNA polymerase.

69. Purified nucleic acid encoding a DNA polymerase according to claim 64.

70. A method for production of a modified DNA polymerase having an increased ability to incorporate a dideoxynucleotide relative to a corresponding deoxynucleotide compared to ability of a corresponding naturally occurring unmodified DNA polymerase which comprises the steps of modifying a nucleic acid molecule encoding a DNA polymerase to incorporate one or more base changes in its nucleotide base sequence to encode a tyrosine residue at an amino acid position corresponding to T7 DNA polymerase residue 526 or at an amino acid position corresponding to *E. coli* DNA polymerase residue 762 in its dNMP binding site.

71. A method for determining the nucleotide base sequence of a DNA molecule comprising the steps of:

incubating a DNA molecule annealed with a primer molecule able to hybridize to said DNA molecule in a vessel containing at least one deoxynucleoside triphosphate, a DNA polymerase which in the presence of magnesium as the only added divalent cation discriminates less than 100 times against incorporation of a ddNMP relative to a corresponding deoxynucleotide provided that said DNA polymerase is not reverse transcriptase, or a T7-type DNA polymerase, wherein said polymerase has a tyrosine residue at an amino acid position corresponding to T7 DNA polymerase residue 525 or at an amino acid position corresponding to *E. coli* DNA polymerase residue 762 at its dNMP binding site, said polymerase having sufficient DNA polymerase activity to be useful for DNA sequencing and less than 1000 units exonuclease activity per mg DNA polymerase, and at least one DNA synthesis terminating agent which terminates DNA synthesis at a specific nucleotide base, in an incubating reaction; and separating the DNA products of the incubating reaction according to the size whereby at least a part of the nucleotide base sequence of said DNA molecule can be determinated.

72. A method for sequencing a strand of DNA comprising steps of: providing said strand hybridized with a primer able to hybridize to said strand, to form a hybridized mixture, incubating said hybridized mixture with one or more deoxyribonucleoside triphosphates, a DNA polymerase which is the presence of magnesium as the only added divalent cation discriminates less than 100 times against incorporation of a ddNMP relative to a corresponding deoxynucleotide provided that said DNA polymerase is not reverse transcriptase, or a T7-type DNA polymerase, wherein said polymerase has a tyrosine residue at an amino acid position corresponding to T7 DNA polymerase residue 525 or at an amino acid position corresponding to *E. coli* DNA polymerase residue 762 in its dNMP binding site and a first chain terminating agent, wherein said DNA polymerase causes said primer to be elongated to form a first series of first DNA products differing in length of the elongated primer, each of said first DNA products having said chain terminating agent at its elongated end, the number of molecules of each said first DNA products being approximately the same for substantially all DNA products differing in length by no more than 20 bases, and providing a second chain terminating agent in said hybridized mixture at a concentration different from said first chain terminating agent, wherein said DNA polymerase causes production of a second series of second DNA products differing in length of the elongated primer, each said second DNA product having said second chain terminating agent at its elongated end, the number of molecules of each said second DNA products being approximately the same for substantially all second DNA products differing in length from each other by 1 to 20 bases, and being distinctively different from the number of molecules of all said first DNA products having a length differing by no more than 20 bases from that of said second DNA products.

73. Method for sequencing a nucleic acid comprising:

combining an oligonucleotide primer, a nucleic acid to be sequenced, between one and four deoxyribonucleoside triphosphates, a DNA polymerase which in the presence of magnesium as the only added divalent cation discriminates less than 100 times against incorporation of a ddNMP relative to a corresponding deoxynucleotide provided that said DNA polymerase is not reverse transcriptase, or a T7-type DNA polymerase, and wherein said polymerase has a tyrosine residue at an amino acid position corresponding to T7 DNA polymerase residue 525 or at an amino acid position corresponding to *E. coli* DNA polymerase residue 762 in its dNMP binding site.

74. Method for determining a nucleotide base sequence of a DNA molecule comprising steps of incubating a DNA molecule annealed with a primer molecule able to hybridize to said DNA molecule in a vessel containing at least one deoxynucleotide triphosphate, a DNA polymerase having a tyrosine residue at an amino acid position corresponding to *E. coli* DNA polymerase I residue 762, said polymerase having sufficient DNA polymerase activity for use in DNA sequencing and having less than 1000 units low exonuclease activity, and at least one DNA synthesis terminating agent which terminates DNA synthesis at a specific nucleotide base in an incubating reaction; and separating DNA products of the incubating reaction according to size whereby at least a part of the nucleotide base sequence of said DNA molecule can be determined, provided that the DNA polymerase is not a T7-type DNA polymerase.

75. A kit for DNA sequencing comprising a DNA polymerase having a tyrosine residue at an amino acid position corresponding to *E. coli* DNA polymerase I residue 762, said polymerase having sufficient DNA polymerase activity for use in a DNA sequencing reaction and less than 1000 units per exonuclease activity per mg DNA polymerase, and a reagent necessary for said sequencing selected from the group consisting of dITP, a chain terminating agent and deaza-GTP provided that said polymerase is not a T7-type DNA polymerase.

76. A kit for DNA sequencing comprising pyrophosphatase and a DNA polymerase which in the presence of magnesium as the only added divalent cation discriminates less than 100 times against incorporation of a ddNMP relative to a corresponding deoxynucleotide provided that said DNA polymerase has a tyrosine at an amino acid position corresponding to T7 DNA polymerase residue 525 in its dNMP binding site or at an amino acid position corresponding to *E. coli* DNA polymerase residue 762 in its dNMP binding site, is not reverse transcriptase, or a T7-type DNA polymerase.

77. A kit for DNA sequencing comprising a DNA polymerase having a tyrosine residue at an amino acid position corresponding to *E. coli* DNA polymerase I residue 762 and a pyrophosphatase provided that the DNA polymerase is not a T7-type DNA polymerase.

78. A kit according to claim 77 wherein the DNA polymerase is modified to remove or reduce any exonuclease activity associated with a corresponding naturally occurring unmodified DNA polymerase.

79. A kit according to claim 77 in which the pyrophosphatase is thermostable.

80. The kit of any of claims 75 to 79, wherein said DNA polymerase is a Pol I-type DNA polymerase.

81. The kit of claims 75 to 79, wherein said DNA polymerase is a Pol II-type DNA polymerase.

82. The method of claim 74, wherein said DNA polymerase is a PolI-type DNA polymerase.

83. Modified gene encoding a modified Pol II-type DNA polymerase wherein said modified gene is modified to encode a tyrosine residue at an amino acid position corresponding to T7 DNA polymerase residue 526 or at an amino acid position corresponding to *E. coli* DNA polymerase residue 762 in its dNMP binding site to increase ability of said modified DNA polymerase to incorporate a dideoxynucleotide relative to a corresponding deoxynucleotide compared to ability of a corresponding naturally-occurring unmodified DNA polymerase.

84. The modified gene of claim 83 wherein said modified DNA polymerase has sufficient DNA polymerase activity for use in DNA sequencing when combined with any factor necessary for said DNA polymerase activity.

85. The modified gene of claim 83 wherein said modified DNA polymerase has less than 500 units exonuclease activity per mg polymerase.

86. A modified DNA polymerase encoded by the modified gene of any of claims 83 to 85.

87. The modified gene of claim 83 wherein said modified DNA polymerase is a thermostable enzyme.

88. The modified gene of claim 87 wherein said thermostable enzyme is selected from the group consisting of the DNA polymerase encoded by *Thermococcus litoralis*, and *Pyrococcus furiosis*.

89. Method for production of a modified Pol II-type DNA polymerase having an increased ability to incorporate a dideoxynucleotide relative to a corresponding deoxynucleotide compared to ability of a corresponding naturally-occurring unmodified DNA polymerase comprising steps of: providing a nucleic acid molecule encoding a DNA polymerase and mutagenizing said nucleic acid molecule to incorporate one or more base changes in nucleotide base sequence at a region that encodes its dNMP binding site to encode a tyrosine residue at an amino acid position corresponding to T7 DNA polymerase residue 526 or at an amino acid position corresponding to *E. coli* DNA polymerase residue 762 in its dNMP binding site to increase the ability of said polymerase encoded by said nucleic acid to incorporate a dideoxynucleotide.

90. Method for determining the nucleotide base sequence of a DNA molecule comprising steps of:
incubating a DNA molecule annealed with a primer molecule able to hybridize to said DNA molecule in a vessel containing at least one deoxynucleoside triphosphate, a Pol II-type DNA polymerase modified by having a tyrosine residue at an amino acid position corresponding to T7 DNA polymerase residue 526 or at an amino acid position corresponding to *E. coli* DNA polymerase residue 762 in its dNMP binding site compared to a naturally-occurring unmodified DNA polymerase to have increased ability to incorporate a dideoxynucleotide relative to a corresponding deoxynucleotide compared to said naturally-occurring unmodified polymerase, said polymerase having sufficient DNA polymerase activity for use in DNA sequencing and less than 1000 units exonuclease activity per mg DNA polymerases, and at least one DNA synthesis terminating agent which terminates DNA synthesis at a specific nucleotide base in an incubating reaction; and
separating DNA products of the incubating reaction according to size whereby at least a part of the nucleotide base sequence of said DNA molecule can be determined.

91. The method of claim 90 wherein said DNA polymerase is a thermostable DNA polymerase and said sequencing is performed at a temperature above 50° C.

92. The method of claim 91 wherein said DNA polymerase is a thermostable DNA polymerase and said sequencing is performed at a temperature above 60° C.

93. The method of claim 92 wherein said thermostable enzyme is selected from the group consisting of DNA polymerase encoded by *Thermococcus litoralis*, and *Pyrococcus furiosis*.

94. The method of claim 90 wherein said DNA polymerase discriminates between deoxynucleotides and dideoxynucleotides by less than a factor of 100.

95. The method of claim 90 wherein said DNA polymerase discriminates between deoxynucleotides and dideoxynucleotides by less than a factor of 50.

96. The method of claim 90 wherein said DNA polymerase has less than 500 units of exonuclease activity per mg of polymerase.

97. A kit for DNA sequencing comprising a modified Pol II-type DNA polymerase modified to include a tyrosine residue at an amino acid position corresponding to T7 DNA polymerase residue 526 or at an amino acid position corresponding to *E. coli* DNA polymerase residue 762 in its dNMP binding site to increase ability of said DNA polymerase to incorporate a dideoxynucleotide compared to ability of a corresponding naturally-occurring unmodified DNA polymerase relative to a corresponding deoxynucleotide; and a reagent necessary for said sequencing selected from the group consisting of dITP, a chain terminating agent, deaza-GTP and a manganese-containing compound.

98. A method for sequencing a strand of DNA comprising steps of: providing said strand hybridized with a primer able to hybridize to said strand, to form an hybridized mixture, incubating said hybridized mixture with one or more deoxyribonucleoside triphosphates, a modified Pol II-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase to incorporate a dideoxynucleotide relative to a corresponding deoxynucleotide compared to ability of the corresponding naturally-occurring unmodified DNA polymerase, and a first chain terminating agent, wherein said DNA polymerase causes said primer to be elongated to form a first series of first DNA products differing in length of elongated primer, each said first DNA product having said chain terminating agent at its elongated end, the number of molecules of each said first DNA products being approximately the same for substantially all first DNA products differing in length by no more than 20 bases, and providing a second chain terminating agent in said hybridized mixture at a concentration different from said first chain terminating agent, wherein said DNA polymerase causes production of a second series of second DNA products differing in the length of the elongated primer, each of said second DNA products having said second chain terminating agent at its elongated end, the number of molecules of each said second DNA products being approximately the same for substantially all second DNA products differing in length from each other by from 1 to 20 bases, and being distinctly different from the number of molecules of all said first DNA products having a length differing by no more than 20 bases from that of said second DNA products.

99. Method for sequencing a nucleic acid comprising:
combining an oligonucleotide primer, a nucleic acid to be sequenced, between one and four deoxyribonucleoside triphosphates, a modified Pol II-type DNA polymerase modified by having a tyrosine residue at an amino acid position corresponding to T7 DNA polymerase residue 526 or at an amino acid position corresponding to *E. coli* DNA polymerase residue 762 in its dNMP binding site to increase ability of said polymerase to incorporate a dideoxynucleotide relative to a corresponding deoxynucleotide compared to a ability of a corresponding naturally-occurring unmodified DNA polymerase, and at least two chain terminating agents in different amounts, under conditions favoring extension of said oligonucleotide primer to form nucleic acid fragments complementary to the nucleic acid to be sequenced; separating nucleic acid fragments by size; and determining nucleic acid sequence wherein said agents are differentiated from each other by intensity of a label in primer extension products formed.

100. A method for in vitro mutagenesis of a cloned DNA fragment comprising providing said cloned fragment and a modified Pol II-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase to incorporate a dideoxynucleotide relative to a corresponding deoxynucleotide compared to ability of a corresponding naturally-occurring unmodified DNA polymerase, contacting said cloned fragment with said polymerase under conditions for synthesizing a DNA strand from said fragment, wherein said conditions cause formation of said DNA strand by incorporation of a plurality of individual contiguous bases able to base-pair with said fragment and incorporation of a nucleotide base unable to base pair with said fragment.

101. A method for in vitro mutagenesis of a template DNA fragment comprising providing a primer and said template, said primer having contiguous bases able to base-pair with contiguous bases of said template except at least one base which is unable to base-pair with said template, and extending said primer with a modified Pol II-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase relative to a corresponding deoxynucleotide to incorporate a dideoxynucleotide compared to ability of a corresponding naturally-occurring unmodified DNA polymerase.

102. A method for producing blunt-ended double-stranded DNA from a linear DNA molecule having a 5' end comprising a single-stranded region, wherein the 3' end of said molecule is double stranded and has no 3' protruding termini, comprising incubating said DNA molecule with a modified Pol II-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase to incorporate a dideoxynucleotide relative to a corresponding deoxynucleotide compared to ability of a corresponding naturally-occurring unmodified DNA polymerase, wherein said polymerase acts on said single-stranded region to produce a blunt-ended double stranded DNA molecule.

103. A method for labeling a 3' end of a DNA fragment comprising incubating said DNA fragment with a modified Pol II-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase to incorporate a dideoxynucleotide relative to a corresponding deoxynucleotide compared to ability of a corresponding naturally-occurring unmodified DNA polymerase and a labelled deoxynucleotide species under conditions in which said 3' end of said DNA fragment is extended by said polymerase and thereby labelled by addition of said labelled deoxynucleotide to said DNA fragment.

104. A method of amplification of a DNA sequence comprising annealing a first and second primer to opposite strands of a double-stranded DNA sequence and incubating the annealed mixture with a modified Pol II-type DNA polymerase modified by having a tyrosine residue at an amino acid position corresponding to T7 DNA polymerase residue 526 or at an amino acid position corresponding to E. coli DNA polymerase residue 762 in its dNMP binding site to increase ability of said polymerase to incorporate a dideoxynucleotide relative to a corresponding deoxynucleotide compared to ability of a corresponding naturally-occurring unmodified DNA polymerase, wherein said first and second primers anneal to opposite strands of said DNA sequence with their 3' ends directed towards each other after annealing, and with the DNA sequence to be amplified located between the first and second primers.

105. A purified Pol II-type DNA polymerase having a tyrosine residue at an amino acid position corresponding to T7 DNA polymerase residue 526 or at an amino acid position corresponding to E. coli DNA polymerase residue 762 in its dNMP binding site, whereby ability to incorporate a dideoxynucleotide relative to a corresponding deoxynucleotide is increased compared to ability of a corresponding naturally occurring unmodified DNA polymerase.

106. The DNA polymerase according to claim 105 wherein the DNA polymerase is a Pol II type DNA polymerase and the deoxynucleotide binding site comprises the amino acid residue sequence K $N_1$ $N_2$ $N_3$ $N_4$ $N_5$ $N_6$ Y G wherein each N is independently any amino acid residue and said $N_4$ is tyrosine.

107. The DNA polymerase according to claim 106 wherein the DNA polymerase is a thermostable DNA polymerase.

108. Purified nucleic acid encoding a DNA polymerase according to claim 105.

* * * * *

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 1:

Arg Arg Ser Ala Lys Ala Ile Asn Phe Gly Leu Ile Tyr Gly
                5                          10

( 2 ) INFORMATION FOR SEQ ID NO: 2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 2:

Arg Arg Ala Ala Lys Thr Ile Asn Phe Gly Val Leu Tyr Gly
                5                          10

( 2 ) INFORMATION FOR SEQ ID NO: 3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 3:

Arg Asp Asn Ala Lys Thr Phe Ile Tyr Gly Phe Leu Tyr Gly
                5                          10

( 2 ) INFORMATION FOR SEQ ID NO: 4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 4:

Arg Asp Asn Ala Lys Thr Phe Ile Tyr Gly Phe Leu Tyr Gly
              5                           10

( 2 ) INFORMATION FOR SEQ ID NO: 5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 5:

Arg Arg Ser Ala Lys Ala Ile Asn Phe Gly Leu Ile Tyr Gly
              5                           10

( 2 ) INFORMATION FOR SEQ ID NO: 6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 6:

Arg Arg Ser Ala Lys Thr Phe Ile Tyr Gly Phe Leu Tyr Gly
              5                           10

( 2 ) INFORMATION FOR SEQ ID NO: 7:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 7:

Arg Asp Asn Ala Lys Ala Ile Asn Phe Gly Phe Leu Tyr Gly
              5                           10

( 2 ) INFORMATION FOR SEQ ID NO: 8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 8:

Arg Asp Asn Ala Lys Ala Ile Ile Tyr Gly Phe Leu Tyr Gly
              5                           10

( 2 ) INFORMATION FOR SEQ ID NO: 9:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 9:

Arg Asp Asn Ala Lys Thr Phe Asn Phe Gly Phe Leu Tyr Gly
                  5                   10

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) SEQUENCE DESCRIPTION: SEQ ID NO: 10:

Arg Asp Asn Ala Lys Thr Phe Asn Tyr Gly Phe Leu Tyr Gly
                  5                   10

(2) INFORMATION FOR SEQ ID NO: 11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) SEQUENCE DESCRIPTION: SEQ ID NO: 11:

Arg Asp Asn Ala Lys Thr Phe Ile Phe Gly Phe Leu Tyr Gly
                  5                   10

(2) INFORMATION FOR SEQ ID NO: 12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) SEQUENCE DESCRIPTION: SEQ ID NO: 12:

Arg Arg Ser Ala Lys Ala Ile Asn Phe Gly Leu Ile Tyr Gly
                  5                   10

(2) INFORMATION FOR SEQ ID NO: 13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) SEQUENCE DESCRIPTION: SEQ ID NO: 13:

Arg Asp Asn Ala Lys Thr Phe Ile Tyr Gly Phe Leu Tyr Gly
                  5                   10

(2) INFORMATION FOR SEQ ID NO: 14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) SEQUENCE DESCRIPTION: SEQ ID NO: 14:

Arg Arg Ser Ala Lys Thr Phe Ile Tyr Gly Leu Ile Tyr Gly
                  5                   10

(2) INFORMATION FOR SEQ ID NO: 15:

(i) SEQUENCE CHARACTERISTICS:
        (A) LENGTH: 14 amino acids
        (B) TYPE: amino acid (C) STRANDEDNESS: single
(D) TOPOLOGY: linear (ii) SEQUENCE DESCRIPTION: SEQ ID NO: 15:

Arg Arg Ser Ala Lys Thr Phe Asn Phe Gly Leu Ile Tyr Gly
               5                       10

(2) INFORMATION FOR SEQ ID NO: 16:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) SEQUENCE DESCRIPTION: SEQ ID NO: 16:

Arg Arg Ser Ala Lys Ala Ile Ile Tyr Gly Leu Ile Tyr Gly
               5                       10

(2) INFORMATION FOR SEQ ID NO: 17:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) SEQUENCE DESCRIPTION: SEQ ID NO: 17:

Arg Arg Ser Ala Lys Ala Ile Ile Phe Gly Leu Ile Tyr Gly
               5                       10

(2) INFORMATION FOR SEQ ID NO: 18:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) SEQUENCE DESCRIPTION: SEQ ID NO: 18:

Arg Arg Ser Ala Lys Ala Ile Asn Tyr Gly Leu Ile Tyr Gly
               5                       10

(2) INFORMATION FOR SEQ ID NO: 19:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) SEQUENCE DESCRIPTION: SEQ ID NO: 19:

Arg Arg Ala Ala Lys Thr Ile Asn Phe Gly Val Leu Tyr Gly
               5                       10

(2) INFORMATION FOR SEQ ID NO: 20:

(i) SEQUENCE CHARACTERISTICS:
   (A) LENGTH: 14 amino acids
   (B) TYPE: amino acid
   (C) STRANDEDNESS: single
   (D) TOPOLOGY: linear (ii) SEQUENCE DESCRIPTION: SEQ ID NO: 20:

Arg Asp Asn Ala Lys Thr Ile Asn Phe Gly Val Leu Tyr Gly
               5                       10

(2) INFORMATION FOR SEQ ID NO: 21:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) SEQUENCE DESCRIPTION: SEQ ID NO: 21:

Arg Arg Ala Ala Lys Thr Phe Ile Tyr Gly Phe Leu Tyr Gly
              5                      10

( 2 ) INFORMATION FOR SEQ ID NO: 22:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 22:

Arg Arg Ala Ala Lys Thr Ile Ile Tyr Gly Val Leu Tyr Gly
              5                      10

( 2 ) INFORMATION FOR SEQ ID NO: 23:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 23:

Arg Arg Ala Ala Lys Thr Ile Ile Phe Gly Val Leu Tyr Gly
              5                      10

( 2 ) INFORMATION FOR SEQ ID NO: 24:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) SEQUENCE DESCRIPTION: SEQ ID NO: 24:

Arg Arg Ala Ala Lys Thr Ile Asn Tyr Gly Val Leu Tyr Gly
              5                      10

( 2 ) INFORMATION FOR SEQ ID NO: 25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

GTAAAACGAA CGGCCAGT                                  18

( 2 ) INFORMATION FOR SEQ ID NO: 26:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

TTTTCCCAGT CACGACGTTG TAAAACGACG GCCAGTGCCA    40

(2) INFORMATION FOR SEQ ID NO: 27:

(i) SEQUENCE CHARACTERISTICS:
 (A) LENGTH: 30 base pairs
 (B) TYPE: nucleic acid
 (C) STRANDEDNESS: single
 (D) TOPOLOGY: linear (xi) SEQUENCE DESCRIPTION: SEQ ID NO: 27:

GGCGACGTTG TAAAACGACG GCCAGTGCCA 30

(2) INFORMATION FOR SEQ ID NO: 28:

(i) SEQUENCE CHARACTERISTICS:
 (A) LENGTH: 33 base pairs
 (B) TYPE: nucleic acid
 (C) STRANDEDNESS: single
 (D) TOPOLOGY: linear (xi) SEQUENCE DESCRIPTION: SEQ ID NO: 28:

CCCCTTGGCA CTGGCCGTCG TTTTACAACG TCG 33

(2) INFORMATION FOR SEQ ID NO: 29:

(i) SEQUENCE CHARACTERISTICS:
 (A) LENGTH: 35 base pairs
 (B) TYPE: nucleic acid
 (C) STRANDEDNESS: single
 (D) TOPOLOGY: linear (xi) SEQUENCE DESCRIPTION: SEQ ID NO: 29:

TTTTGACTGG CACTGGCCGT CGTTTTACAA CGTCG 35